United States Patent
Soderberg et al.

(10) Patent No.: US 9,737,115 B2
(45) Date of Patent: Aug. 22, 2017

(54) DEVICES AND METHODS FOR ADJUSTING THE FIT OF FOOTWEAR

(71) Applicant: Boa Technology Inc., Denver, CO (US)

(72) Inventors: Mark Soderberg, Conifer, CO (US);
Brett Vladika, Golden, CO (US);
Robert Burns, Denver, CO (US);
Michael Nickel, Golden, CO (US);
Aaron Venturini, Denver, CO (US);
Jesse Cotterman, Evergreen, CO (US)

(73) Assignee: Boa Technology Inc., Denver, CO (US)

( * ) Notice: Subject to any disclaimer, the term of this patent is extended or adjusted under 35 U.S.C. 154(b) by 219 days.

(21) Appl. No.: 14/073,773

(22) Filed: Nov. 6, 2013

(65) Prior Publication Data

US 2014/0123449 A1   May 8, 2014

Related U.S. Application Data

(60) Provisional application No. 61/723,218, filed on Nov. 6, 2012.

(51) Int. Cl.
| | |
|---|---|
| *A43C 1/00* | (2006.01) |
| *A43C 1/06* | (2006.01) |
| *A43C 11/16* | (2006.01) |

(52) U.S. Cl.
CPC .............. *A43C 1/003* (2013.01); *A43C 1/06* (2013.01); *A43C 11/165* (2013.01); *Y10T 24/3703* (2015.01); *Y10T 29/49826* (2015.01)

(58) Field of Classification Search
None
See application file for complete search history.

(56) References Cited

U.S. PATENT DOCUMENTS

| | | | |
|---|---|---|---|
| 59,332 A | 10/1866 | White et al. | |
| 80,834 A | 8/1868 | Prussia | |

(Continued)

FOREIGN PATENT DOCUMENTS

| | | |
|---|---|---|
| CA | 2112789 | 8/1994 |
| CA | 2114387 | 8/1994 |

(Continued)

OTHER PUBLICATIONS

International Search Report and Written Opinion mailed Jun. 9, 2014 for International Patent Application No. PCT/US2013/068814 filed Nov. 6, 2013, 18 pages.

(Continued)

*Primary Examiner* — Jack W Lavinder
(74) *Attorney, Agent, or Firm* — Kilpatrick Townsend & Stockton LLP

(57) ABSTRACT

A lacing system for tightening an article includes a first guide that is coupled with the article and positioned within a first zone of the article and a second guide that is coupled with the article and positioned within a second zone of the article with at least a portion of the second zone being different than the first zone. A first tension member is guided by the first guide within the first zone and a second tension member is guided by the second guide within the second zone. Tensioning of the first tension member or second tension member causes tightening of the respective zone of the article. A tensioning mechanism is also coupled with the article and with the first and second tension members. The tensioning mechanism is configured to tension the first and second tension members to tighten the first and second zones of the article.

23 Claims, 40 Drawing Sheets

(56) References Cited

U.S. PATENT DOCUMENTS

| | | | |
|---|---|---|---|
| 117,530 A | 8/1871 | Foote |
| 228,946 A | 6/1880 | Schulz |
| 230,759 A | 8/1880 | Drummond |
| 301,854 A | 7/1884 | Buch |
| 371,394 A | 10/1887 | Warren |
| 379,113 A | 3/1888 | Hibberd |
| 460,743 A | 10/1891 | Dickson, Jr. |
| 746,563 A | 12/1903 | McMahon |
| 819,993 A | 5/1906 | Haws et al. |
| 886,779 A | 5/1908 | Dunstan |
| 908,704 A | 1/1909 | Sprinkle |
| 1,060,422 A | 4/1913 | Bowdish |
| 1,062,511 A | 5/1913 | Short |
| 1,083,775 A | 1/1914 | Thomas |
| 1,090,438 A | 3/1914 | Worth et al. |
| 1,170,472 A | 2/1916 | Barber |
| 1,288,859 A | 12/1918 | Feller et al. |
| 1,390,991 A | 9/1921 | Fotchuk |
| 1,393,188 A | 10/1921 | Whiteman |
| 1,469,661 A | 2/1922 | Migita |
| 1,412,486 A | 4/1922 | Paine |
| 1,416,203 A | 5/1922 | Hobson |
| 1,429,657 A | 9/1922 | Trawinski |
| 1,481,903 A | 4/1923 | Hart |
| 1,466,673 A | 9/1923 | Solomon et al. |
| 1,530,713 A | 2/1924 | Clark |
| 1,502,919 A | 7/1924 | Seib |
| 1,505,430 A | 8/1924 | Richard |
| 1,548,407 A | 8/1925 | Chisholm |
| 1,862,047 A | 6/1932 | Boulet et al. |
| 1,995,243 A | 6/1934 | Clarke |
| 2,088,851 A | 8/1937 | Gantenbein |
| 2,109,751 A | 3/1938 | Matthias et al. |
| 2,124,310 A | 9/1938 | Murr, Jr. |
| 2,316,102 A | 4/1943 | Preston |
| 2,539,026 A | 1/1951 | Mangold |
| 2,611,940 A | 9/1952 | Cairns |
| 2,673,381 A | 3/1954 | Dueker |
| 2,893,090 A | 7/1959 | Pagoda |
| 2,907,086 A | 10/1959 | Ord |
| 2,926,406 A | 3/1960 | Zahnor et al. |
| 2,991,523 A | 7/1961 | Del Conte |
| 3,028,602 A | 4/1962 | Miller |
| 3,035,319 A | 5/1962 | Wolff |
| D193,807 S | 10/1962 | Stanley |
| 3,106,003 A | 10/1963 | Herdman |
| 3,112,545 A | 12/1963 | Williams |
| 3,122,810 A | 3/1964 | Lawrence et al. |
| 3,163,900 A | 1/1965 | Martin |
| D200,394 S | 2/1965 | Hakim |
| 3,169,325 A | 2/1965 | Fesl |
| 3,193,950 A | 7/1965 | Liou |
| 3,197,155 A | 7/1965 | Chow |
| 3,214,809 A | 11/1965 | Zahnor |
| 3,221,384 A | 12/1965 | Aufenacker |
| 3,276,090 A | 10/1966 | Nigon |
| D206,146 S | 11/1966 | Hendershot |
| 3,345,707 A | 10/1967 | Rita |
| D210,649 S | 4/1968 | Getgay |
| 3,401,437 A | 9/1968 | Christpohersen |
| 3,430,303 A | 3/1969 | Perrin et al. |
| 3,491,465 A | 1/1970 | Martin |
| 3,545,106 A | 12/1970 | Martin |
| 3,618,232 A | 11/1971 | Shnuriwsky |
| 3,668,791 A | 6/1972 | Salzman et al. |
| 3,678,539 A | 7/1972 | Graup |
| 3,703,775 A | 11/1972 | Gatti |
| 3,729,779 A | 5/1973 | Porth |
| 3,738,027 A | 6/1973 | Schoch |
| 3,793,749 A | 2/1974 | Gertsch et al. |
| 3,808,644 A | 5/1974 | Schoch |
| 3,845,575 A | 11/1974 | Boden |
| 3,934,346 A | 1/1976 | Sasaki et al. |
| 3,975,838 A | 8/1976 | Martin |
| 4,084,267 A | 4/1978 | Zadina |
| 4,130,949 A | 12/1978 | Seidel |
| 4,142,307 A | 3/1979 | Martin |
| 4,227,322 A | 10/1980 | Annovi |
| 4,261,081 A | 4/1981 | Lott |
| 4,267,622 A | 5/1981 | Burnett-Johnston |
| RE31,052 E | 10/1982 | Adams |
| 4,408,403 A | 10/1983 | Martin |
| 4,417,703 A | 11/1983 | Weinhold |
| 4,433,456 A | 2/1984 | Baggio |
| 4,452,405 A | 6/1984 | Adomeit |
| 4,463,761 A | 8/1984 | Pols et al. |
| 4,480,395 A | 11/1984 | Schoch |
| 4,507,878 A | 4/1985 | Semouha |
| 4,516,576 A | 5/1985 | Kirchner |
| 4,551,932 A | 11/1985 | Schoch |
| 4,553,342 A | 11/1985 | Derderian et al. |
| 4,555,830 A | 12/1985 | Petrini et al. |
| 4,574,500 A | 3/1986 | Aldinio et al. |
| 4,616,432 A | 10/1986 | Bunch et al. |
| 4,616,524 A | 10/1986 | Biodia |
| 4,619,057 A | 10/1986 | Sartor et al. |
| 4,620,378 A | 11/1986 | Sartor |
| 4,631,839 A | 12/1986 | Bonetti et al. |
| 4,631,840 A | 12/1986 | Gamm |
| 4,633,599 A | 1/1987 | Morell et al. |
| 4,644,938 A | 2/1987 | Yates et al. |
| 4,654,985 A | 4/1987 | Chalmers |
| 4,660,300 A | 4/1987 | Morell et al. |
| 4,660,302 A | 4/1987 | Arieh et al. |
| 4,680,878 A | 7/1987 | Pozzobon et al. |
| 4,719,670 A | 1/1988 | Kurt |
| 4,719,709 A | 1/1988 | Vaccari |
| 4,719,710 A | 1/1988 | Pozzobon |
| 4,722,477 A | 2/1988 | Floyd |
| 4,741,115 A | 5/1988 | Pozzobon |
| 4,748,726 A | 6/1988 | Schoch |
| 4,760,653 A | 8/1988 | Baggio |
| 4,780,969 A | 11/1988 | White, Jr. |
| 4,787,124 A | 11/1988 | Pozzobon et al. |
| 4,790,081 A | 12/1988 | Benoit et al. |
| 4,796,829 A | 1/1989 | Pozzobon et al. |
| 4,799,297 A | 1/1989 | Baggio et al. |
| 4,802,291 A | 2/1989 | Sartor |
| 4,811,503 A | 3/1989 | Iwama |
| 4,826,098 A | 5/1989 | Pozzobon et al. |
| 4,841,649 A * | 6/1989 | Baggio et al. ......... A43C 11/16 24/68 SK |
| 4,856,207 A | 8/1989 | Datson |
| 4,862,878 A | 9/1989 | Davison |
| 4,870,723 A | 10/1989 | Pozzobon et al. |
| 4,870,761 A | 10/1989 | Tracy |
| 4,884,760 A | 12/1989 | Baggio et al. |
| 4,901,938 A | 2/1990 | Cantley et al. |
| 4,924,605 A | 5/1990 | Spademan |
| D308,282 S | 6/1990 | Bergman et al. |
| 4,937,953 A | 7/1990 | Walkhoff |
| 4,961,544 A | 10/1990 | Biodia |
| 4,974,299 A | 12/1990 | Moon |
| 4,979,953 A | 12/1990 | Spence |
| 4,989,805 A | 2/1991 | Burke |
| 5,001,817 A | 3/1991 | De Bortoli et al. |
| 5,016,327 A | 5/1991 | Klausner |
| 5,042,177 A | 8/1991 | Schoch |
| 5,062,225 A | 11/1991 | Gorza |
| 5,065,480 A | 11/1991 | DeBortoli |
| 5,065,481 A | 11/1991 | Walkhoff |
| 5,108,216 A | 4/1992 | Geyer et al. |
| 5,117,567 A | 6/1992 | Berger |
| 5,152,038 A | 10/1992 | Schoch |
| 5,157,813 A | 10/1992 | Carroll |
| 5,158,428 A | 10/1992 | Gessner et al. |
| 5,177,882 A | 1/1993 | Berger |
| 5,181,331 A | 1/1993 | Berger |
| 5,184,378 A | 2/1993 | Batra |
| D333,552 S | 3/1993 | Berger et al. |
| 5,205,055 A | 4/1993 | Harrell |
| 5,233,767 A | 8/1993 | Kramer |
| 5,249,377 A | 10/1993 | Walkhoff |
| 5,259,094 A | 11/1993 | Zepeda |

(56) References Cited

U.S. PATENT DOCUMENTS

| | | |
|---|---|---|
| 5,315,741 A | 5/1994 | Debberke |
| 5,319,868 A | 6/1994 | Hallenbeck |
| 5,319,869 A | 6/1994 | McDonald et al. |
| 5,325,613 A | 7/1994 | Sussmann |
| 5,327,662 A | 7/1994 | Hallenbeck |
| 5,333,398 A | 8/1994 | Seo |
| 5,335,401 A | 8/1994 | Hanson |
| 5,341,583 A | 8/1994 | Hallenbeck |
| 5,345,697 A | 9/1994 | Quellais |
| 5,355,596 A | 10/1994 | Sussmann |
| 5,357,654 A | 10/1994 | Hsing-Chi |
| 5,371,957 A | 12/1994 | Gaudio |
| 5,381,609 A | 1/1995 | Hieblinger |
| 5,392,535 A | 2/1995 | Van Noy et al. |
| D357,576 S | 4/1995 | Steinweis |
| 5,425,161 A | 6/1995 | Schoch |
| 5,425,185 A | 6/1995 | Gansler |
| 5,430,960 A | 7/1995 | Richardson |
| 5,433,648 A | 7/1995 | Frydman |
| 5,454,140 A | 10/1995 | Murai |
| 5,463,822 A | 11/1995 | Miller |
| 5,477,593 A | 12/1995 | Leick |
| D367,755 S | 3/1996 | Jones |
| D367,954 S | 3/1996 | Dion |
| 5,502,902 A | 4/1996 | Sussmann |
| 5,511,325 A | 4/1996 | Hieblinger |
| 5,526,585 A | 6/1996 | Brown et al. |
| 5,535,531 A | 7/1996 | Karabed et al. |
| 5,537,763 A | 7/1996 | Donnadieu et al. |
| 5,557,864 A | 9/1996 | Marks |
| 5,566,474 A | 10/1996 | Leick et al. |
| D375,831 S | 11/1996 | Perry |
| 5,596,820 A | 1/1997 | Edauw et al. |
| 5,599,000 A | 2/1997 | Bennett |
| 5,599,288 A | 2/1997 | Shirley et al. |
| 5,600,874 A | 2/1997 | Jungkind |
| 5,606,778 A | 3/1997 | Jungkind |
| 5,607,448 A | 3/1997 | Stahl et al. |
| D379,113 S | 5/1997 | McDonald et al. |
| D379,626 S | 6/1997 | Mak |
| 5,638,588 A | 6/1997 | Jungkind |
| 5,640,785 A | 6/1997 | Egelja |
| 5,647,104 A | 7/1997 | James |
| 5,651,198 A | 7/1997 | Sussmann |
| 5,669,116 A | 9/1997 | Jungkind |
| 5,692,319 A | 12/1997 | Parker et al. |
| 5,718,021 A | 2/1998 | Tatum |
| 5,718,065 A | 2/1998 | Locker |
| 5,720,084 A | 2/1998 | Chen |
| 5,732,483 A | 3/1998 | Cagliari |
| 5,732,648 A | 3/1998 | Aragon |
| 5,736,696 A | 4/1998 | Del Rosso |
| 5,737,854 A | 4/1998 | Sussmann |
| 5,755,044 A | 5/1998 | Veylupek |
| 5,756,298 A | 5/1998 | Burczak |
| 5,761,777 A | 6/1998 | Leick |
| 5,772,146 A | 6/1998 | Kawamoto et al. |
| 5,784,809 A | 7/1998 | McDonald |
| 5,791,068 A | 8/1998 | Bernier et al. |
| 5,819,378 A | 10/1998 | Doyle |
| 5,833,640 A | 11/1998 | Vazquez, Jr. et al. |
| 5,839,210 A | 11/1998 | Bernier et al. |
| 5,845,371 A | 12/1998 | Chen |
| 5,906,057 A | 5/1999 | Borsoi |
| 5,909,946 A | 6/1999 | Okajima |
| D413,197 S | 8/1999 | Faye |
| 5,934,599 A | 8/1999 | Hammerslag |
| 5,937,542 A | 8/1999 | Bourdeau |
| 5,956,823 A | 9/1999 | Borel |
| 5,971,946 A | 10/1999 | Quinn et al. |
| 6,015,110 A | 1/2000 | Lai |
| 6,032,387 A | 3/2000 | Johnson |
| 6,038,791 A | 3/2000 | Cornelius et al. |
| 6,052,921 A | 4/2000 | Oreck |
| 6,070,886 A | 6/2000 | Cornelius et al. |
| 6,070,887 A | 6/2000 | Cornelius et al. |
| 6,083,857 A | 7/2000 | Bottger |
| 6,088,936 A | 7/2000 | Bahl |
| 6,102,412 A | 8/2000 | Staffaroni |
| D430,724 S | 9/2000 | Matis et al. |
| 6,119,318 A | 9/2000 | Maurer |
| 6,119,372 A | 9/2000 | Okajima |
| 6,128,835 A | 10/2000 | Ritter et al. |
| 6,128,836 A | 10/2000 | Barret |
| 6,148,489 A | 11/2000 | Dickie et al. |
| D438,452 S | 3/2001 | Tsai |
| 6,202,953 B1 | 3/2001 | Hammerslag |
| 6,219,891 B1 | 4/2001 | Maurer et al. |
| 6,240,657 B1 | 6/2001 | Weber et al. |
| 6,256,798 B1 | 7/2001 | Egolf et al. |
| 6,267,390 B1 | 7/2001 | Maravetz et al. |
| 6,286,233 B1 | 9/2001 | Gaither |
| 6,289,558 B1 | 9/2001 | Hammerslag |
| 6,311,633 B1 | 11/2001 | Keire |
| D456,130 S | 4/2002 | Towns |
| 6,370,743 B2 | 4/2002 | Choe |
| 6,401,364 B1 | 6/2002 | Burt |
| 6,416,074 B1 | 7/2002 | Maravetz et al. |
| 6,467,195 B2 | 10/2002 | Pierre et al. |
| 6,477,793 B1 | 11/2002 | Pruitt et al. |
| 6,502,286 B1 | 1/2003 | Dubberke |
| 6,543,159 B1 | 4/2003 | Carpenter et al. |
| 6,568,103 B2 | 5/2003 | Durocher |
| D477,364 S | 7/2003 | Tsai |
| 6,606,804 B2 | 8/2003 | Kaneko et al. |
| 6,694,643 B1 | 2/2004 | Hsu |
| 6,708,376 B1 | 3/2004 | Landry |
| 6,711,787 B2 | 3/2004 | Jungkind et al. |
| 6,735,829 B2 | 5/2004 | Hsu |
| 6,757,991 B2 | 7/2004 | Sussmann |
| 6,775,928 B2 | 8/2004 | Grande et al. |
| 6,792,702 B2 | 9/2004 | Borsoi et al. |
| D497,183 S | 10/2004 | Chiu |
| 6,802,439 B2 | 10/2004 | Azam et al. |
| 6,823,610 B1 | 11/2004 | Ashley |
| 6,871,812 B1 | 3/2005 | Chang |
| 6,877,256 B2 | 4/2005 | Martin et al. |
| 6,899,720 B1 | 5/2005 | McMillan |
| 6,922,917 B2 | 8/2005 | Kerns et al. |
| 6,938,913 B2 | 9/2005 | Elkington |
| 6,945,543 B2 | 9/2005 | De Bortoli et al. |
| D510,183 S | 10/2005 | Tresser |
| 6,976,972 B2 | 12/2005 | Bradshaw |
| 6,993,859 B2 | 2/2006 | Martin et al. |
| D521,226 S | 5/2006 | Douglas et al. |
| 7,073,279 B2 | 7/2006 | Min |
| 7,076,843 B2 | 7/2006 | Sakabayashi |
| 7,082,701 B2 | 8/2006 | Dalgaard et al. |
| 7,096,559 B2 | 8/2006 | Johnson et al. |
| 7,134,224 B2 | 11/2006 | Elkington et al. |
| 7,266,911 B2 | 9/2007 | Holzer et al. |
| 7,281,341 B2 | 10/2007 | Reagan et al. |
| 7,293,373 B2 | 11/2007 | Reagan et al. |
| 7,331,126 B2 | 2/2008 | Johnson |
| 7,343,701 B2 | 3/2008 | Pare et al. |
| 7,360,282 B2 | 4/2008 | Borsoi |
| 7,367,522 B2 | 5/2008 | Chen |
| 7,386,947 B2 | 6/2008 | Martin et al. |
| 7,392,602 B2 | 7/2008 | Reagan et al. |
| 7,401,423 B2 | 7/2008 | Reagan et al. |
| D587,105 S | 2/2009 | Chang |
| 7,490,458 B2 | 2/2009 | Ford |
| 7,516,914 B2 | 4/2009 | Kovacevich et al. |
| 7,568,298 B2 | 8/2009 | Kerns |
| 7,582,102 B2 | 9/2009 | Heinz et al. |
| 7,584,528 B2 | 9/2009 | Hu |
| 7,591,050 B2 | 9/2009 | Hammerslag |
| 7,597,675 B2 | 10/2009 | Ingimundarson et al. |
| 7,600,660 B2 | 10/2009 | Kasper et al. |
| 7,617,573 B2 | 11/2009 | Chen |
| 7,624,517 B2 | 12/2009 | Smith |
| 7,648,404 B1 | 1/2010 | Martin |
| 7,650,705 B2 | 1/2010 | Donnadieu et al. |
| 7,694,354 B2 | 4/2010 | Philpott et al. |

(56) References Cited

U.S. PATENT DOCUMENTS

| | | |
|---|---|---|
| 7,752,774 B2 | 7/2010 | Ussher |
| 7,757,412 B2 | 7/2010 | Farys |
| 7,774,956 B2 | 8/2010 | Dua et al. |
| D626,322 S | 11/2010 | Servettaz |
| 7,841,106 B2 | 11/2010 | Farys |
| 7,871,334 B2 | 1/2011 | Young et al. |
| 7,877,845 B2 | 2/2011 | Signori |
| D633,375 S | 3/2011 | Jablonka |
| 7,900,378 B1 | 3/2011 | Busse |
| 7,908,769 B2 | 3/2011 | Pellegrini |
| 7,947,061 B1 | 5/2011 | Reis |
| 7,950,112 B2 | 5/2011 | Hammerslag et al. |
| 7,954,204 B2 | 6/2011 | Hammerslag et al. |
| 7,963,049 B2 | 6/2011 | Messmer |
| 7,992,261 B2 | 8/2011 | Hammerslag et al. |
| D646,790 S | 10/2011 | Castillo et al. |
| 8,056,150 B2 | 11/2011 | Stokes et al. |
| 8,056,265 B2 | 11/2011 | Pirkle |
| 8,061,061 B1 | 11/2011 | Rivas |
| 8,074,379 B2 | 12/2011 | Robinson, Jr. et al. |
| 8,091,182 B2 | 1/2012 | Hammerslag et al. |
| 8,109,015 B2 | 2/2012 | Signori |
| D663,850 S | 7/2012 | Joseph |
| D663,851 S | 7/2012 | Joseph |
| 8,215,033 B2 | 7/2012 | Carboy et al. |
| 8,231,074 B2 | 7/2012 | Hu et al. |
| D665,088 S | 8/2012 | Joseph |
| 8,235,321 B2 | 8/2012 | Chen |
| 8,245,371 B2 | 8/2012 | Chen |
| 8,257,293 B2 | 9/2012 | Ingimundarson et al. |
| 8,266,827 B2 | 9/2012 | Dojan et al. |
| 8,277,401 B2 | 10/2012 | Hammerslag et al. |
| 8,302,329 B2 | 11/2012 | Hurd et al. |
| 8,303,527 B2 | 11/2012 | Joseph |
| 8,308,098 B2 | 11/2012 | Chen |
| 8,321,999 B2 | 12/2012 | Boden |
| D673,443 S | 1/2013 | Elrod |
| 8,353,087 B2 | 1/2013 | Chen |
| 8,353,088 B2 | 1/2013 | Ha |
| 8,381,362 B2 | 2/2013 | Hammerslag |
| D677,045 S | 3/2013 | Voskuil |
| D679,019 S | 3/2013 | Siddle et al. |
| D679,175 S | 4/2013 | Moreau et al. |
| 8,424,168 B2 | 4/2013 | Soderberg et al. |
| 8,434,200 B2 | 5/2013 | Chen |
| 8,468,657 B2 | 6/2013 | Soderberg |
| 8,490,299 B2 | 7/2013 | Dua et al. |
| 8,516,662 B2 | 8/2013 | Goodman et al. |
| D691,027 S | 10/2013 | Rainer |
| 8,578,632 B2 | 11/2013 | Bell et al. |
| 8,652,164 B1 | 2/2014 | Aston |
| D702,529 S | 4/2014 | Diez Herrera |
| 8,713,820 B2 | 5/2014 | Kerns et al. |
| D712,727 S | 9/2014 | Geiger |
| 8,984,719 B2 | 3/2015 | Soderberg et al. |
| 9,072,341 B2 | 7/2015 | Jungkind |
| D735,987 S | 8/2015 | Hsu |
| 9,101,181 B2 | 8/2015 | Soderberg et al. |
| 9,125,455 B2 | 9/2015 | Kerns et al. |
| 9,138,030 B2 | 9/2015 | Soderberg et al. |
| 9,248,040 B2 | 2/2016 | Soderberg et al. |
| 9,339,082 B2 | 5/2016 | Hammerslag et al. |
| 9,375,053 B2 | 6/2016 | Burns et al. |
| 9,408,437 B2 | 8/2016 | Goodman et al. |
| 2002/0002781 A1 | 1/2002 | Bouvier |
| 2002/0050076 A1 | 5/2002 | Borsoi et al. |
| 2002/0062579 A1 | 5/2002 | Caeran |
| 2002/0095750 A1 | 7/2002 | Hammerslag |
| 2002/0129518 A1 | 9/2002 | Borsoi et al. |
| 2002/0148142 A1 | 10/2002 | Oorei et al. |
| 2002/0166260 A1 | 11/2002 | Borsoi |
| 2002/0178548 A1 | 12/2002 | Freed |
| 2003/0041478 A1 | 3/2003 | Liu |
| 2003/0051374 A1 | 3/2003 | Freed |
| 2003/0079376 A1 | 5/2003 | Oorei et al. |
| 2003/0144620 A1 | 7/2003 | Sieller |
| 2003/0150135 A1 | 8/2003 | Liu |
| 2003/0177662 A1 | 9/2003 | Elkington et al. |
| 2003/0204938 A1 | 11/2003 | Hammerslag |
| 2004/0041452 A1 | 3/2004 | Williams |
| 2004/0211039 A1 | 10/2004 | Livingston |
| 2004/0221433 A1 | 11/2004 | Wolfberg |
| 2005/0054962 A1 | 3/2005 | Bradshaw |
| 2005/0060912 A1 | 3/2005 | Holzer et al. |
| 2005/0081339 A1 | 4/2005 | Sakabayashi |
| 2005/0081403 A1 | 4/2005 | Mathieu |
| 2005/0087115 A1 | 4/2005 | Martin |
| 2005/0098673 A1 | 5/2005 | Huang |
| 2005/0102861 A1 | 5/2005 | Martin |
| 2005/0126043 A1 | 6/2005 | Reagan et al. |
| 2005/0172463 A1 | 8/2005 | Rolla |
| 2005/0178872 A1 | 8/2005 | Hyun |
| 2005/0184186 A1 | 8/2005 | Tsoi et al. |
| 2005/0198866 A1 | 9/2005 | Wiper et al. |
| 2005/0247813 A1 | 11/2005 | Kovacevich et al. |
| 2006/0135901 A1 | 6/2006 | Ingimundarson et al. |
| 2006/0156517 A1 | 7/2006 | Hammerslag et al. |
| 2006/0179685 A1 | 8/2006 | Borel et al. |
| 2006/0185193 A1 | 8/2006 | Pellegrini |
| 2006/0213085 A1 | 9/2006 | Azam |
| 2006/0287627 A1 | 12/2006 | Johnson |
| 2007/0006489 A1 | 1/2007 | Case, Jr. et al. |
| 2007/0063459 A1 | 3/2007 | Kavarsky |
| 2007/0068040 A1 | 3/2007 | Farys |
| 2007/0084956 A1 | 4/2007 | Chen |
| 2007/0113524 A1 | 5/2007 | Lander |
| 2007/0128959 A1 | 6/2007 | Cooke |
| 2007/0169378 A1 | 7/2007 | Sodeberg et al. |
| 2008/0016717 A1 | 1/2008 | Ruban |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0068204 A1 | 3/2008 | Carmen et al. |
| 2008/0083135 A1 | 4/2008 | Hammerslag et al. |
| 2008/0092279 A1 | 4/2008 | Chiang |
| 2008/0172848 A1 | 7/2008 | Chen |
| 2008/0196224 A1 | 8/2008 | Hu |
| 2009/0019734 A1 | 1/2009 | Reagan et al. |
| 2009/0071041 A1 | 3/2009 | Hooper |
| 2009/0090029 A1 | 4/2009 | Kishino |
| 2009/0172928 A1 | 7/2009 | Messmer et al. |
| 2009/0184189 A1 | 7/2009 | Soderberg et al. |
| 2009/0272007 A1 | 11/2009 | Beers et al. |
| 2009/0277043 A1 | 11/2009 | Graser et al. |
| 2010/0064547 A1 | 3/2010 | Kaplan |
| 2010/0101061 A1 | 4/2010 | Ha |
| 2010/0115744 A1 | 5/2010 | Fong |
| 2010/0139057 A1 | 6/2010 | Soderberg et al. |
| 2010/0154254 A1 | 6/2010 | Fletcher |
| 2010/0175163 A1 | 7/2010 | Litke |
| 2010/0251524 A1 | 10/2010 | Chen |
| 2010/0269373 A1 | 10/2010 | Pirkle |
| 2010/0299959 A1 | 12/2010 | Hammerslag |
| 2010/0319216 A1 | 12/2010 | Grenzke et al. |
| 2011/0000173 A1 | 1/2011 | Lander |
| 2011/0071647 A1 | 3/2011 | Mahon |
| 2011/0099843 A1 | 5/2011 | Jung |
| 2011/0162236 A1 | 7/2011 | Voskuil et al. |
| 2011/0167543 A1 | 7/2011 | Kovacevich et al. |
| 2011/0191992 A1 | 8/2011 | Chen |
| 2011/0197362 A1 | 8/2011 | Chella et al. |
| 2011/0225843 A1 | 9/2011 | Kerns et al. |
| 2011/0258876 A1 | 10/2011 | Baker et al. |
| 2011/0266384 A1 | 11/2011 | Goodman et al. |
| 2012/0000091 A1 | 1/2012 | Cotterman et al. |
| 2012/0004587 A1 | 1/2012 | Nickel et al. |
| 2012/0005865 A1 | 1/2012 | Boden |
| 2012/0005995 A1 | 1/2012 | Emery |
| 2012/0023717 A1 | 2/2012 | Chen |
| 2012/0047620 A1 | 3/2012 | Ellis et al. |
| 2012/0101417 A1 | 4/2012 | Joseph |
| 2012/0102783 A1 | 5/2012 | Swigart et al. |

(56) References Cited

U.S. PATENT DOCUMENTS

| | | |
|---|---|---|
| 2012/0138882 A1 | 6/2012 | Moore et al. |
| 2012/0157902 A1 | 6/2012 | Castillo et al. |
| 2012/0167290 A1 | 7/2012 | Kovacevich et al. |
| 2012/0174437 A1 | 7/2012 | Heard |
| 2012/0204381 A1 | 8/2012 | Ingimundarson et al. |
| 2012/0228419 A1 | 9/2012 | Chen |
| 2012/0246974 A1 | 10/2012 | Hammerslag et al. |
| 2012/0310273 A1 | 12/2012 | Thorpe |
| 2013/0012856 A1 | 1/2013 | Hammerslag et al. |
| 2013/0014359 A1 | 1/2013 | Chen |
| 2013/0019501 A1 | 1/2013 | Gerber |
| 2013/0025100 A1 | 1/2013 | Ha |
| 2013/0091667 A1 | 4/2013 | Chen |
| 2013/0091674 A1 | 4/2013 | Chen |
| 2013/0092780 A1 | 4/2013 | Soderberg et al. |
| 2013/0239303 A1 | 9/2013 | Cotterman et al. |
| 2013/0269219 A1 | 10/2013 | Burns et al. |
| 2013/0277485 A1 | 10/2013 | Soderberg et al. |
| 2013/0340283 A1 | 12/2013 | Bell et al. |
| 2013/0345612 A1 | 12/2013 | Bannister et al. |
| 2014/0068838 A1 | 3/2014 | Beers et al. |
| 2014/0082963 A1 | 3/2014 | Beers |
| 2014/0094728 A1 | 4/2014 | Soderberg et al. |
| 2014/0117140 A1 | 5/2014 | Goodman et al. |
| 2014/0123440 A1 | 5/2014 | Capra et al. |
| 2014/0123449 A1 | 5/2014 | Soderberg et al. |
| 2014/0208550 A1 | 7/2014 | Neiley |
| 2014/0221889 A1 | 8/2014 | Burns et al. |
| 2014/0257156 A1 | 9/2014 | Capra et al. |
| 2014/0290016 A1 | 10/2014 | Lovett et al. |
| 2014/0359981 A1 | 12/2014 | Cotterman et al. |
| 2015/0005685 A1 | 1/2015 | Chetlapalli et al. |
| 2015/0007422 A1 | 1/2015 | Cavanagh et al. |
| 2015/0014463 A1 | 1/2015 | Converse et al. |
| 2015/0026936 A1 | 1/2015 | Kerns et al. |
| 2015/0033519 A1 | 2/2015 | Hammerslag et al. |
| 2015/0059206 A1 | 3/2015 | Lovett et al. |
| 2015/0076272 A1 | 3/2015 | Trudel et al. |
| 2015/0089779 A1 | 4/2015 | Lawrence et al. |
| 2015/0089835 A1 | 4/2015 | Hammerslag et al. |
| 2015/0101160 A1 | 4/2015 | Soderberg et al. |
| 2015/0150705 A1 | 6/2015 | Capra et al. |
| 2015/0151070 A1 | 6/2015 | Capra et al. |
| 2015/0190262 A1 | 7/2015 | Capra et al. |
| 2015/0223608 A1 | 8/2015 | Capra et al. |
| 2015/0237962 A1 | 8/2015 | Soderberg et al. |
| 2015/0313319 A1 | 11/2015 | Ha |
| 2015/0335458 A1 | 11/2015 | Romo |
| 2016/0058127 A1 | 3/2016 | Burns et al. |
| 2016/0058130 A1 | 3/2016 | Boney |
| 2016/0157561 A1 | 6/2016 | Schum et al. |

FOREIGN PATENT DOCUMENTS

| | | |
|---|---|---|
| CH | 199766 | 9/1938 |
| CH | 204 834 A | 5/1939 |
| CN | 2613167 | 4/2004 |
| CN | 201015448 | 2/2008 |
| DE | 641976 | 2/1937 |
| DE | 23 41 658 | 3/1974 |
| DE | 29 00 077 A1 | 7/1980 |
| DE | 31 01 952 A1 | 9/1982 |
| DE | 38 13 470 | 11/1989 |
| DE | 43 02 401 A1 | 8/1994 |
| DE | 43 05 671 A1 | 9/1994 |
| DE | 9308037 | 10/1994 |
| DE | 43 26 049 A1 | 2/1995 |
| DE | 9315776 | 2/1995 |
| DE | 29503552.8 | 4/1995 |
| DE | 196 24 553 | 1/1998 |
| DE | 19945045 A1 | 3/2001 |
| DE | 20 2010 000 354 U1 | 6/2010 |
| DE | 11 2013 005 273 T5 | 9/2015 |
| EP | 0 056 953 | 8/1982 |
| EP | 0 099 504 | 2/1984 |
| EP | 0 123 050 | 10/1984 |
| EP | 0 155 596 | 9/1985 |
| EP | 0 201 051 | 11/1986 |
| EP | 0 255 869 | 2/1988 |
| EP | 0 297 342 A2 | 1/1989 |
| EP | 0 393 380 | 10/1990 |
| EP | 0 589 232 A1 | 3/1994 |
| EP | 0 589 233 A1 | 3/1994 |
| EP | 0 614 625 A1 | 9/1994 |
| EP | 0 651 954 A1 | 5/1995 |
| EP | 0 679 346 | 11/1995 |
| EP | 0 693 260 B1 | 1/1996 |
| EP | 0 734 662 A1 | 10/1996 |
| EP | 0 848 917 | 6/1998 |
| EP | 0 923 965 | 6/1999 |
| EP | 0 937 467 | 8/1999 |
| EP | 1163860 | 12/2001 |
| EP | 1 219 195 | 7/2002 |
| EP | 1 236 412 A | 9/2002 |
| EP | 2 052 636 A1 | 4/2009 |
| EP | 2298107 B1 | 3/2011 |
| EP | 2359708 | 8/2011 |
| FR | 1 404 799 | 7/1965 |
| FR | 2 019 991 A | 7/1970 |
| FR | 2 598 292 A | 11/1987 |
| FR | 2 726 440 A1 | 5/1996 |
| FR | 2 770 379 A1 | 5/1999 |
| FR | 2 814 919 A1 | 4/2002 |
| GB | 189911673 | 7/1899 |
| GB | 216400 | 5/1924 |
| GB | 2 449 722 A | 12/2008 |
| IT | 1220811 | 6/1990 |
| IT | PD 2003 000197 A | 4/2003 |
| IT | PD 2003 000198 A | 3/2005 |
| JP | 51-121375 | 10/1976 |
| JP | 53-124987 | 3/1977 |
| JP | 54-108125 | 2/1978 |
| JP | H02-236025 | 9/1990 |
| JP | 6-284906 | 2/1996 |
| JP | 3030988 | 11/1996 |
| JP | 3031760 | 12/1996 |
| JP | 10-199366 | 7/1998 |
| JP | 2004-016732 | 1/2004 |
| JP | 2004-041666 | 2/2004 |
| JP | 2009-504210 | 2/2009 |
| KR | 20-0367882 | 11/2004 |
| KR | 20-0400568 | 8/2005 |
| KR | 10-0598627 | 7/2006 |
| KR | 10-0953398 | 4/2010 |
| KR | 10-2010-0111031 | 10/2010 |
| KR | 10-1025134 B1 | 3/2011 |
| KR | 10-1028468 | 4/2011 |
| KR | 10-1053551 | 7/2011 |
| WO | WO 94/27456 | 12/1994 |
| WO | WO 95/11602 | 5/1995 |
| WO | WO 95/03720 | 9/1995 |
| WO | WO 98/33408 | 8/1998 |
| WO | WO 98/37782 | 9/1998 |
| WO | WO 99/09850 | 3/1999 |
| WO | WO 99/15043 | 4/1999 |
| WO | WO 99/43231 | 9/1999 |
| WO | WO 00/53045 | 9/2000 |
| WO | WO 00/76337 A1 | 12/2000 |
| WO | WO 01/08525 | 2/2001 |
| WO | WO 01/15559 | 3/2001 |
| WO | WO 02/051511 | 7/2002 |
| WO | WO 2004/093569 | 11/2004 |
| WO | WO 2005/013748 A1 | 2/2005 |
| WO | WO/2007/016983 | 2/2007 |
| WO | WO 2008/015214 | 2/2008 |
| WO | WO/2008/033963 | 3/2008 |
| WO | WO/2009/134858 | 11/2009 |
| WO | WO 2010/059989 A2 | 5/2010 |
| WO | WO 2012/165803 A2 | 12/2012 |
| WO | WO 2013/025704 A1 | 2/2013 |
| WO | WO 2014/036371 A1 | 3/2014 |
| WO | 2014/074645 | 5/2014 |

(56) References Cited

FOREIGN PATENT DOCUMENTS

| WO | WO/2015/035885 | 3/2015 |
| WO | WO 2015/179332 A1 | 11/2015 |
| WO | WO 2015/181928 A1 | 12/2015 |

OTHER PUBLICATIONS

U.S. Appl. No. 09/956,601, filed Sep. 18, 2001, Hammerslag.
ASOLO® Boot Brochure Catalog upon information and belief date is as early as Aug. 22, 1997, 12 pages.
La Sportiva, A Technical Lightweight Double Boot for Cold Environments, 1 page. Accessed on May 27, 2015. Retrieved from http://www.sportiva.com/products/footwear/mountain/spantik.
"Strength of materials used to make my Safety Harnesses," Elaine, Inc. Jul. 9, 2012. Retrieved from <https://web.archive.org/web/20120709002720/http://www.childharness.ca/strength_data.html> on Mar. 17, 2014, 2 pages.
International Search Report and Written Opinion for PCT/US2013/032326 dated Jun. 14, 2013, 27 pages.
International Preliminary Report on Patentability for PCT/US2013/032326 dated Sep. 16, 2014, 6 pages.
International Search Report and Written Opinion for PCT/US2013/057637 dated Apr. 7, 2014, 34 pages.
International Preliminary Report on Patentability for PCT/US2013/057637 dated Mar. 3, 2015, 9 pages.
International Search Report and Written Opinion for PCT/US2013/068342 dated Apr. 7, 2014, 29 pages.
International Preliminary Report on Patentability for PCT/US2013/068342 dated May 5, 2015, 9 pages.
International Search Report and Written Opinion for PCT/US2014/014952 dated Apr. 25, 2014, 17 pages.
International Preliminary Report on Patentability for PCT/US2014/014952 dated Aug. 11, 2015, 9 pages.
International Search Report and Written Opinion for PCT/US2014/066212 dated Apr. 22, 2015, 16 pages.
International Search Report and Written Opinion for PCT/US2014/032574 dated Oct. 31, 2014, 19 pages.
International Search Report and Written Opinion for PCT/US2014/045291 dated Nov. 6, 2014, 12 pages.
International Search Report and Written Opinion for PCT/US2014/013458 dated May 19, 2014, 12 pages.
International Preliminary Report on Patentability for PCT/US2014/013458 dated Jul. 28, 2015, 7 pages.
International Search Report and Witten Opinion for PCT/US2013/068814 dated Jun. 9, 2014, 18 pages.
International Preliminary Report on Patentability for PCT/US2013/068814 dated May 12, 2015, 12 pages.
Notice of Reasons for Rejection from the Japanese Patent Office dated Feb. 26, 2015 for design application No. 2014-015570, 4 pages.
Receipt of Certificate of Design Registration No. 1529678 from the Japanese Patent Office for design application No. 2014-015570 dated Jun. 26, 2015, 1 page.
International Search Report and Written Opinion for PCT/US2014/055710 dated Jul. 6, 2015, 19 pages.
International Search Report and Written Opinion for PCT/US2014/054420 dated Jul. 6, 2015, 21 pages.
The Preliminary Rejections from the Korean Intellectual Property Office for Application No. 30-2014-34959 dated Aug. 7, 2015, is not translated into English. The document requests a renaming of the application to be in accordance with Korean patent law, 5 pages total.
The Preliminary Rejections from the Korean Intellectual Property Office for Application No. 30-2014-34959 dated Apr. 7, 2015, is not translated into English. The document requests a revision of the drawings to be in accordance with Korean patent law, 6 pages total.
Certificate of Design Registration No. 30-809409 dated Aug. 3, 2015 from the Korean Intellectual Property Office for Appln No. 30-2015-11475, 2 pages.
Certificate of Design Registration No. 30-809410 dated Aug. 3, 2015 from the Korean Intellectual Property Office for Appln No. 30-2015-11476, 2 pages.
European Search Report for EP 14168875 dated Oct. 29, 2014, 9 pages.
International Search Report and Written Opinion for PCT/US2014/020894 dated Jun. 20, 2014, 12 pages.
International Preliminary Report on Patentability for PCT/US2014/020894 dated Sep. 8, 2015, 7 pages.
International Search Report and Written Opinion for PCT/US2014/041144 dated Dec. 10, 2014, 13 pages.
International Preliminary Report on Patentability for PCT/US2014/032574 dated Oct. 6, 2015, 12 pages.
International Search Report and Written Opinion for PCT/US2014/046238 dated Nov. 21, 2014, 17 pages.
Office Action dated Oct. 8, 2015 from the German Patent and Trademark Office for Appln No. 402015100191.2, regarding the title of the invention, 2 pages.
Anonymous, "Shore durometer," Wkipedia, the free encyclopedia, Mar. 10, 2012, XP002747470, Retrieved from the Internet: URL: https://en.wikipedia.org/w/index.php?title=Shore_durometer&oldid=481128180 [retrieved on Oct. 20, 2015] * shore A, shore D, durometer, polymer, rubber, gel; the whole document *, 6 pages.
Notice of Reasons for Rejection from the Japanese Patent Office dated Oct. 5, 2015 for design application No. 2015-004923, 4 pages.
"Save Tourniquet," 3 pages. Copyright 2015. Accessed on Dec. 11, 2015. Retrieved from http://www.savetourniquet.com/.
International Preliminary Report on Patentability for PCT/US2014/041144 dated Dec. 8, 2015, all pages.
Supplementary European Search Report for EP 13761841 dated Oct. 21, 2015, all pages.
International Preliminary Report on Patentability for PCT/US2014/066212 dated May 24, 2016, all pages.
International Preliminary Report on Patentability for PCT/US2014/045291 dated Jan. 5, 2016, 5 pages.
International Preliminary Report on Patentability for PCT/US2014/046238 dated Jan. 12, 2016, 11 pages.
International Preliminary Report on Patentability for PCT/US2014/054420 dated Mar. 8, 2016, all pages.
International Search Report and Written Opinion for PCT/US2015/054530 dated Jan. 13, 2016, all pages.

* cited by examiner

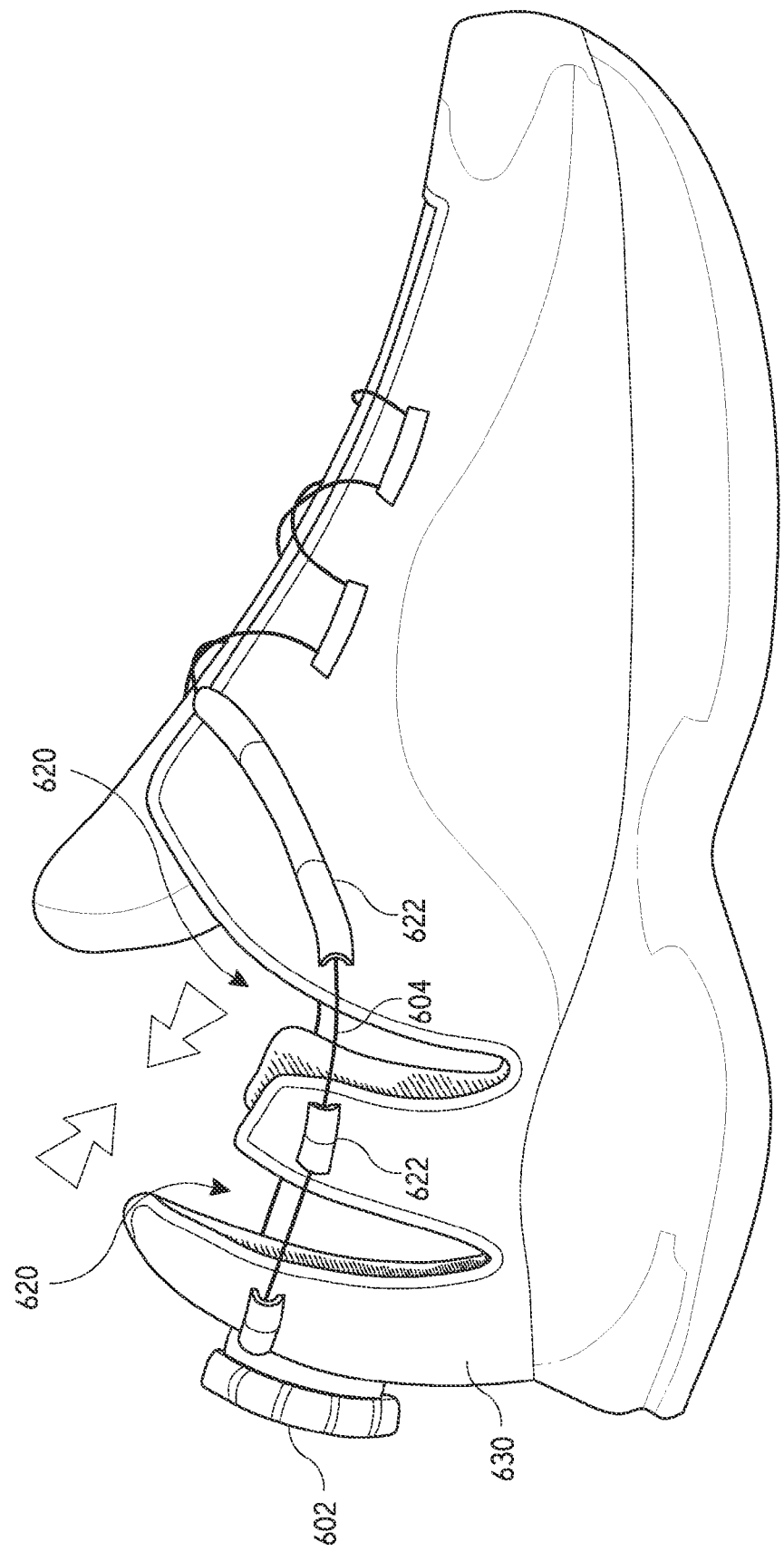

DEVICES AND METHODS FOR ADJUSTING THE FIT OF FOOTWEAR

CROSS-REFERENCES TO RELATED APPLICATIONS

This application claims priority to Provisional U.S. Patent Application No. 61/723,218 filed Nov. 6, 2012, entitled "Running Shoe and Other Devices," the entire disclosure of which is hereby incorporated by reference, for all purposes, as if fully set forth herein.

BACKGROUND OF THE INVENTION

The present invention is related to closure devices for various articles, such as braces, medical devices, shoes, clothing, apparel, and the like. Such articles typically include closure devices that allow the article to be placed and closed about a body part. The closure devices are typically also used to maintain or secure the article to the body part. For example, shoes are typically placed over an individual's foot and lace is tensioned and tied to close the shoe about the foot and secure the shoe to the foot. Conventional closure devices have been modified in an effort to increase the fit and/or comfort of the article about the body part. For example, shoe lacing configurations and/or patterns have been modified in an attempt to increase the fit and/or comfort of wearing shoes. Conventional closure devices have also been modified in an effort to decrease the time in which an article may be closed and secured about the body part. These modifications have resulted in the use of various pull cords, straps, and tensioning devices that enable the article to be quickly closed and secured to the foot.

BRIEF SUMMARY OF THE INVENTION

The present invention generally provides improved closure devices that may be used for closure of various articles, such as braces, medical devices, shoes, clothing, apparel, and the like. In some embodiments, a zonal tightening device or system for tightening an article is provided. In a specific embodiment, the article may be a shoe.

According to one aspect, the zonal tightening device/system includes a plurality of first guide members that are coupled with the article and that define a first zone of the article. A plurality of second guide members are also coupled with the article and define a second zone of the article. At least a portion of the second zone is different than the first zone. A first tension member, such as lace, is guided by the plurality of first guide members within the first zone. The first tension member is configured to tighten the first zone of the article upon tensioning of the first tension member. A second tension member is guided by the plurality of second guide members within the second zone. The second tension member is configured to tighten the second zone of the article upon tensioning of the second tension member. A tensioning mechanism is also coupled with the article and with the first tension member and the second tension member. The tensioning mechanism is configured to differentially tension the first and second tension members so as to differentially tighten the first and second zones of the article. In some embodiments, the tensioning mechanism may be a reel assembly as described herein.

In some embodiments, a proximal end of the first tension member or the second tension member is coupled with the tensioning mechanism and a distal end of the first tension member or the second tension member is coupled with, or terminates on, the article. In such embodiments, the distal end of the first tension member or the second tension member may be adjustable relative to the article to vary the differential tension applied to the respective tension member and zone.

In some embodiments, the device/system may also include an adjustment mechanism that is coupled with the first tension member and the second tension member. The adjustment mechanism may be configured to vary a length of the first tension member and the second tension member within the respective zones to vary the differential tightness applied to the respective tension members. In such embodiments, the adjustment mechanism may be configured to decrease the length of one of the tension members within the respective zone and to increase the length of the other tension member within the respective zone by a corresponding amount.

According to another aspect, the zonal tightening device/system includes a first guide member that is coupled with the article and positioned within a first zone of the article. A second guide member is also coupled with the article and positioned within a second zone of the article. At least a portion of the second zone is different than the first zone. A first tension member is guided by the first guide member within the first zone and a second tension member guided by the second guide member within the second zone. Tensioning of the first tension member causes tightening of the first zone of the article while tensioning of the second tension member causes tightening of the second zone of the article. A tensioning mechanism is coupled with the article and with the first tension member and the second tension member. The tensioning mechanism is configured to tension the first and second tension members to tighten the first and second zones.

In some embodiments, the tensioning mechanism causes a differential tension to be applied to the first tension member and the second tension member to differentially tighten the first and second zones. In such embodiments, the tensioning mechanism may include a spool having a first portion around which the first tension member is wound and a second portion around which the second tension member is wound. A diameter of the first portion may be different than a diameter of the second portion so that winding of the first and second tension members around the spool causes the differential tension to be applied to the first and second tension members.

In other embodiments, the tensioning mechanism may include a spool having the above mentioned first portion and second portion with the first portion including a first channel for the first tension member and the second portion including a second channel for the second tension member. The first channel may be separate from the second channel to prevent tangling of the first and second tension members. In some embodiments, the tensioning mechanism may include a first spool around which the first tension member is wound and a second spool around which the second tension member is wound. A gear or clutch mechanism of the tensioning mechanism may cause rotation of the first and second spools at different rates to cause the differential tension to be applied to the first and second tension members.

In some embodiments, a proximal end of the first tension member may be coupled with the tensioning mechanism and a distal end of the first tension member may be coupled with the article or with a second guide member positioned within the first zone. In such embodiments, a proximal end of the second tension member may likewise be coupled with the tensioning mechanism and a distal end of the second tension member may likewise be coupled with the article or with a second guide member positioned within the second zone. The distal end of the first tension member may be adjustable relative to the article to vary a length of the first tension member within the first zone and/or the distal end of the first tension member may include a tab that is graspable by a user to enable the user to adjust the distal end of the first tension member relative to the article.

In some embodiments, the device/system may also include an adjustment mechanism that is coupled with the first and second tension members. The adjustment mechanism may be configured to vary a length of the first and second tension members within the respective zones to vary the differential tightness applied to the respective zones by the first and second tension members. In some embodiments, the tensioning mechanism may include the adjustment mechanism while in other embodiments the adjustment mechanism may be coupled with the article and separate from the tensioning mechanism. In such embodiments, the adjustment mechanism may be adjacent the first and/or second zones. The adjustment mechanism may be configured to decrease the length of one of the tension members within the respective zone and to increase the length of the other tension member within the respective zone by a corresponding amount.

According to another aspect, a method for coupling a lacing system to an article is provided. The method includes coupling a first guide member with the article with the first guide member positioned within a first zone of the article. A second guide member is also coupled with the article with the second guide member positioned within a second zone of the article. At least a portion of the second zone is different than the first zone. A tensioning mechanism is also coupled with the article. The tensioning mechanism is configured to tension a first tension member and to tension a second tension member. The first tension member is coupled with the tensioning mechanism so that the first tension member is guided by the first guide member within the first zone and so that tensioning of the first tension member causes tightening of the first zone. The second tension member is also coupled with the tensioning mechanism so that the second tension member is guided by the second guide member within the second zone and so that tensioning of the second tension member causes tightening of the second zone.

In some embodiments, the tensioning mechanism is configured to differentially tension the first tension member and the second tension member to differentially tighten the first and second zones. In some embodiments, coupling the first tension member with the tensioning mechanism includes coupling a proximal end of the first tension member with a first portion of a spool and coupling the second tension member with the tensioning mechanism likewise includes coupling a proximal end of the second tension member with a second portion of the spool. In such embodiments, a diameter of the first portion of the spool may be different than a diameter of the second portion of the spool so that winding of the first and second tension members around the spool causes the differential tension to be applied to the first and second tension members.

In some embodiments, a distal end of the first tension member may be coupled with the article or with a second guide member that is positioned within the first zone. In such embodiments, a distal end of the second tension member may likewise be coupled with the article or with a second guide member that is positioned within the second zone. In such embodiments, the distal end of the first tension member may be adjusted relative to the article to vary a length of the first tension member within the first zone. The distal end of the first tension member may include a grippable tab that enables adjustment of the first tension member relative to the article.

In some embodiments, the first and second tension members may be coupled with an adjustment mechanism. The adjustment mechanism may be configured to vary a length of the first and second tension members within the respective zones to vary the differential tension applied to the first and second tension members. In such embodiments, coupling the first and second tension members with the adjustment mechanism may include coupling a distal end of the first and second tension members with the adjustment mechanism. The adjustment mechanism may be configured to decrease the length of one of the tension members within the respective zone and to increase the length of the other tension member within the respective zone by a corresponding amount.

In another embodiment, a torsion bar or drive shaft type device or system for tightening an article is provided. In a specific embodiment, the article may be a shoe. According to one aspect, the device/system includes a tensioning mechanism that is operable to adjust a tightness of the article, a rod that extends longitudinally along at least a portion of the article, and a first tension member that extends laterally from the rod across an opening of the article. The rod has a proximal end operationally coupled with the tensioning mechanism and a distal end coupled with the article. The first tension member has a proximal end coupled with the rod and a distal end coupled with the article. Operation of the tensioning mechanism causes rotation of the rod about the article to adjust a tension of the first tension member and thereby adjust the tightness of the article.

In some embodiments, the proximal end of the first tension member may be adjustable relative to the rod to vary a length of the first tension member available for tightening the article. In other embodiments, the distal end of the first tension member may be adjustable relative to the article to vary a length of the first tension member available for tightening the article.

In some embodiments, adjusting the tension of the first tension member adjusts the tightness of a first zone of the article. In such embodiments, the device/system may also include a second tension member that extends laterally from the rod and across the opening of the article. The second tension member may have a proximal end that is coupled with the rod and a distal end that is coupled with the article. Rotation of the rod may adjust a tension of the second tension member and thereby adjust the tightness of a second zone of the article. The first and/or second tension members may be coupled with the rod so as to be windable around the rod. Rotation of the rod may wind approximately an equal length of the first and second tension members around the rod, or unwind approximately an equal length of the tension members therefrom.

In some embodiments, coupling the first and/or second tension members with the rod may include inserting the proximal end of the first tension member within a first slot of the rod and inserting the proximal end of the second tension member with a second slot of the rod. In some embodiments, a length of the first tension member available for tightening the first zone and/or a length of the second tension member available for tightening the second zone may be adjustable to vary the tightness applied to the first and/or second zones.

According to another aspect, a method for coupling a lacing system to an article is provided. The method includes coupling a tensioning mechanism with the article where the tensioning mechanism is operable to adjust a tightness of the article. A rod is also coupled with the article so that the rod extends longitudinally along at least a portion of the article and so that the rod has a proximal end that operationally couples with the tensioning mechanism and a distal end that couples with the article. A proximal end of a first tension member is coupled with the rod and a distal end of the first tension member is coupled with the article so that the first tension member extends laterally from the rod and across an opening of the article. The rod is coupled with the tensioning mechanism so that operation of the tensioning mechanism causes rotation of the rod about the article to adjust a tension of the first tension member and thereby adjust the tightness of the article.

In some embodiments, the proximal end of the first tension member may be adjusted relative to the rod to vary a length of the first tension member available for tightening the article. In other embodiments, the distal end of the first tension member may be adjusted relative to the article to vary a length of the first tension member available for tightening the article.

In some embodiments, adjusting the tension of the first tension member may adjust the tightness of a first zone of the article. In such embodiments, a proximal end of a second tension member may be coupled with the rod and a distal end of the second tension member with the article so that the second tension member extends laterally from the rod and across the opening of the article. Rotation of the rod may adjust a tension of the second tension member and thereby adjusts the tightness of a second zone of the article. In such embodiments, the first and second tension members may be coupled with the rod by inserting the proximal end of the first tension member within a first slot of the rod and inserting the proximal end of the second tension member with a second slot of the rod. In such embodiments, a length of the first tension member available for tightening the first zone may be adjusted and/or a length of the second tension member available for tightening the second zone may be adjusted in order to vary the tightness applied to the first and second zones. Rotation of the rod may wind approximately an equal length of the first and second tension members around the rod, or may unwind approximately an equal length of the tension members from the rod.

In another embodiment, a unique tubing configuration may be employed to aid in tightening an article. In a specific embodiment, the article may be a shoe. According to one aspect, the unique configuration may be employed in a lacing system that includes a tensioning mechanism and a tension member that is coupled with the tensioning mechanism so as to be tensionable by operation of the tensioning mechanism. A first tubing may be coupled with the article and may extend along at least a portion thereof. The first tubing may include a proximal end, a distal end, and a lumen that extends between the proximal and distal ends. A second tubing may also be coupled with the article and may extend along at least a portion thereof. The second tubing may include a proximal end, a distal end, and a lumen that extends between the proximal and distal ends. The tension member may be disposed within the lumen of the first tubing and the second tubing and a distal end of the second tubing may be slidably positioned within a proximal end of the first tubing's lumen so that tensioning of the tension member causes the second tubing to slide within the first tubing's lumen to allow adjustment of the tightness of the article adjacent the first and second tubing.

In some embodiments, the first and second tubing may be positioned around a heel or collar portion of a shoe. In some embodiments, at least a portion of the proximal end of the first tubing's lumen may be transparent so that sliding of the second tubing within the first tubing's lumen is viewable to a user. In some embodiments, the distal end of the second tubing and the proximal end of the first tubing may be uncoupled from the article (e.g., shoe) so that buckling of the article's material is reduced or prevented as the second tubing slides within the first tubing's lumen. In another embodiment, the distal end of the second tubing and the proximal end of the first tubing may be coupled with a flexible material so that buckling of the article is reduced or prevented as the second tubing slides within the first tubing's lumen.

In some embodiments, sliding of the second tubing within the first tubing's lumen adjusts the tightness of the article via compression of the first and second tubing about a body of the article. In some embodiments, the lumen of the first tubing includes a stop component that limits sliding of the second tubing within the first tubing's lumen. In some embodiments, a third tubing may be coupled with the article and may extend along at least a portion thereof. The third tubing may include a proximal end, a distal end, and a lumen that extends between the proximal and distal ends. The tension member may be disposed within the lumen of the third tubing and a distal end of the third tubing may be slidably positioned within the lumen of the first tubing or second tubing so that tensioning of the tension member causes the third tubing to slide within the lumen of the first or second tubing.

According to one aspect, a method for coupling a lacing system to an article is provided. The lacing system includes the unique tubing configuration. The method includes coupling a tensioning mechanism with the article and coupling a first tubing with the article so that the first tubing extends along at least a portion of the article. The first tubing has a proximal end, a distal end, and a lumen that extends between the proximal and distal ends. A second tubing is also coupled with the article so that the second tubing extends along at least a portion of the article. The second tubing has a proximal end, a distal end, and a lumen that extends between the proximal and distal ends. A distal end of the second tubing is inserted within a proximal end of the first tubing's lumen so that the distal end of the second tubing is slidably disposed within the proximal end of the first tubing's lumen. A tension member is inserted within the lumens of the first tubing and the second tubing and the tension member is coupled with the tensioning mechanism so that the tension member is tensionable by operation of the tensioning mechanism. Tensioning of the tension member causes the second tubing to slide within the first tubing's lumen in order to adjust the tightness of the article.

In some embodiments, a third tubing is also coupled with the article so that the third tubing extends along at least a portion of the article. The third tubing has a proximal end, a distal end, and a lumen that extends between the proximal and distal ends. In such embodiments, a distal end of the third tubing may be inserted within the lumen of the first tubing or second tubing so that the distal end of the second tubing is slidably disposed within the lumen of the first tubing or second tubing. The tension member may also be inserted within the lumen of the third tubing. Tensioning of the tension member may cause the third tubing to slide within the lumen of the first or second tubing.

BRIEF DESCRIPTION OF THE DRAWINGS

The present invention is described in conjunction with the appended figures.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

Embodiments described herein provide various features for closure devices that may be used to close a variety of items, such as medical braces (i.e., back braces, knee braces, and the like), items of clothing (i.e., hats, gloves, and the like), sports apparel (boots, snowboard boots, ski boots, and the like), and various other items. A specific embodiment in which the closure devices may be used involves shoes, and specifically running shoes. For ease in describing the embodiments herein, the disclosure will mainly describe the closure device being used for shoes or running shoes, although it should be realized that the closure devices may be used for the various other items.

Referring now to FIGS. 1-4, provided is a general description of a tensioning mechanism or reel assembly (hereinafter reel assembly) of a lacing system. The illustrated reel assembly includes a knob that may be grasped and rotated by a user to tension lace that is wound around guides of a shoe. The illustrated reel assembly, however, is only one of many tensioning mechanisms that may be used to tension a tension member, such as lace. Accordingly, other tension mechanisms may be used instead of, or in addition to, the illustrated reel assembly to tension a tension member. For example, various pull cords, clamp devices, and the like may be used instead of or in addition to the illustrated reel assembly. As such, the embodiments described herein are not limited to reel assembly based devices.

Figure 1:
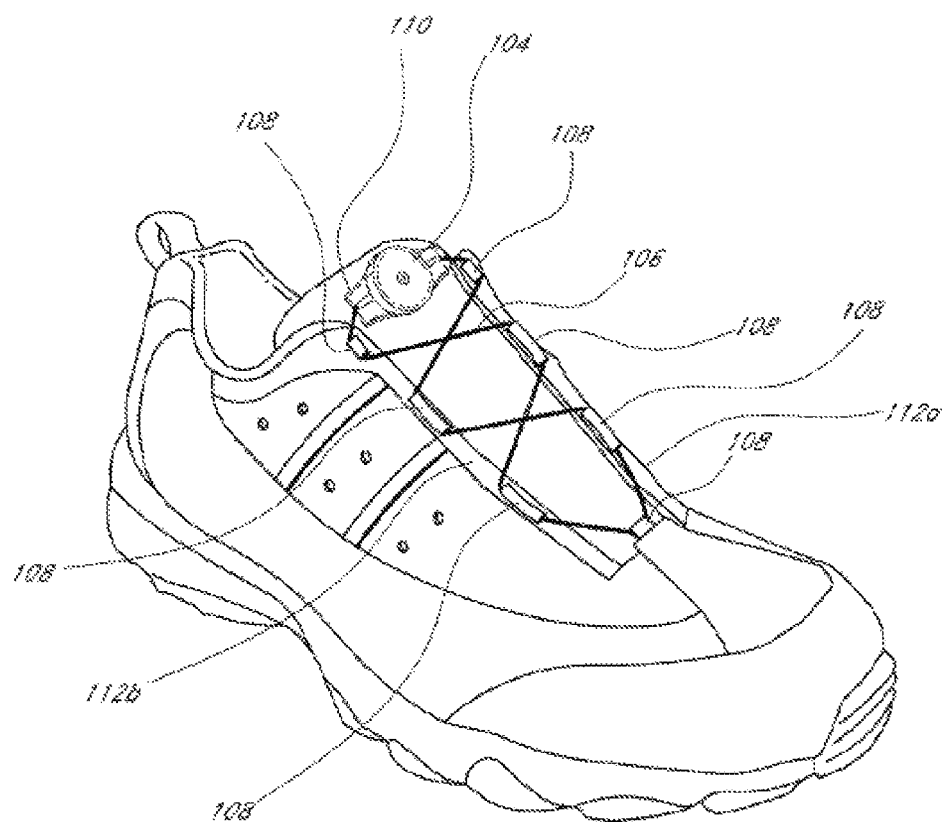
FIGS. 1-4 illustrate embodiments of a closure device being used with a shoe to allow the shoe to be closed about a foot of an individual.

FIG. 1 is a perspective view of an embodiment of lacing system used for tightening a shoe. The shoe can be any suitable footwear that can be tightened around a user's foot. The lacing system can be used to close or tighten various other articles as described herein, such as, for example, a belt, a hat, a glove, snowboard bindings, a medical brace, or a bag. The lacing system can include a reel assembly 104, lace 106, and one or more lace guides 108. In the illustrated embodiment, the reel assembly 104 can be attached to the tongue 110 of the shoe. Various other configurations are also possible. For example, the reel assembly 104 can be attached to a side of the shoe, which can be advantageous for shoes in which the shoe sides 112a-b are designed to be drawn closely together when tightened, leaving only a small portion of the tongue 110 exposed. The reel assembly 104 can also be attached to the back of the shoe, and a portion of the lace 106 can pass through the shoe, sometimes using tubing for the lace to travel through, on either side of the user's ankle such that the lace 106 can be engaged with the reel assembly 104 when back-mounted.

Figure 2:
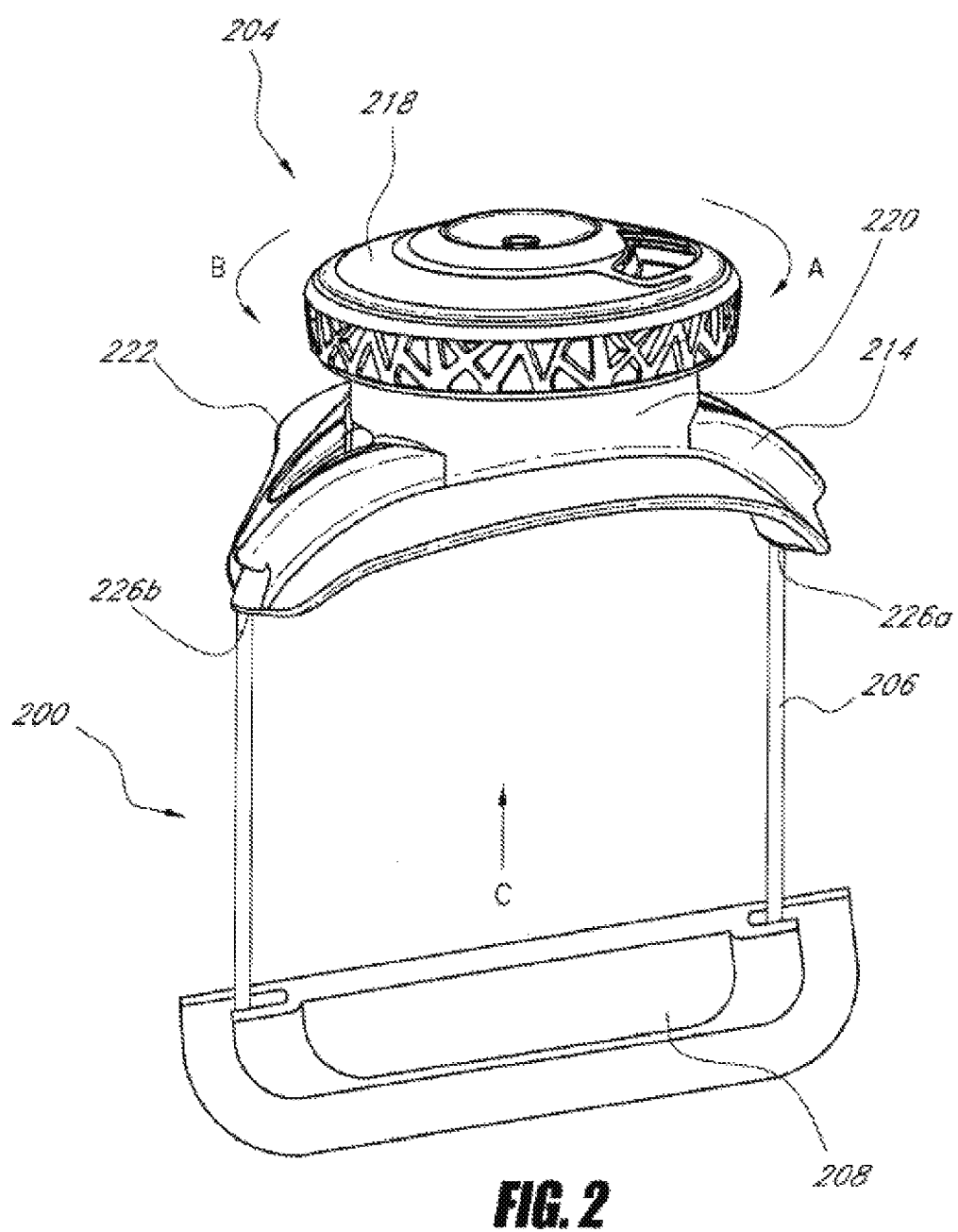
Figure 3:
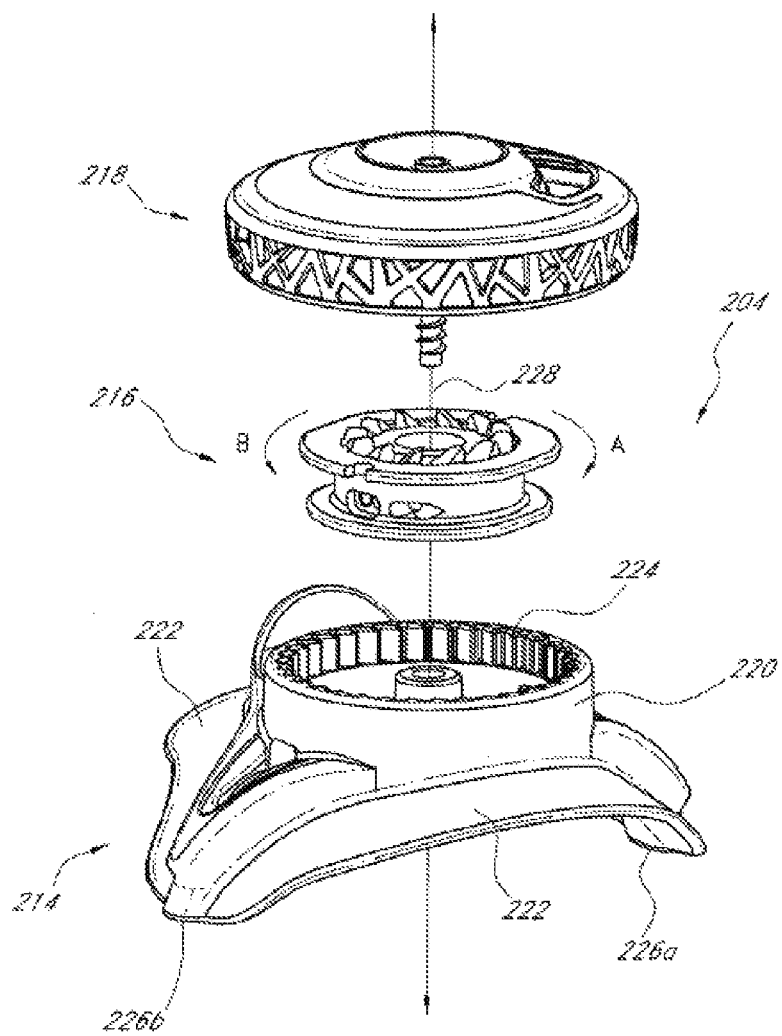
Figure 4:
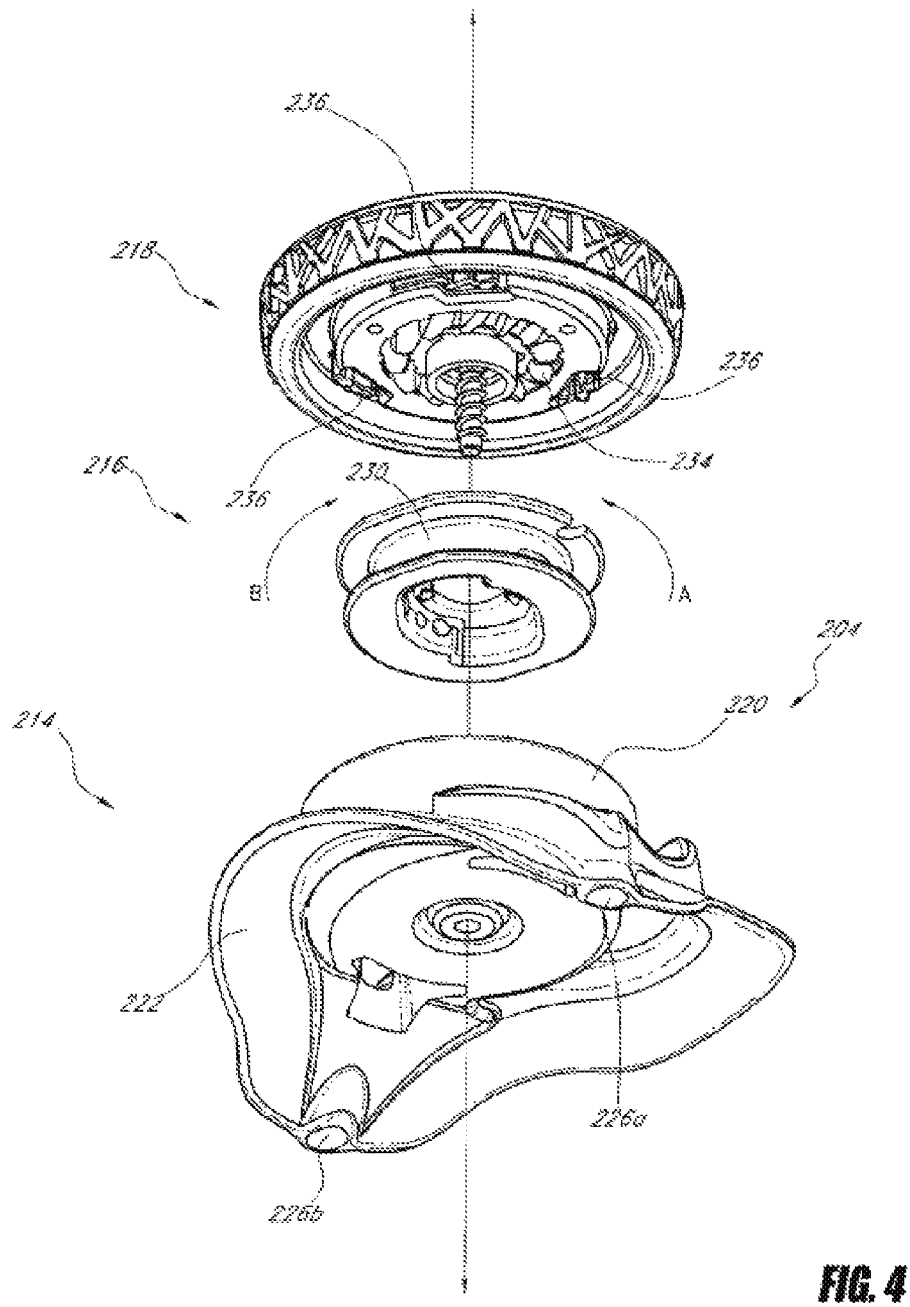

FIG. 2 is a perspective view of an embodiment of a lacing system 200 that can be similar to the lacing system of FIG. 1, or any other lacing system described herein. The lacing system 200 can include a reel assembly 204 which can be similar to reel assembly 104, or any other reel assembly described herein. FIGS. 3 and 4 are exploded perspective views of the reel assembly 204.

With reference to FIGS. 2 to 4, the reel assembly 204 can include a base member 214, a spool member 216, and a knob 218. The base member 214 can include a housing 220 and a mounting flange 222. The housing 220 can include a plurality of housing teeth 224, which can extend radially inwardly. The housing 220 can also include lace holes 226a-b that allow the lace 206 to enter the housing 220.

The spool member 216 can be disposed within the housing 220 such that the spool member 216 is rotatable about an axis 228 with respect to the housing 220. The lace 206 can be secured to the spool member 216 such that when the spool member 216 rotates in a tightening direction (shown by arrow A) the lace 206 is drawn into the housing 220 and is wound around the channel 230 formed in the spool member 216, and when the spool member 216 rotates in a loosening direction (shown by arrow B) the lace 206 unwinds from the channel 230 of the spool member 216 and exits the housing 220 via the lace holes 226a-b. The spool member 216 can also include spool teeth formed thereon. It will be understood that the embodiments disclosed herein can be modified such that rotation in the direction shown by arrow B will tighten the lacing. In this particular embodiment, the knob 218 may be raised axially to disengage the knob 218 from the spool 216 in order to allow the spool to freewheel in direction B in order to release the lace. In other embodiments, rotation of the knob 218 in the direction shown by arrow B may loosen the lacing system.

The knob 218 can be attached to the housing 220 such that the knob 218 can rotate about the axis 228 with respect to the housing 220. The knob 218 can include knob teeth 234 that can be configured to mate with the spool teeth of spool member 216 to couple the knob 218 to the spool member 216 such that rotation of the knob 218 in the tightening direction causes the spool member 216 to also rotate in the tightening direction. In some embodiments, the rotation of the knob 218 in the loosening direction can also cause the spool member 216 to rotate in the loosening direction. The knob 218 can also include one or more pawls 236 which can be biased radially outwardly so as to mate with the housing teeth 224. The pawls 236 and housing teeth 224 can be configured so that the housing teeth 224 can displace the pawls 236 radially inwardly when the knob member 218 is rotated in the tightening direction, thereby allowing the knob member 218 to rotate in the tightening direction. The pawls 236 and the housing teeth 224 can also be configured so that they engage one another when force is applied to twist the knob member 218 in the loosening direction, thereby preventing the knob member 218 from rotating in the loosening direction.

Thus, the reel assembly 204 can provide a one-way tightening system that allows the user to rotate the knob 218 in the tightening direction, which causes the spool member 216 to rotate in the tightening direction, which in turn causes the lace 206 to be drawn into the housing 220 via the lace holes 226a-b. As the lace 206 is drawn into the housing 220 the lacing system 200 can tighten, causing the lace guide 208 to be drawn in the direction toward the reel 204 (shown by arrow C in FIG. 2). Although the lacing system 200 is shown with a single lace guide 208, any other suitable number of lace guides can be used. Other feature of the reel and lacing system are described in U.S. Patent Application No. 2011/0266384, filed Apr. 29, 2011, and Titled "Reel Based Lacing System", the entire disclosure of which is incorporated herein by reference. The embodiments described herein generally describe ways in which a shoe, brace, or other device may be custom or tailor fit to a user.

Heel Hold and Perpendicular Pressure, Displacement, or Force

In one embodiment, the customized fit may be provided by providing a sufficient amount of "hold" or tightening in desired areas of the foot, such as: heel hold, mid-foot fit or hold, saddle fit or hold. In one embodiment, the shoe's "heel hold" may be divided into three categories, specifically: the width of the heel pocket, the Achilles area (i.e., the fit of the shoe about the Achilles), and the adjustability of the ankle or rake of the heel counter. In one embodiment, the heel hold (i.e., the width of the heel pocket, rake of the heel counter, and the like) may be adjusted by providing a compressible or hinging collar that fits about the heel of the shoe. Heel hold may be provided by squeezing the shoe above the calcaneus, preferably on the medial and lateral sides, which squeeze may be achieved via a compressible collar. In some embodiments, lace of a closure system, such as those described in FIGS. 1-4, may be inserted within a shoe's collar in order to apply pressure to the top portion of the heel when the lace is tensioned via reel assembly. In such embodiments, tensioning of the lace will shrink the collar circumference of the shoe around the user's foot.

Figure 5B:
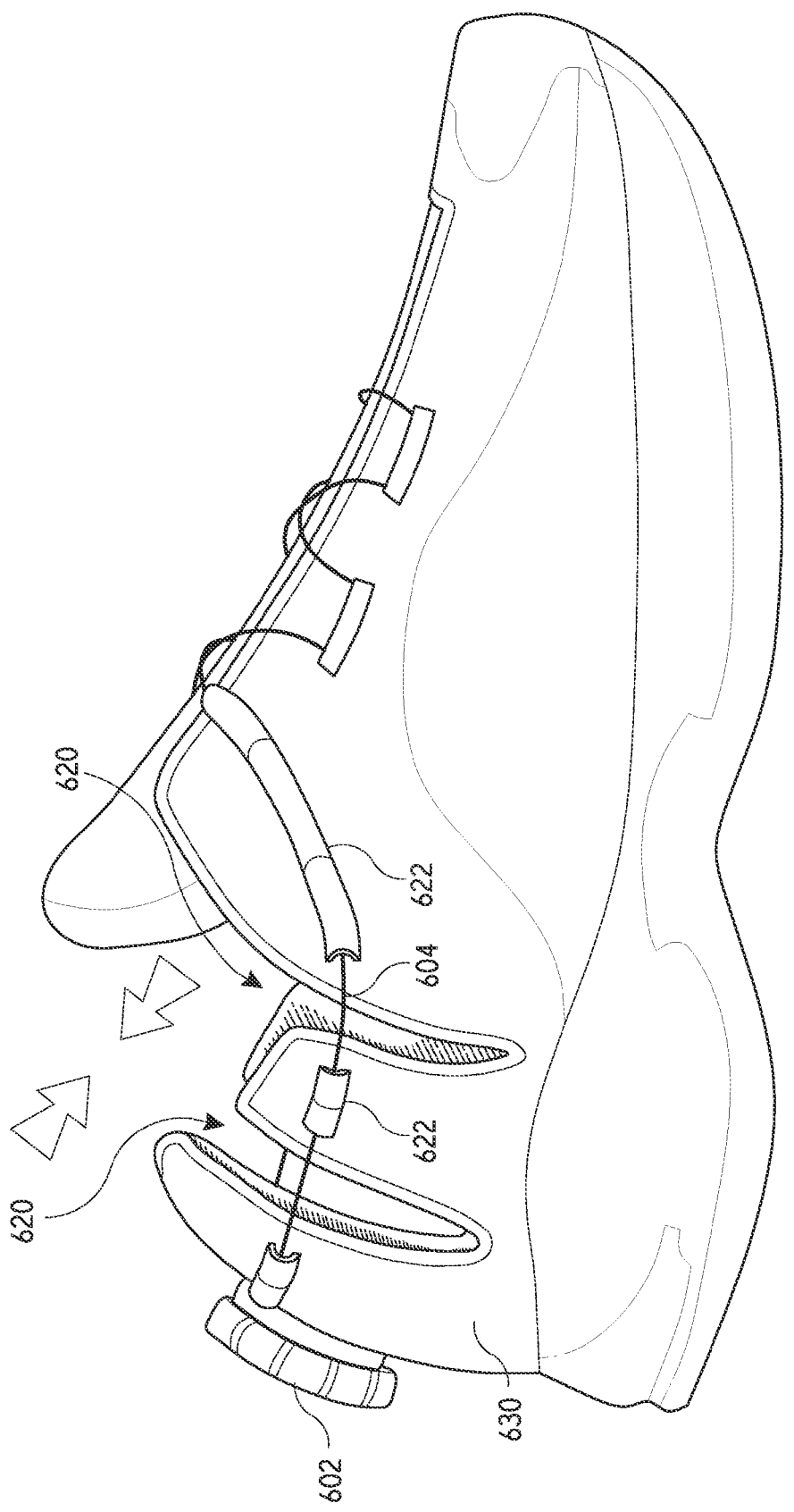
FIGS. 5A-6D illustrate various embodiments of closure devices that may be used to close a heel or collar portion of a shoe.
Figure 6A:
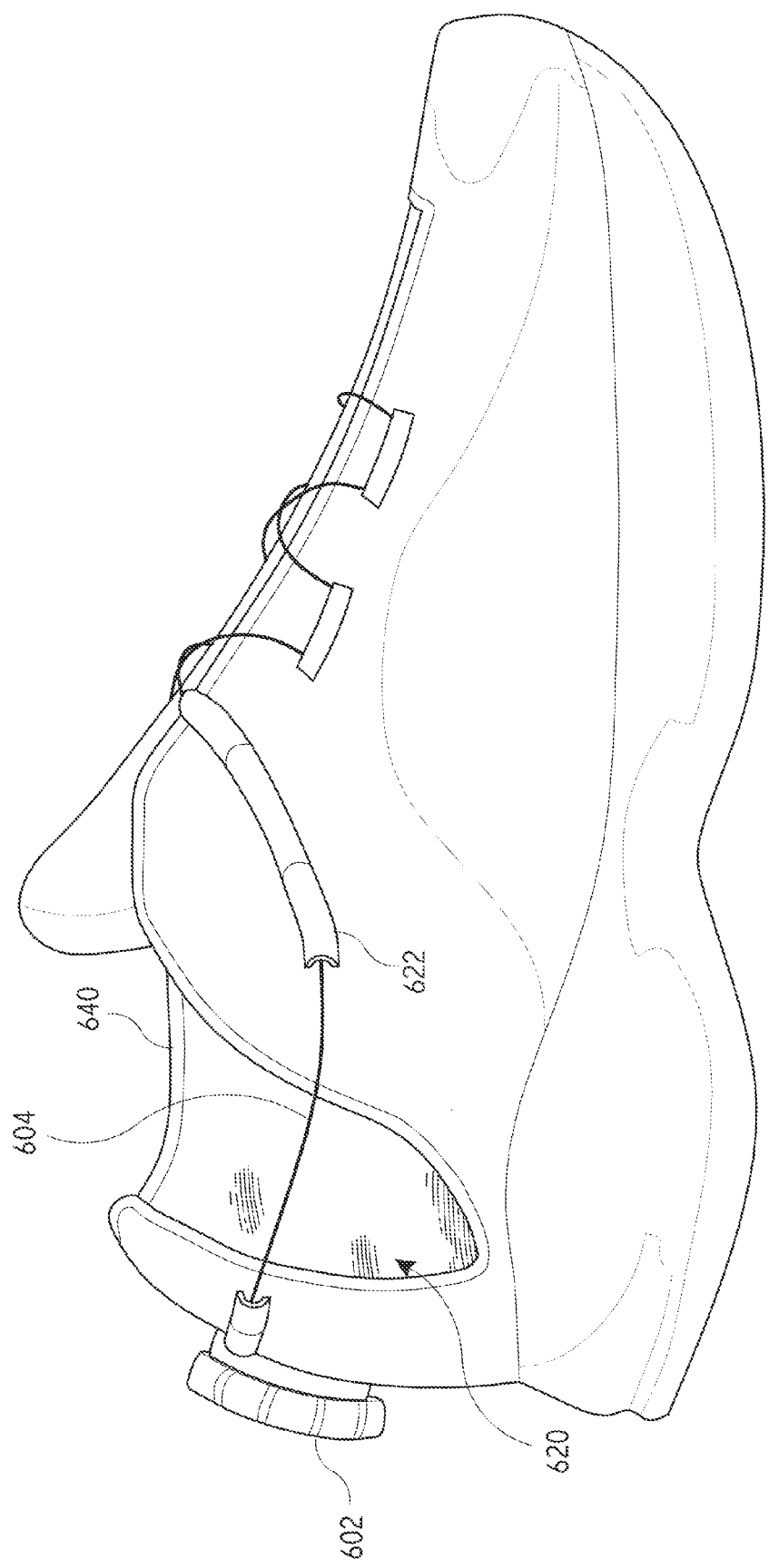

In some embodiments, the amount of perpendicular or closure force applied to the foot may be modified by configuring the shoe with force free and/or compression free regions. For example, as shown in FIGS. 5A and 5B, tubing 622 may be run through or along the shoe and lace 604 inserted through the tubing 622. The tubing 622 may be considered an incompressible solid body that resists compression as the lace 604 is tensioned. In this manner, a force and/or pressure will not be applied or transferred to the foot in regions that are coupled or otherwise include tubing 622 as the lace is tensioned. To create closure or pressure zones, the tubing 622 may be discontinuous, or stated differently have separated tube portions, to create regions or zones 620 where a force or pressure may be applied as the lace 604 is tensioned. For example, as shown in FIGS. 5A and 5B, the shoe 630 may be configured to have one, two, or more force application regions 620 where the tubing 622 is discontinuous or individual tube segments are separated. As the lace 604 is tensioned via reel assembly 602, the shoe's collar is compressed around the user's foot due to regions 620 of discontinuous tubing. The force or pressure may not be applied in regions of the shoe that are coupled with the tubing 622. The embodiment of FIGS. 5A and 5B is an "open design" where the lace 604 spans the open regions 620. In other embodiments, webbing 640 may be attached to the shoe 630 to span the compressible regions 620 as shown in FIG. 6A. The webbing 640 may be a flexible or elastic material that stretches or expands and contracts as the shoe's collar is compressed or constricted about the user's foot. The "open" design of FIGS. 5A and 5B and/or the webbing 640 of FIG. 6A prevent or reduce buckling of the shoe's material as the shoe's collar compresses about the user's foot.

In another embodiment, tubing, or tubing segments, through which the lace is disposed may have compressible regions that allow a compression force to be applied at desired areas along or about the shoe. The compressible regions allow for the application of a force even though the tubing or tubing segments are generally incompressible. As illustrated in FIG. 6C, according to one embodiment the compressible regions may be provided by a "tube in tube" configuration, where a first or inner tubing segment 608a is slidingly inserted within a second or outer tubing segment 608b. Specifically, a distal end of the inner tubing 608a is slidably positioned within a proximal end of a lumen of outer tubing 608b. Lace 604 is disposed within the lumens of inner tubing 608a and outer tubing 608b. The inner and outer tubing, 608a and 608b, are coupled with the shoe and extend along at least a portion thereof, which may be on a side of the shoe's collar, or around the shoe's heel as illustrated in FIG. 6D, and/or elsewhere along the shoe. In some embodiments, the inner and/or outer tubing, 608a and 608b, and/or portions thereof, may be disposed within the outer material layer of the shoe so as to be hidden from view.

As the lace is tensioned, such as via reel assembly 602, the inner tubing 608a slides within the outer tubing 608b and compression is applied to the foot along the tubing segments and/or at the mating location of the tube segments. Compression of the inner tubing 608a and outer tubing 608b about the shoe's collar, or elsewhere relative to the shoe, tightens the shoe about the user's foot. Although not shown, in one embodiment, the outer tubing 608b may have one or more stops that limit sliding of the inner tubing within the outer tubing. In this manner, the amount of compression applied to desired regions of the foot may be more approximately controlled and/or limited. Further, the tubing segments may have multiple compressible areas, such as by having multiple tube-in-tube configurations or locations. Specific compression about the foot may be provided via the arrangement of the compressible regions about the shoe. In some embodiments, the proximal end of the outer tubing 608b and/or inner tubing 608a, or at least a portion thereof, may be transparent so that sliding of the inner tubing 608a within the outer tubing's lumen 608b is viewable to a user.

In some embodiments, the distal end of the inner tubing 608a and the proximal end of the outer tubing 608b may be uncoupled from the shoe so that buckling of the shoe's material is reduced or prevented as the inner tubing 608a slides within the outer tubing's lumen 608b. In other embodiments, the distal end of the inner tubing 608a and the proximal end of the outer tubing 608b may be coupled with a flexible material, such as webbing 640, so that buckling of the article is reduced or prevented as the inner tubing 608a slides within the outer tubing's lumen 608*b*. FIG. 6D illustrates the tube-in-tube configuration positioned around the shoe's collar to apply pressure at the back of the foot and/or at the medial and lateral sides of the foot. It should be realized that various other configurations are possible.

Although not shown in FIGS. 6C and 6D, in some embodiments a third tubing segment may be coupled with the shoe and extend along at least a portion thereof. The lace 604 may be disposed within a lumen of the third tubing segment and a distal end of the third tubing segment may be slidably positioned within the lumen of the inner tubing 608*a* or outer tubing 608*b*. In such embodiments, tensioning of the lace 604 may cause the third tubing to slide within the lumen of the inner or outer tubing, 608*a* or 608*b*.

Related to FIGS. 6C and 6D, a method for coupling a tube-in-tube configuration to a shoe may include coupling a reel assembly with the shoe, coupling a first tubing with the shoe, and coupling a second tubing with the shoe. The first and second tubing may each extend along at least a portion of the shoe, such as around the collar or heel of the shoe. The first and second tubing may also each have a proximal end, a distal end, and a lumen that extends between the proximal and distal ends. The method may also include inserting a distal end of the second tubing within a proximal end of the first tubing's lumen so that the distal end of the second tubing is slidably disposed within the proximal end of the first tubing's lumen. The lacing system's lace may be inserted through, or otherwise disposed within, the lumens of the first tubing and the second tubing. The lace may be coupled with the reel assembly so that the lace is tensionable by operation of the reel assembly. As described herein, tensioning of the lace causes the second tubing to slide within the first tubing's lumen and thereby adjusts the tightness of the shoe about a user's foot. A third tubing could likewise be coupled with the shoe and have a distal end positioned within the lumen of the first or second tubing so that tensioning of the lace causes the third tubing to slide within the first or second tubing's lumen.

Figure 6B:
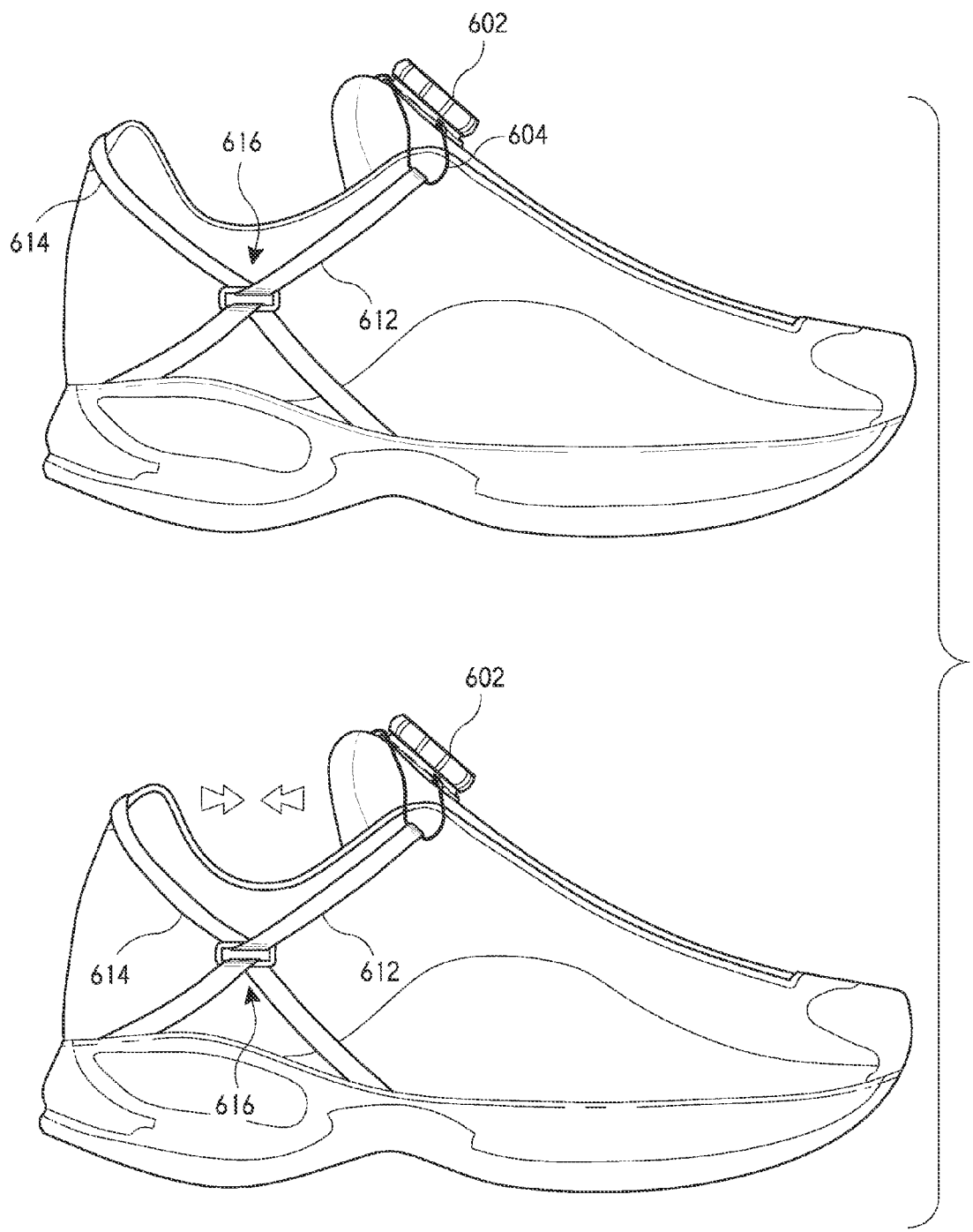
Figure 6C:
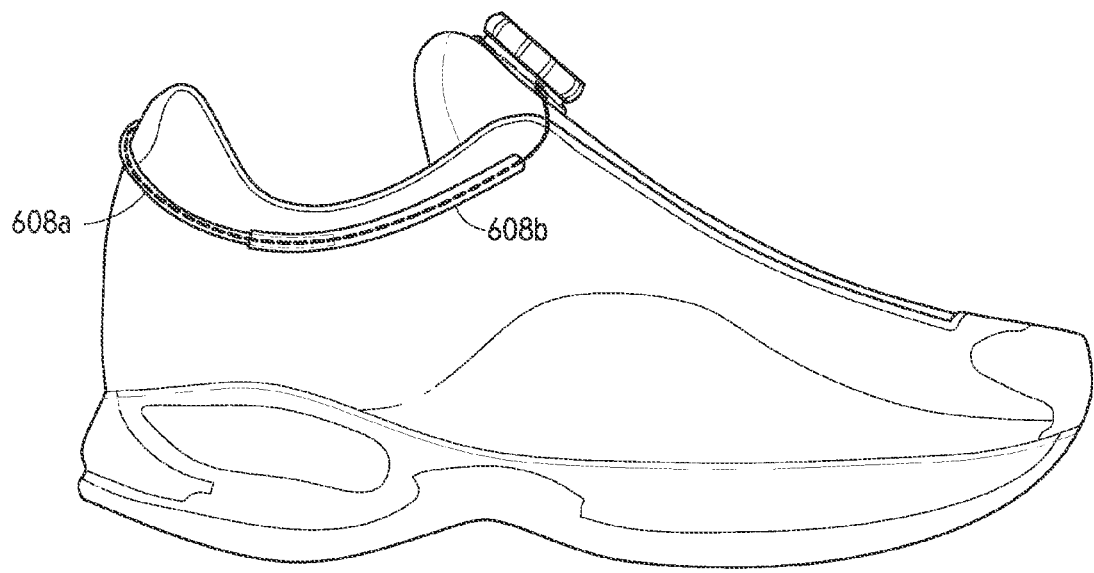
Figure 6D:
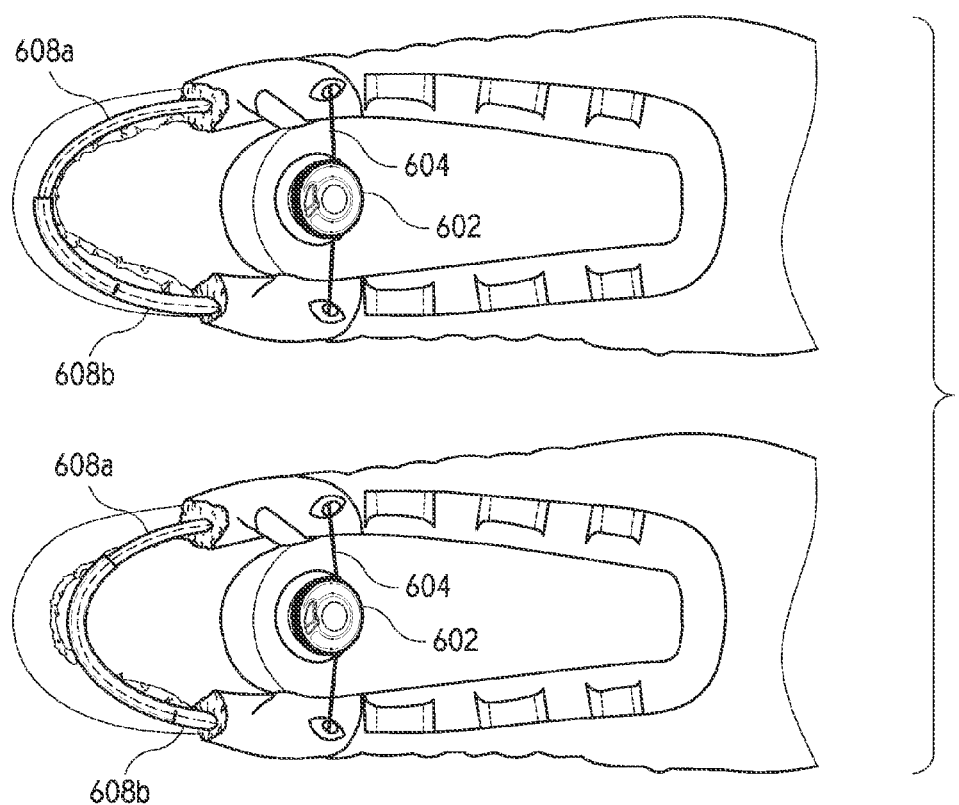

FIG. 6B illustrates another embodiment that may be used to provide heel hold or collar compression. Specifically, webbing may be used to compress the shoe's collar. In the embodiment illustrated, a first webbing segment 614 crosses a second webbing segment 612 at a center point or transition ring 616. As the second webbing segment 612 is tensioned via lace 604 and reel 602, a force is transferred to first and second webbing segments, 614 and 612, that compresses the collar of the shoe about the user's foot.

The compression of the shoe or article against the body surface as provided by the embodiments described herein may also be applied to various medical applications. For example, in one embodiment, the tube-in-tube configuration, webbing segments, and the like may be used in a brace that applies compression to an area of the body, such as in an ankle brace, arm brace, and the like. The provided compression may be part of a therapeutic treatment plan for the body part, such as healing sprains (e.g., ACL, PCL sprains or tears), tears, fractures, bone brakes, and the like. In another embodiment, the compression may be applied with heat or cold, such as by placing an ice or heat pack within the brace and tensioning the lace to compress the area of the body in contact with the ice or heat pack.

Multiple Spool and/or Single Reel Arrangement

Figure 7A:
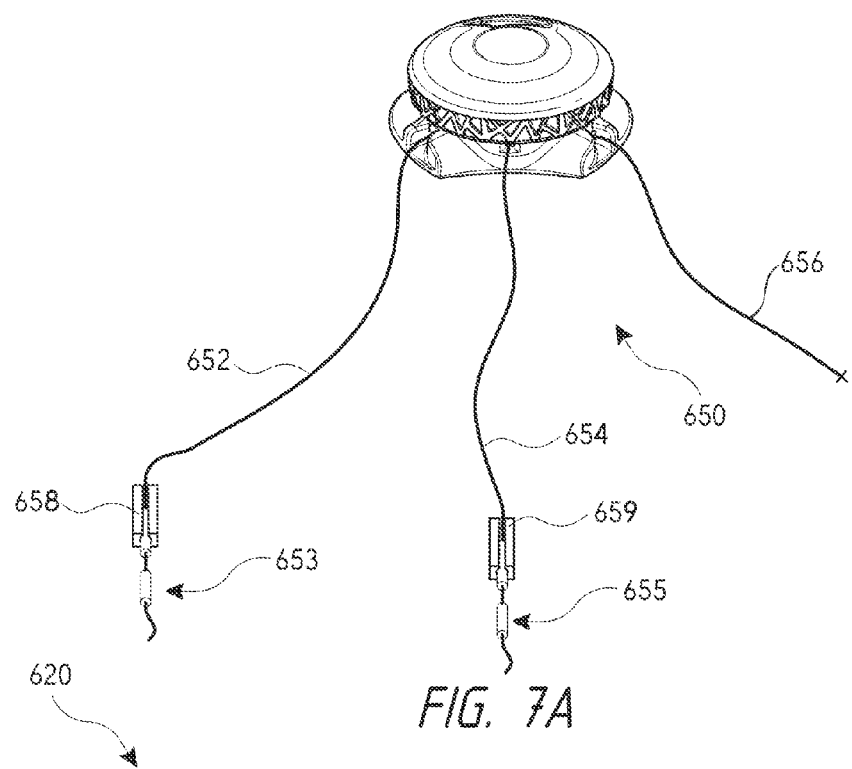
FIGS. 7A-C illustrate various embodiments of closure devices that may be used to zonally tension a shoe.

In another embodiment, a single reel could be provided that drives multiple spool segments and/or winds multiple lace segments. For example, as shown in FIG. 7C, two or more separate spools, 610 and 611, could be positioned adjacent one another and rotated or driven via a single reel assembly 613. Each of the spools, 610 and 611, may include gear teeth that allow the spools to be driven via the single reel assembly 613. In some embodiments, the spools, 610 and 611, could be geared at different ratios so that the spools, 610 and 611, are driven or rotated at different rates by the single reel assembly 613 and thereby differentially tension lace coupled with the spools. In other embodiments, a clutch mechanism could be used to cause differential rotation of the spools, 610 and 611, and thereby differentially tension lace coupled therewith. Differentially tensioning the lace may be performed to differentially or zonally tighten the shoe or other article about the user's foot or body part as described herein.

Figure 7B:
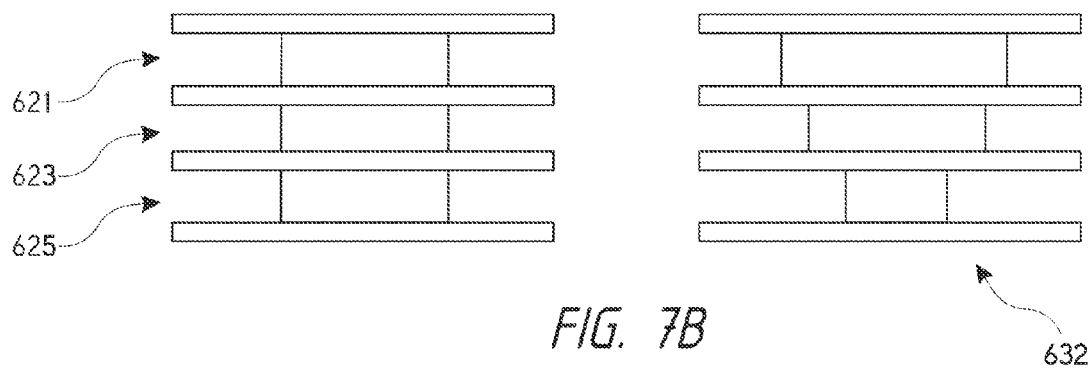
Figure 7C:
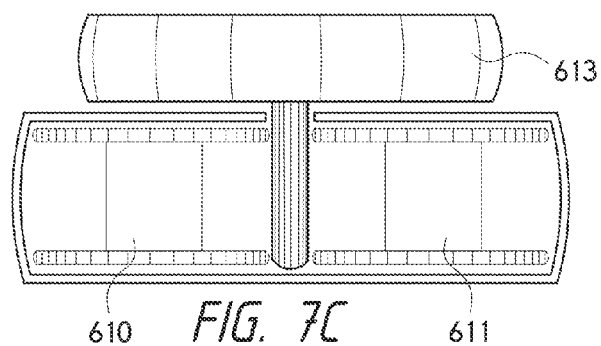

As shown in FIG. 7B, in another embodiment, a spool 620 may have multiple channels that prevent or limit tangling of lace segments coupled therewith. For example, spool 620 may include a first channel of portion 621 around which a first lace is wound (not shown), and may include a second channel or portion 623 and/or third channel or portion 625 around which a second and/or third lace is wound (not shown). The first, second, and/or third channels (621, 623, and/or 625) are separate from one another and divided by a wall or barrier that prevents tangling of the laces coupled therewith. One or more of the channels (621, 623, and/or 625) may have the same diameter central body portions as shown in embodiment 620, or may have different diameter central body portions as shown in embodiment 632. The varying diameter body portions of embodiment 632 allows separate lace segments coupled with the individual channels to be wound or tensioned at different rates. Accordingly, differential tightening and/or zonal adjustment of the shoe or article may be achieved via a single reel assembly. In some embodiments, the lace materials and/or properties used for the different spools and/or channels may be varied to further achieve differential or zonal shoe/article tightening.

As shown in FIG. 7A, the zonal or differential tightening may be further adjusted by adjusting a distal end of the lace. The adjustable lace ends may be especially useful in the zonal tensioning embodiments described in greater detail hereinbelow. FIG. 7A illustrates a tensioning mechanism or reel assembly 650 that is configured to tension a plurality of individual and/or separate lace segments. Specifically, a proximal end of a first lace 652, a second lace 654, a third lace 656, and the like, is coupled with reel assembly 650. Each lace may be coupled with a separate or individual spool, or a lace channel of a spool, such as is illustrated in FIGS. 7B and 7C. A distal end the first lace 652, second lace 654, or third lace 656, or a distal end of each lace may be coupled with the shoe or other article or with a guide member (i.e., 653, 655, and the like) that is positioned within a zone of the shoe or otherwise coupled with the shoe.

In some embodiments, such as the zonal tensioning embodiments described hereinbelow, the first lace 652, the second lace 654, and/or the third lace 656 may each be positioned within separate zones so that tensioning of the laces differentially tensions the separate zones of the shoe or article. The distal ends of the first lace 652, the second lace 654, and/or the third lace 656 are adjustable relative to the shoe/article to vary a length of the respective lace within the respective zone. For example, the lace ends of the first lace 652, the second lace 654, and/or the third lace 656 include components or adjusters, such as cams, snaps, hooks, crimps, knots, and the like, that allow the termination points of the lace ends to be adjusted about the article and thereby vary the length of the respective lace within the respective zone. The components or adjusters may engage with guide member or termination points, 653, 655, and the like, to prevent proximal movement of the lace about the shoe/ article. For example, the cams, snaps, hooks, crimps, knots, and the like, may be positioned within a channel or aperture of the termination points, 653 and 655, to prevent movement of the lace. The lace may be pulled distally of the termination point to shorten the lace length of a respective lace. In some embodiments, the distal end of the laces may include a tab that is graspable by a user to enable the user to adjust the distal end of the first tension member relative to the article.

The embodiments described herein allow the shoe to be custom fit in a relatively quick manner, which allows the user to quickly and conveniently close the shoe over the foot while providing a customized fit. Stated differently, the embodiments described herein enable one type of shoe to fit a wide variety of foot volumes and foot shapes.

In some embodiments, the above described spools could be geared in a vertical or horizontal arrangement, such as by using planetary gears. In one embodiment, multiple spools may be driven at different rates with a planetary intermediary gear that is able to provide varying spool speeds. In other embodiments, the spools could be belt driven, such as by a small cog belt or friction belt (e.g., rubber belt).

Flexible Heel Counter

Figure 8A:
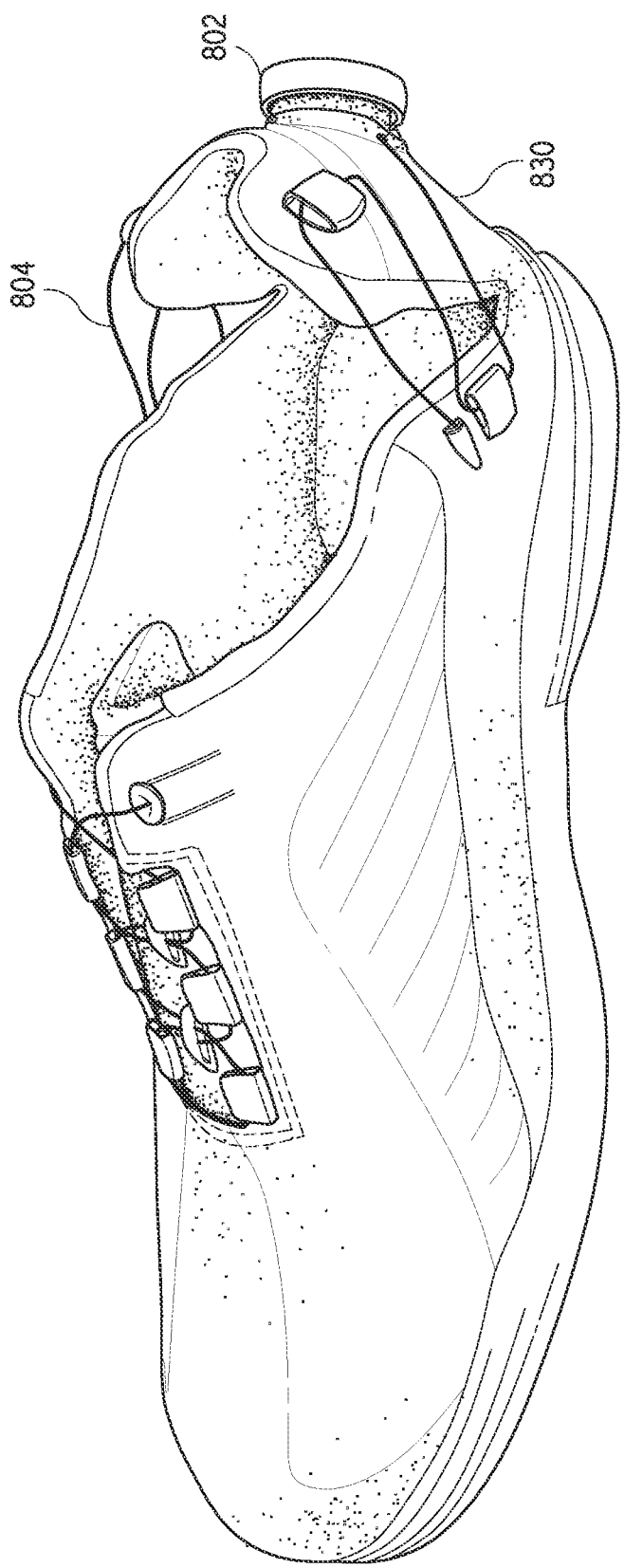
FIGS. 8A and 8B illustrate a closure device being used to pivotally close a heel counter of a shoe.
Figure 8B:
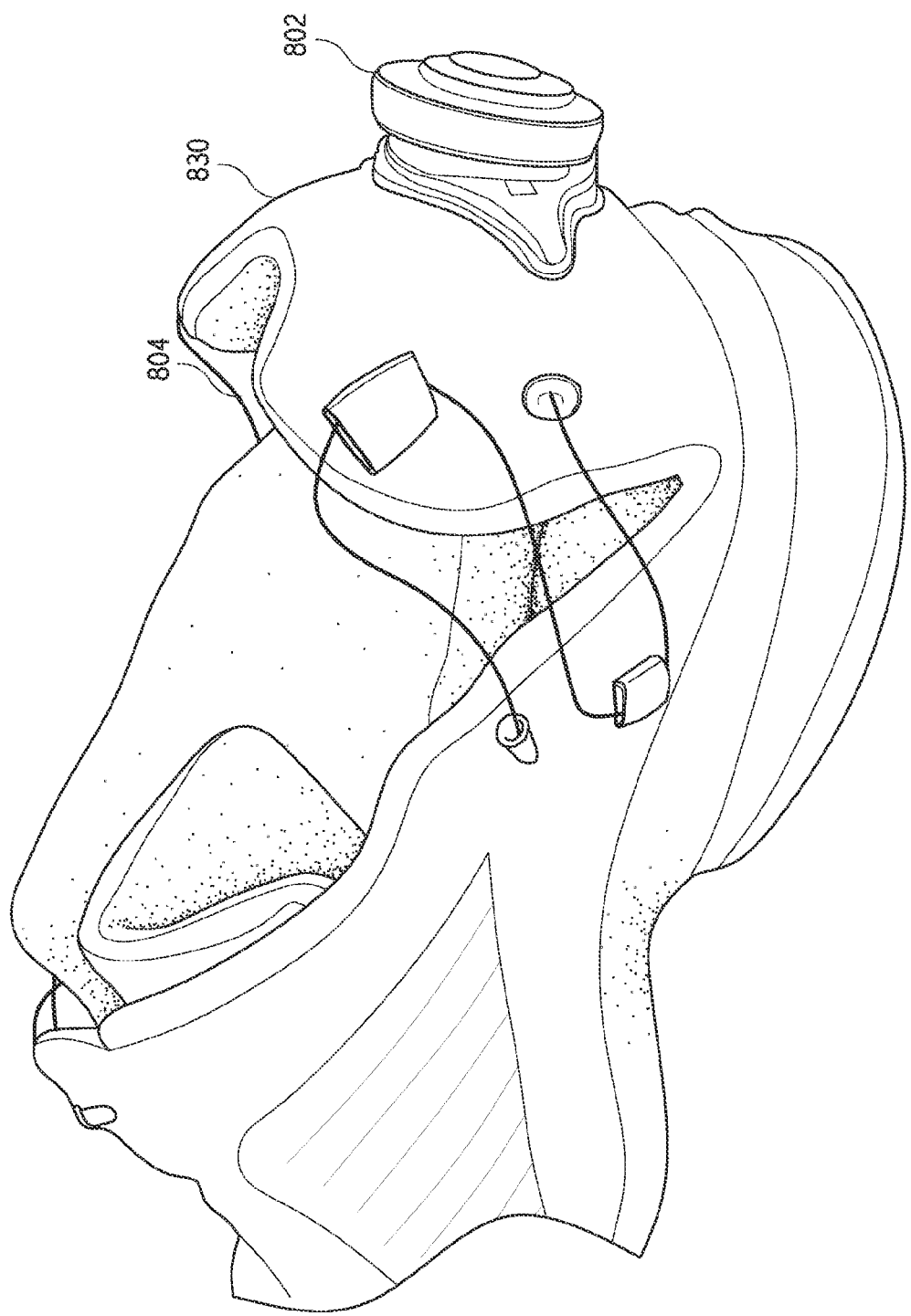
Figure 9A:
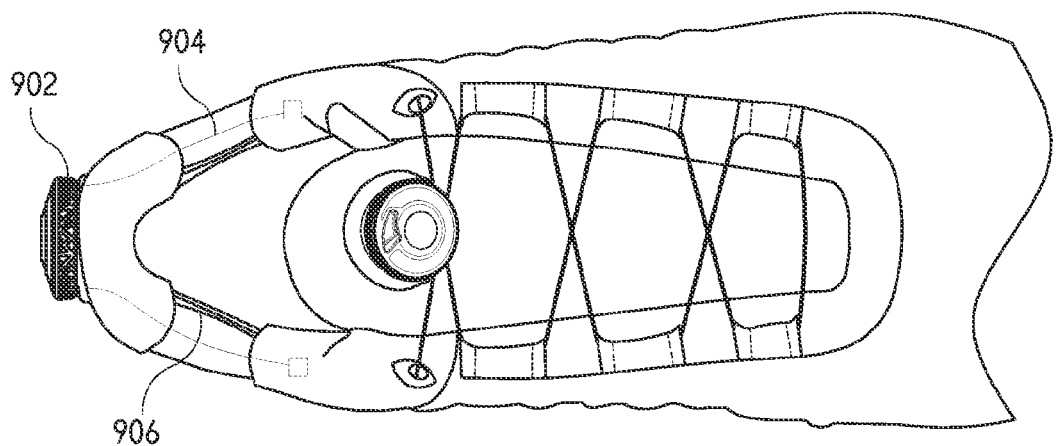
FIGS. 9A-9E illustrate various embodiments of a closure device that may be used to provide collar compression to an individual's heel.
Figure 9B:
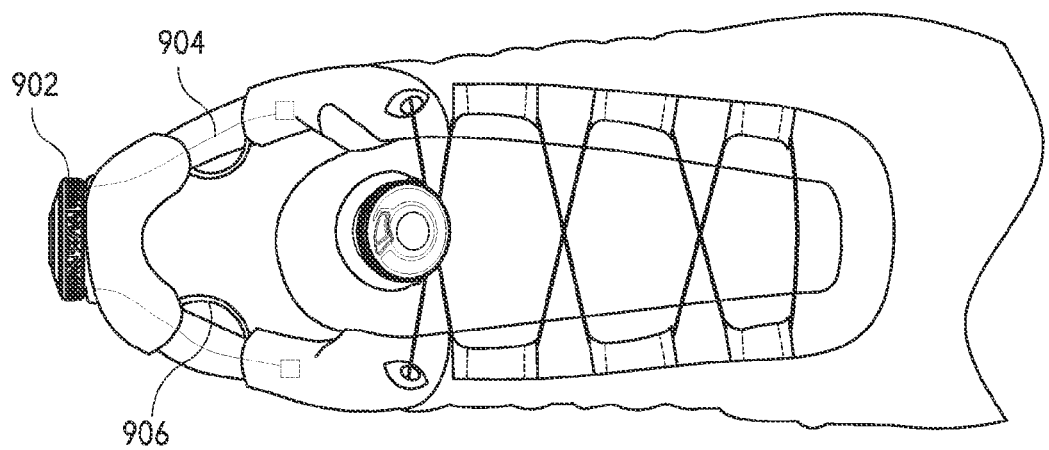
Figure 9C:
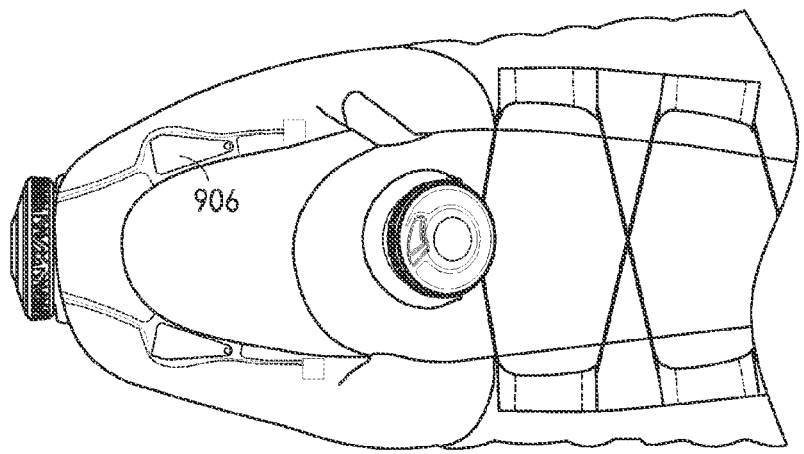
Figure 9D:
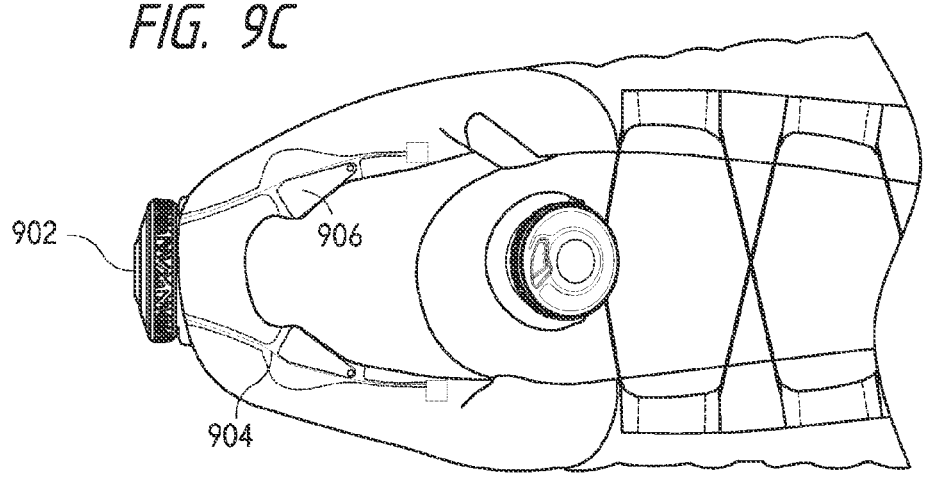
Figure 9E:
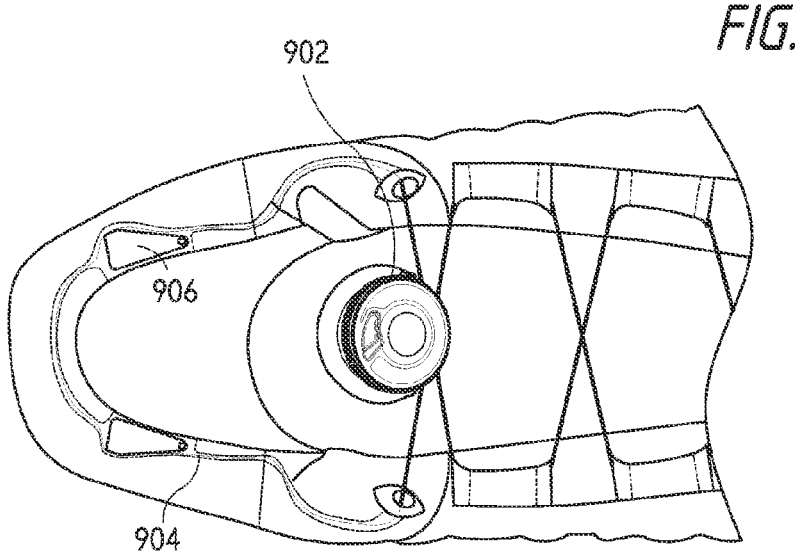

In one embodiment, the shoe's heel counter may be flexible or adjustable by tensioning the lace. As shown in FIGS. 8A and 8B, the heel counter 830 may be hinged to the shoe's sole to allow the heel counter 830 to pivot and press against the back of the user's foot. The lace 804 may be coupled with the heel counter 830 so that tensioning the lace 804 via reel assembly 802 pulls the heel counter 830 forward and into contact with the user's heel. In some embodiments, the attachment point of the lace and heel counter 830 may be adjusted (e.g., vertically) to allow the user to adjust the pull of the lace on the heel counter 830 and/or the pressure of the heel counter 830 on the back of the user's foot. Areas of portions of the collar may also be stiffened as the heel counter is adjusted, to tighten the shoe around the user's heel as desired. In one embodiment, the material of the medial and/or lateral sides of the shoe positioned just forward of the heel counter may be removed so that the shoe comprises an "open" configuration between the heel counter and the front of the heel as shown in FIGS. 8A and 8B. In such embodiments, the lace (or multiple laces) may traverse the open area and couple with the heel counter 830. In other embodiments, webbing may traverse the open portion between the heel counter 830 and forward portion of the shoe.

Although not shown, in another embodiment, a split plate or member may be integrated with the heel counter. The split plate or member may have a separated center portion that may be pulled together with the lace 804 and reel assembly 802 to apply compression to the heel of the foot. In yet another embodiment, external straps may be pulled via the reel assembly 802 and/or lace 804 to apply a force or compression to the foot. As illustrated in FIGS. 8A and 8B, the lace 804 may cross the "open" portion of the shoe multiple times to increase the closure force of the heel counter 830 about the user's heel. The lace 804 may be inserted through tubing that directs the lace 804 to the front of the shoe and/or along the shoe's tongue portion. As such, a single reel assembly 802 may be used to close the heel counter 830 about the user's heel and to close the shoe about the forefront of the foot. The multiple lace crossings about the "open" portion of the shoe may aid in closing the heel counter 830 about the heel in comparison to closing the forefront of the shoe.

Creating Curvature with the Lace

In some embodiments, the curvature or shape of the shoe may be changed as the lace is tensioned. For example, as shown in FIGS. 9A-E, the lace 904 may initially be straight and a portion or area of the shoe flat. The lace 904 or portion of the shoe may curve as the lace 904 is tightened via reel assembly 902. In some embodiments, a member or compression panel 906 may be configured to bow inward as the lace 904 is tensioned to force the portion of the shoe inward against the user's foot. The curved portion of the shoe, or compression member 906, may "pinch" or press against a desired portion of the foot, such as the calcaneus, to apply pressure to that area. In some embodiments, the compression member 906 may be controlled with an independent reel (not shown) or share a reel with other portions of the shoe that are tensioned. In one embodiment, the shoe may include one or more members (e.g., plastic pieces) with a hinge built therein and a lace track in the back so that when the lace is tensioned, the one or more members provide the desired curvature. It should be realized that the curved portion of the shoe can include various deflectable or elastic members and may be positioned at various areas where a "pinch" or similar compression is desired.

Zonal Tensioning

As described briefly above, in some embodiments the lacing system and/or reel assembly may be used to provide "zonal" tensioning. As used herein, zonal tensioning means that separate or individual portions or regions of the shoe or article are differentially tightened. Zonal tensioning may improve the fit of the shoe about the foot, or the fit of an article about the body, by allowing the individual or separate portions/regions to be tightened about the foot in a customized and/or desired manner. For example, the upper region of the shoe may be tightened at a differential rate from the forefront of the shoe, which may increase the fit or hold of the shoe about the foot. Similarly, the heel or collar of the shoe may be differentially tightened from the forefront to increase the hold of the shoe about the heel. The differential tightness may be adjusted or configured based on an activity of the user, or based on a desired fit or wear of the shoe. Differential tightening also allows the shoe to be tailored or customized to unique and individual foot shapes and sizes, which increases the comfort and/or fit of the shoe about the unique foot.

Many of the zonal tensioning embodiments include a first guide member that is coupled with the article (hereinafter shoe) and positioned within a first zone of the shoe. The embodiments also include a second guide member that is coupled with the shoe and positioned within a second zone of the shoe. At least a portion of the second zone may be different than the first zone. The embodiments may also include other guide members that are positioned within the first zone, the second zone, and/or other zones of the shoe. A first tension member (hereinafter first lace) is guided by the first guide member within the first zone of the shoe. Tensioning of the first lace causes tightening of the first zone of the shoe. A second tension member (hereinafter second lace) is guided by the second guide member within the second zone of the shoe. Tensioning of the second lace causes tightening of the second zone of the shoe. The embodiments may also include other laces that are guided by guide members within the first zone, second zone, and/or additional zones.

A tensioning mechanism or reel assembly (hereinafter reel assembly) is also coupled with the shoe and with the first lace and second lace. The reel assembly is configured to tension the first lace and second lace to tighten the first and second zones. In some embodiments, the reel assembly may be operated to differentially tension the first lace and the second lace, and thereby differentially tighten the first and second zones of the shoe.

Figure 10A:
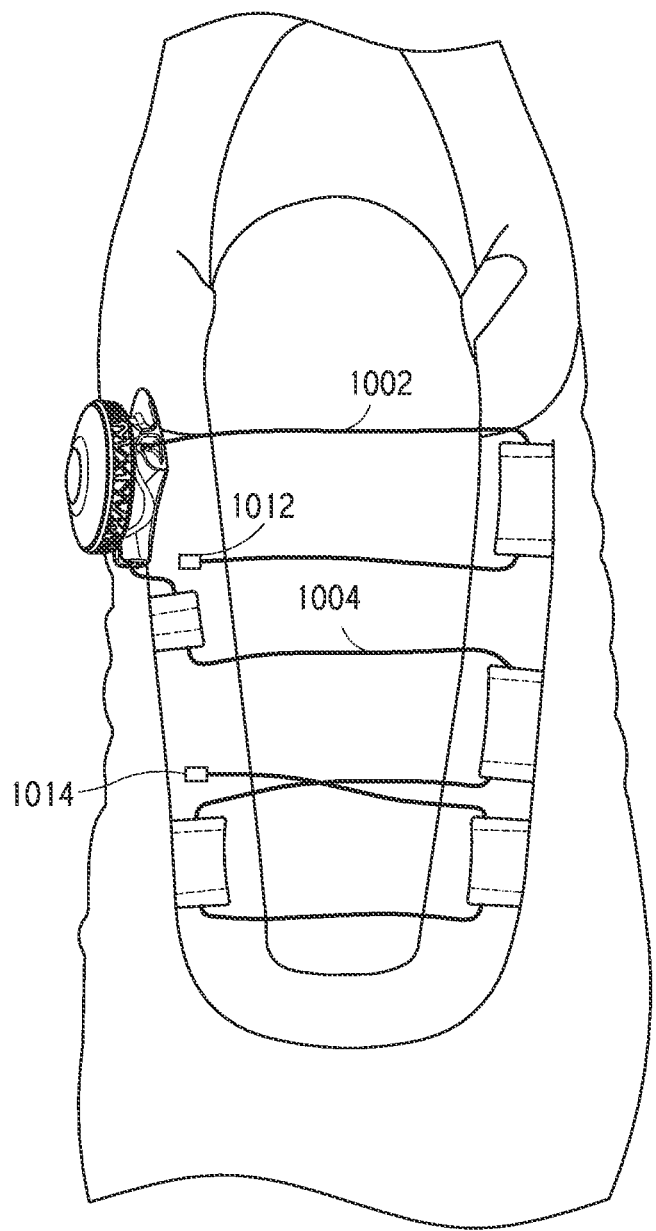
FIGS. 10A-G illustrate various embodiments of closure devices and lacing systems that may be used to zonally tension a shoe.

In some embodiments, the shoes may be custom fit by using multiple laces that attach to a spool and/or by using lace ends that may be adjustable or fit into an adjustable lace end as describe in FIGS. 7A-C. FIGS. 10A-12N illustrate various embodiments of zonal tensioning systems and components. For illustrative purposes, FIG. 10E shows an embodiment that utilizes a single tension zone. In FIG. 10E, when the lace is tensioned, via a reel assembly, the lace throughout the single zone is approximately equally tensioned, accounting for any frictional losses. In contrast, the other embodiments illustrated in FIGS. 10A-12Q may be used to differentially tension individual tension zones of the shoe.

In one embodiment, the closure system may include multiple laces that are configured to tighten separate zones of the shoe and that have lace ends that terminate in or adjacent the separate zones. In some embodiments, the lace ends may be adjustable relative to the shoe and/or separate zones to vary the length of the lace available for tightening the respective zone. For example, as shown in FIG. 10A, the lacing system may include a first lace 1002 that crosses the shoe's tongue and terminates in a first lace end 1012. The lace path of the first lace 1002 may represent a first zone of the shoe. The lacing system also includes a second lace 1004 that crosses the shoe's tongue and terminates in a second lace end 1014. The lace path of the second lace 1004 may represent a second zone of the shoe. The first and second laces, 1002 and 1004, may be differentially tensioned to differentially tightened the first and second zones of the shoe, and thereby vary the force applied by the shoe on the user's foot.

In one embodiment, the length of the first and/or second lace, 1002 and 1004, may be adjusted or varied within the respective zones to allow the zones to be differentially tightened. For example, the first lace 1002 may include an adjustment component or system, such as those described in FIG. 7A or described elsewhere herein, that allows the first lace end 1012 to be varied relative to the shoe. The second lace 1004 length may likewise include an adjustment component that allows the second lace end 1014 to be adjusted relative to the shoe. Subsequent operation of the reel assembly may differentially tension the first and second laces, 1002 and 1004. Additional methods of varying the lace ends are described hereinbelow.

Figure 10B:
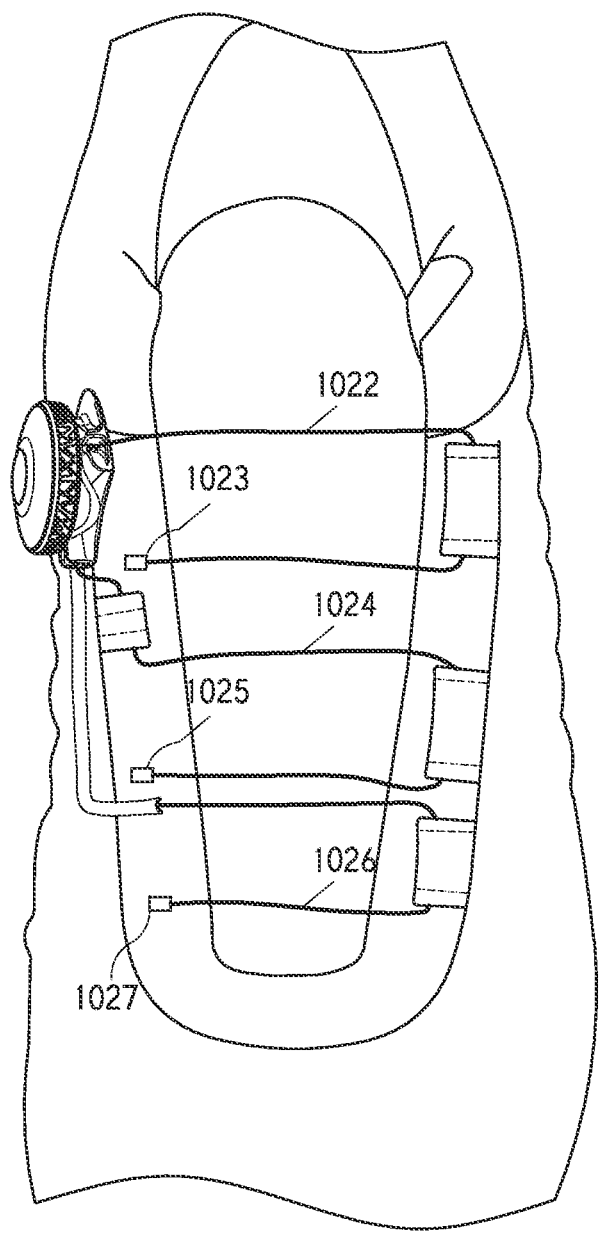

FIG. 10B illustrates another embodiment of zonal tensioning. Specifically, the lacing system includes three zones having a first lace 1022 that terminates at a first lace end 1023, a second lace 1024 that terminates at a second lace end 1025, and a third lace 1026 that terminates at a third lace end 1027. A single reel assembly tensions all three laces, 1022, 1024, and 1026. The lace lengths of one or more of the laces, 1022, 1024, and 1026, may be adjusted to provide a desired and/or differential tension and pressure in each zone. For example, the lace ends of one or more of the respective laces may include adjustment members that allow the ends to be adjusted relative to the shoe as described herein. In some embodiments, one or more of the laces may be routed to the various zones via tubing that is coupled with the shoe.

Figure 10C:
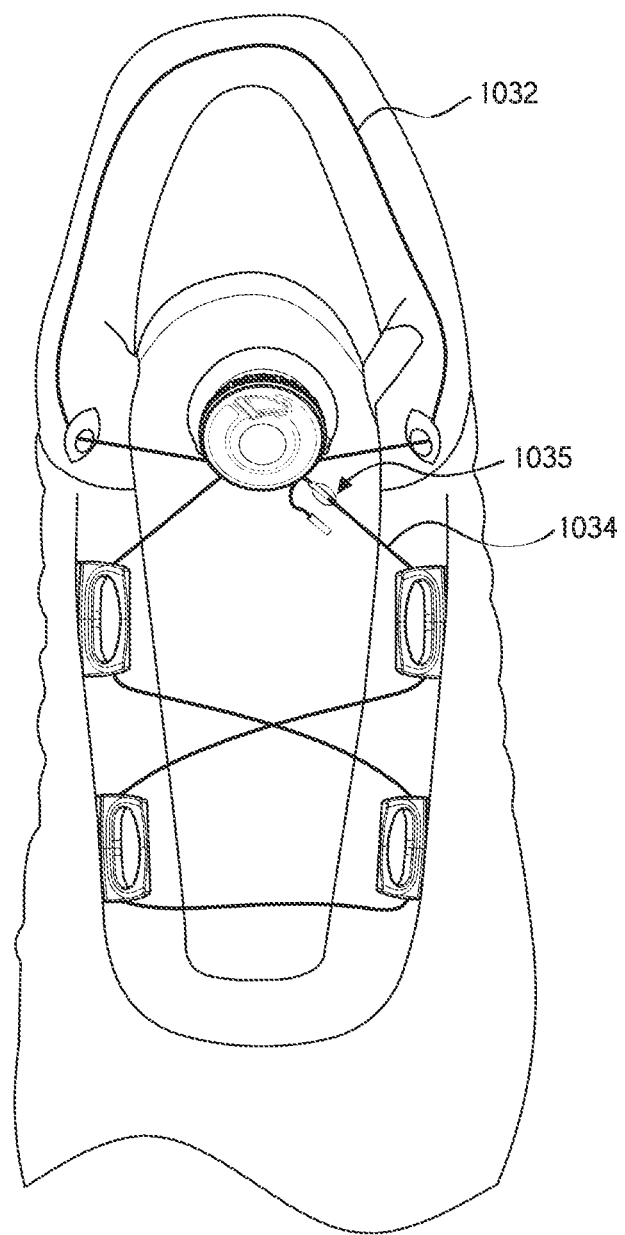
Figure 10D:
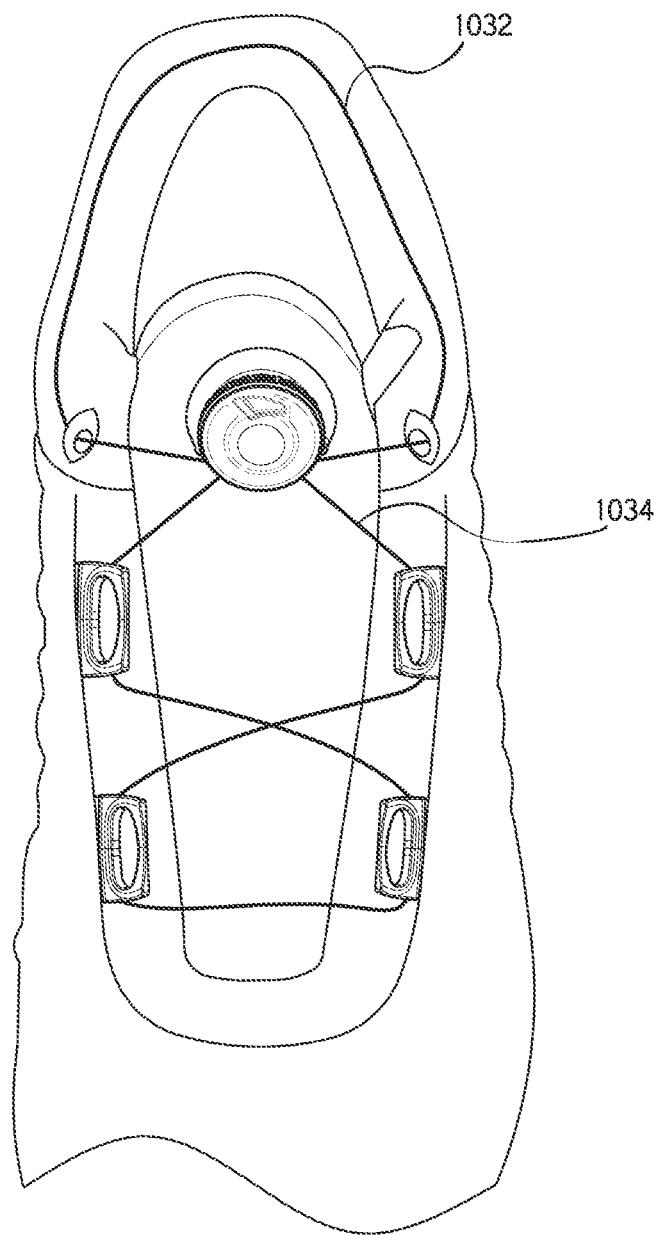
Figure 10E:
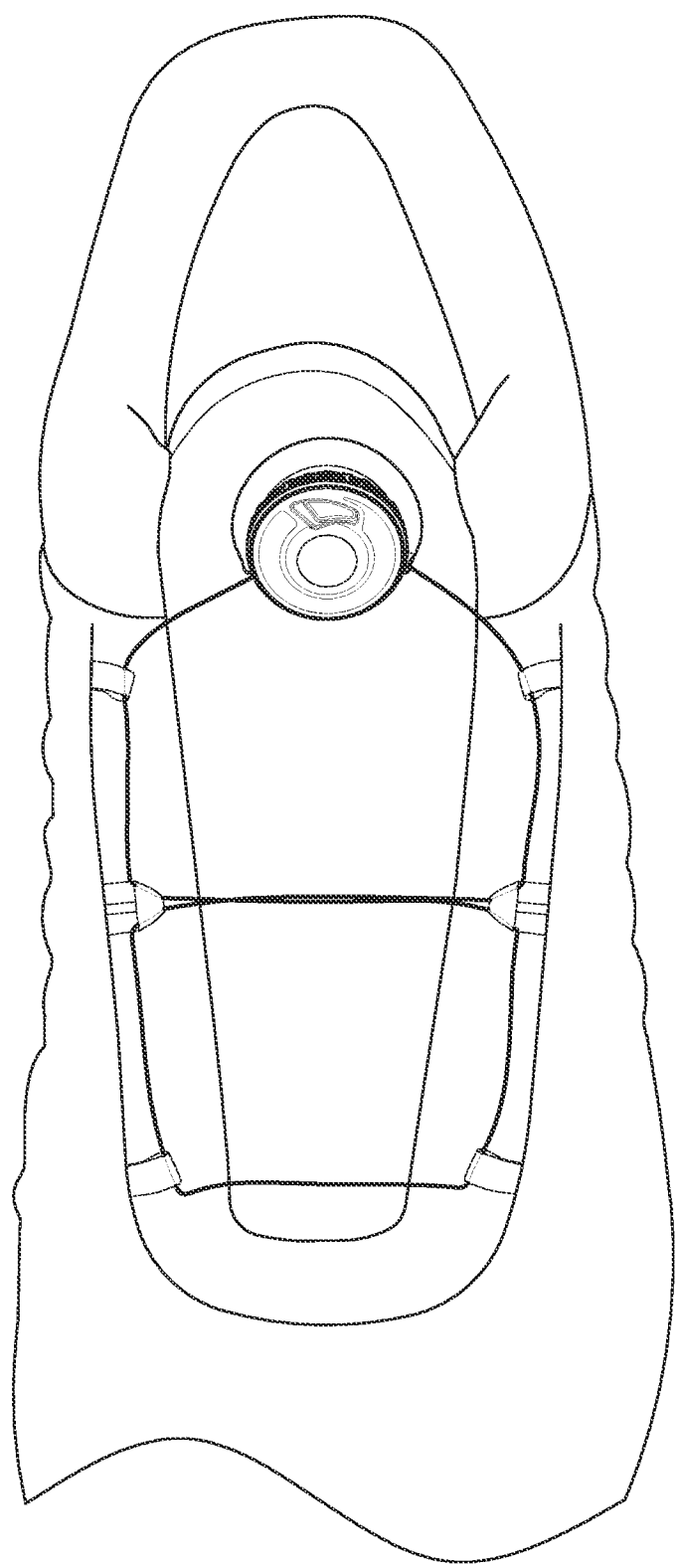

FIGS. 10C and 10D illustrate another embodiment of zonal tensioning. Specifically, a first lace 1032 may wrap around the collar of the shoe and define a first tension zone while a second lace 1034 crisscrosses the shoe's tongue and defines a second tension zone. The first lace 1032 may traverse through a fabric sleeve and/or tubing (e.g., via tube-in-tube configuration of FIGS. 6C and 6D) and may compress the collar around the user's ankle while the second lace 1034 applies pressure to the forefront of the user's foot. In some embodiments, both ends of the first lace 1032 may be coupled with the reel so that operation of the reel pulls on both ends of the lace. In another embodiment, one end of the first lace 1032 may be terminated and/or adjustable (not shown). As shown in FIG. 10C, in some embodiments the second lace 1034 may terminate in a lace end 1035, which may allow for adjustment of the lace length. In other embodiments, both ends of the second lace 1034 may couple with the reel assembly as shown in FIG. 10D.

Figure 10F:
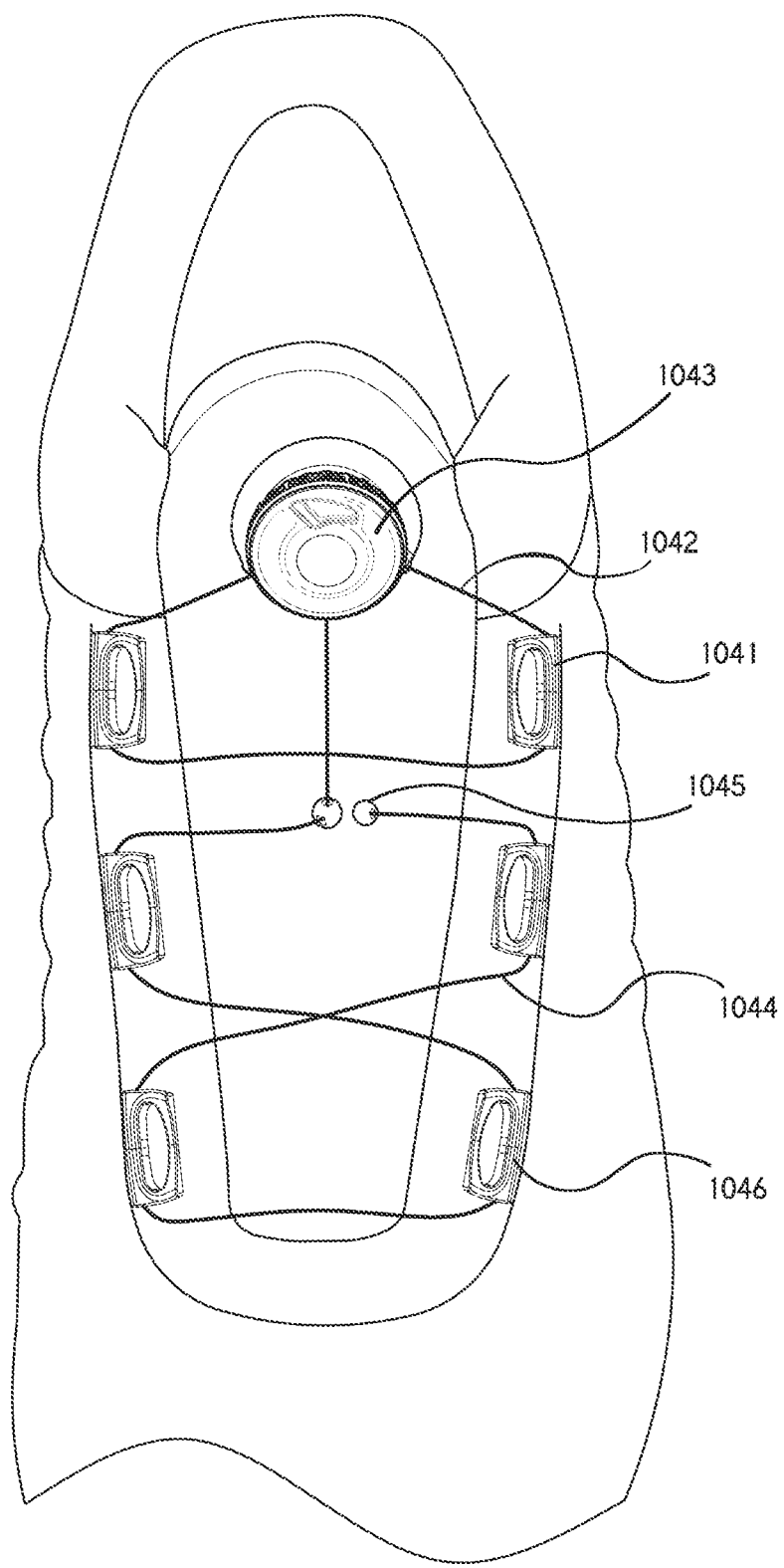

FIG. 10F illustrates another embodiment of providing zonal tensioning. Specifically, a first lace 1042 may traverse an upper region of the shoe's tongue and terminate at a first lace end, or couple with the reel assembly 1043, to define a first tension zone adjacent the upper region of the shoe's tongue. An end of the first lace 1042 may be adjustable as described herein. The first lace 1042 may be guided by first guides 1041 that are positioned within the first tension zone. A second lace 1044 may traverse a lower portion of the shoe's tongue and terminate at a second lace end 1045 to define a second tension zone adjacent the lower region of the shoe's tongue. The second lace end 1045 may be adjustable as described herein. The second lace 1044 may be guided by second guides 1046 that are positioned within the second tension zone. In some embodiments, the first and/or second lace, 1042 and 1044, may traverse the respective zones of the shoe in a square or crisscrossing manner as shown in FIG. 10F. Reel assembly 1043 may be operated to differentially tension the first and/or second lace, 1042 and 1044, and thereby differentially tighten, or apply zonal pressure, to the first and second tension zones as described herein, which may custom fit the shoe about the user's foot.

Although the reel assembly in FIGS. 10A-F is generally described as differentially tensioning the lace and differentially tightening the shoe, it should be realized that in some embodiment, the tension in the individual laces and/or separate zones of the shoe may be roughly the same. In such embodiments, operation of the reel assembly may roughly equally tension the lace and/or equally tighten the separate zones.

Figure 10G:
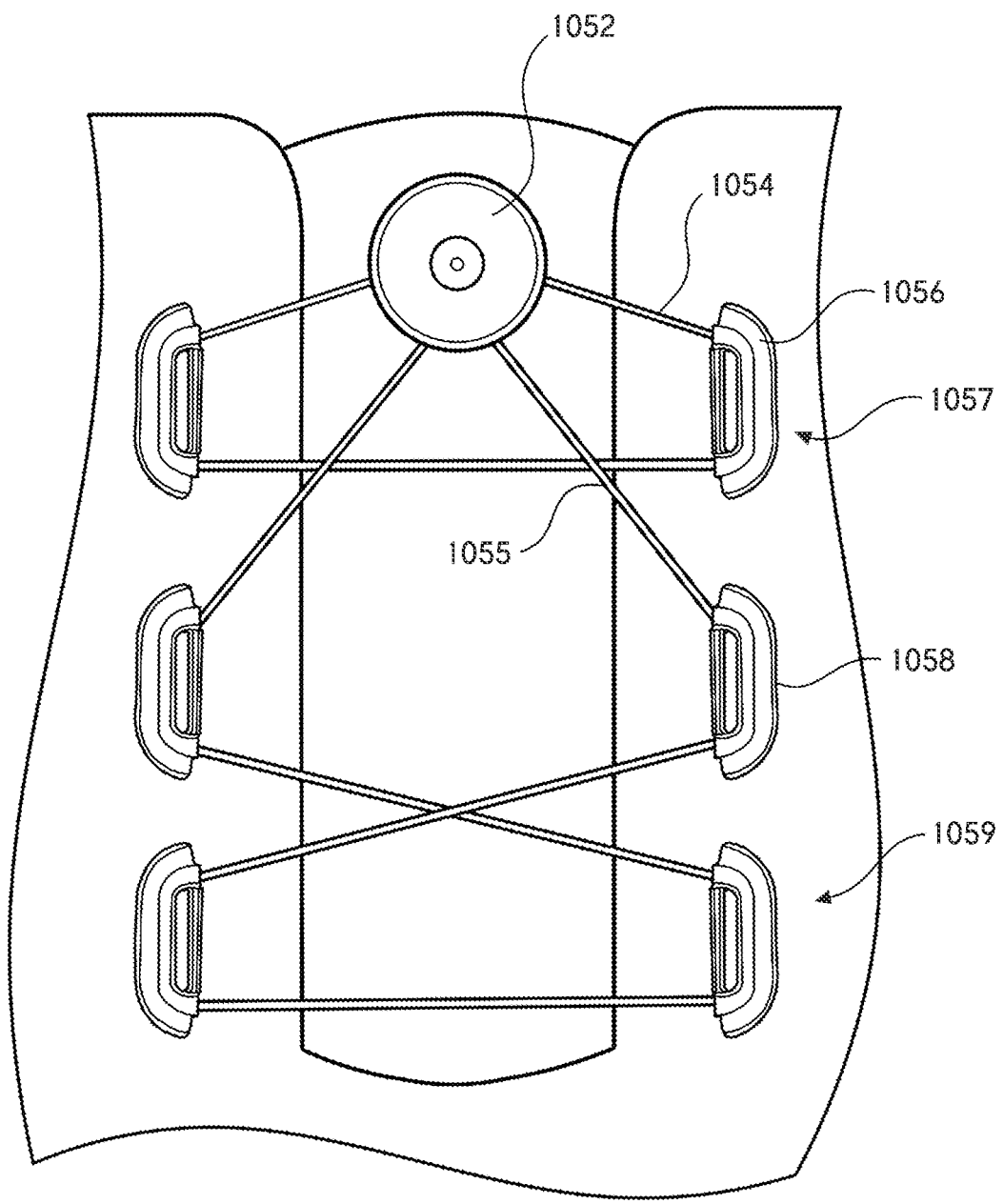

FIG. 10G illustrates another embodiment of zonal tensioning. Specifically, a first lace 1054 is guided by first guide members 1056 that are positioned within and define a first zone 1057 about the tongue of the shoe. Both ends of the first lace 1054 are coupled with a reel assembly 1052 and are tensionable thereby to tighten the first zone 1057 about an upper portion of the user's foot. A second lace 1055 is guided by second guide members 1058 that are positioned within and define a second zone 1059 about the tongue of the shoe. At least a portion of the second zone 1059 is different than the first zone 1057 although the two zones may overlap to some degree so that tensioning of one or both laces tightens both zones to some small degree. Both ends of the second lace 1055 are coupled with the reel assembly 1052 and are tensionable thereby to tighten the second zone 1059 about a lower portion of the user's foot. Coupling both ends of the first and second lace, 1054 and 1055, with the reel assembly 1052 may provide an improved closure and fit of the shoe about the user's foot.

Figure 12A:
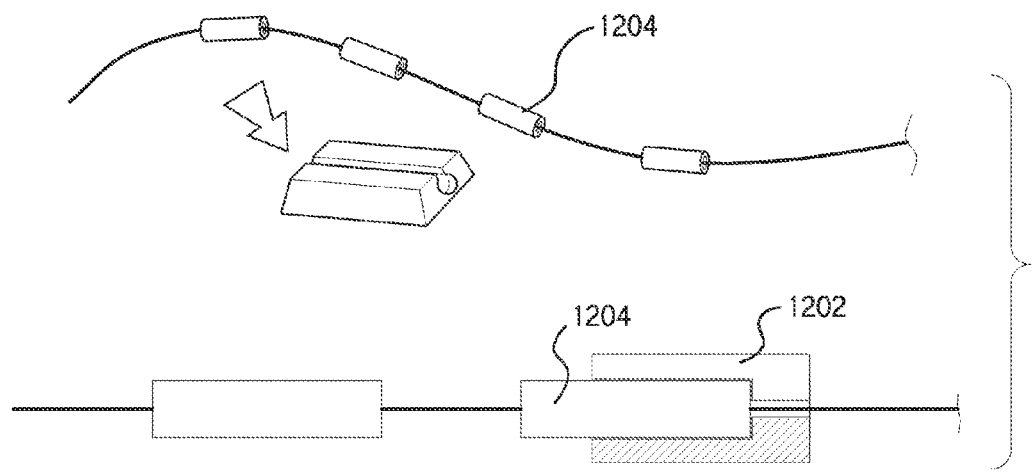
FIGS. 12A-R illustrate various embodiments of components that may be used to adjust an end of a lace of a lacing system and/or adjust the tension in the lace.

As shown in FIG. 10G, in some embodiments, the first zone 1057 may include two guide members 1056 while the second zone 1059 includes four guide members 1058. In other embodiments, the number of guide members used in each zone may be varied and/or the first and second laces, 1054 and 1055, may each be guided by one or more of the same guide members. Although not shown in FIG. 10G, in some embodiments an initial tension of the first and/or second lace, 1054 and 1055, may be varied to affect the differential tightness applied and/or achieved in each zone. For example, the lace adjustment mechanisms described in FIGS. 12A-Q, and particularly 12O-Q, may be used to vary the initial tension in the first and/or second lace, 1054 and 1055, as desired. For example, in some embodiments the first guide members 1056 and/or second guide members 1058 may have an open back or open channel configuration that allows the respective lace to be removed or uncoupled from the guide. The lace may then be coupled with an adjacent guide member as shown in FIG. 12O. In other embodiments, the first guide members 1056 and/or second guide members 1058 may be positioned on a track that allows the guide member to be proximally and distally moved relative to the shoe as shown in FIGS. 12P and 12Q.

Lace Length Adjustment Via Teeter Mechanisms

FIGS. 11A-11D illustrate various embodiments that may be employed to differentially tension lace and/or differentially tighten zones. Differential lace tension/zone tightness is typically achieved by varying the length of the lace within a respective zone. The embodiments of FIGS. 11A-11D illustrate various methods in which lace length within zones of a shoe may be varied.

In some embodiments, zonal pressure or differential tightness may be achieved by employing a "teeter" or adjustment mechanism. The "teeter" or adjustment mechanism is used to adjust a respective amount of lace within a zone that is tensioned via a reel assembly. As used herein, the term "teetering" generally means lengthening a lace within one zone while shortening another lace in a separate zone by a corresponding amount. Such teetering or lace adjustment may be achieved using a special reel mechanism. For example, a first end of a lace may be pulled or moved out of a first port of the reel mechanism while a second and opposite end of the lace is drawn into a second port of the reel mechanism. In some embodiments, the reel assembly may also function as the teeter or adjustment mechanism.

Figure 11A:
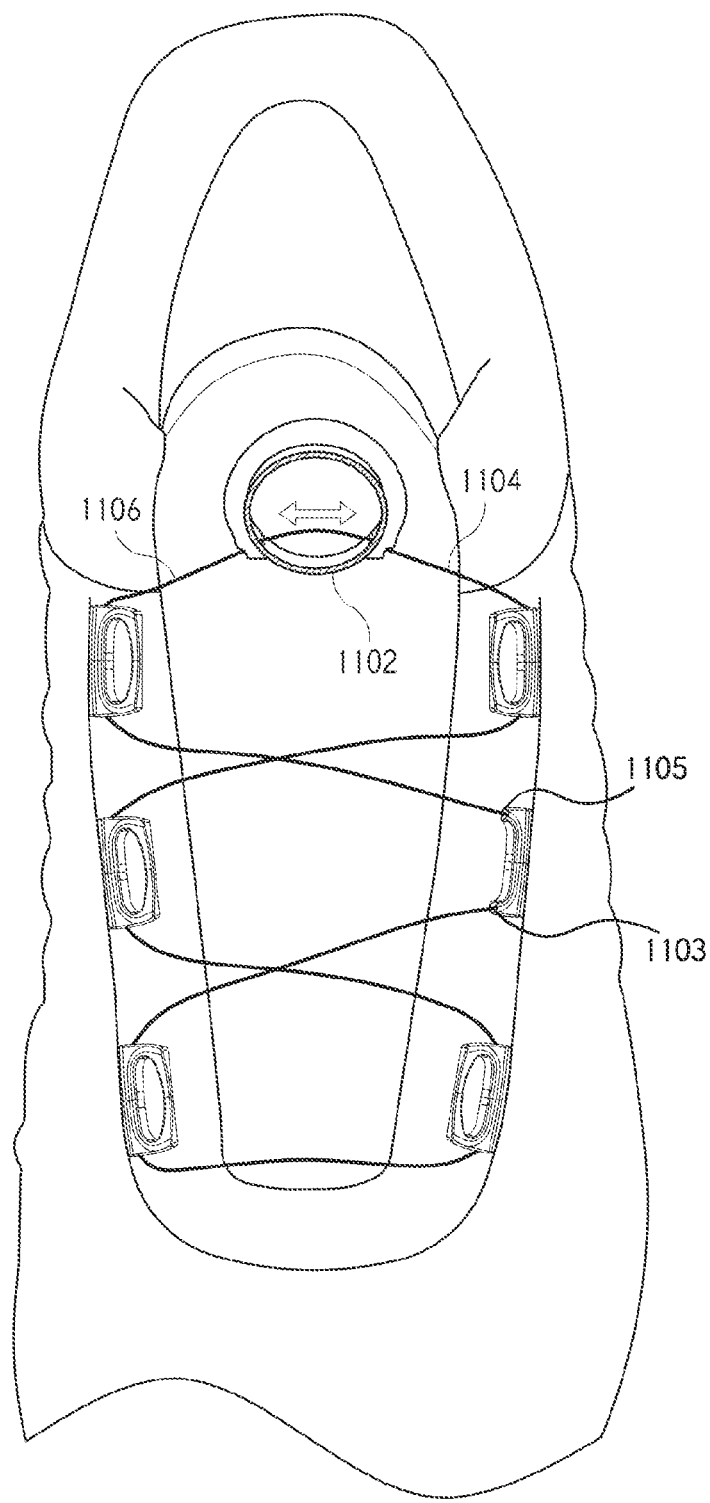
FIGS. 11A-D illustrate various embodiments of teeter mechanisms that may be used to vary a length of lace within zones of a shoe.

FIG. 11A illustrates one embodiment of a teeter or adjustment mechanism 1102 (hereinafter teeter mechanism). A single lace is positioned through the teeter mechanism 1102 with a first portion 1104 exiting and positioned on a first side of the teeter mechanism 1102 and a second portion 1106 exiting and positioned on a second side of the teeter mechanism 1102 opposite the first side. The first portion 1104 terminates at a first end 1102 while the second portion terminates at a second end 1105, which may be adjacent a forefront of the shoe. The relative lengths of the first portion 1104 and the second portion 1106 may be adjusted by pulling the lace through the teeter mechanism 1102, which increases the tension in either the first portion 1104 or second portion 1106 while decreasing the tension in the other portion. Subsequent operation of the reel assembly, which may be the same mechanism as teeter mechanism 1102, differentially tensions each lace portion, 1104 and 1106, thereby applying a differential zonal pressure or tightness.

Figure 11B:
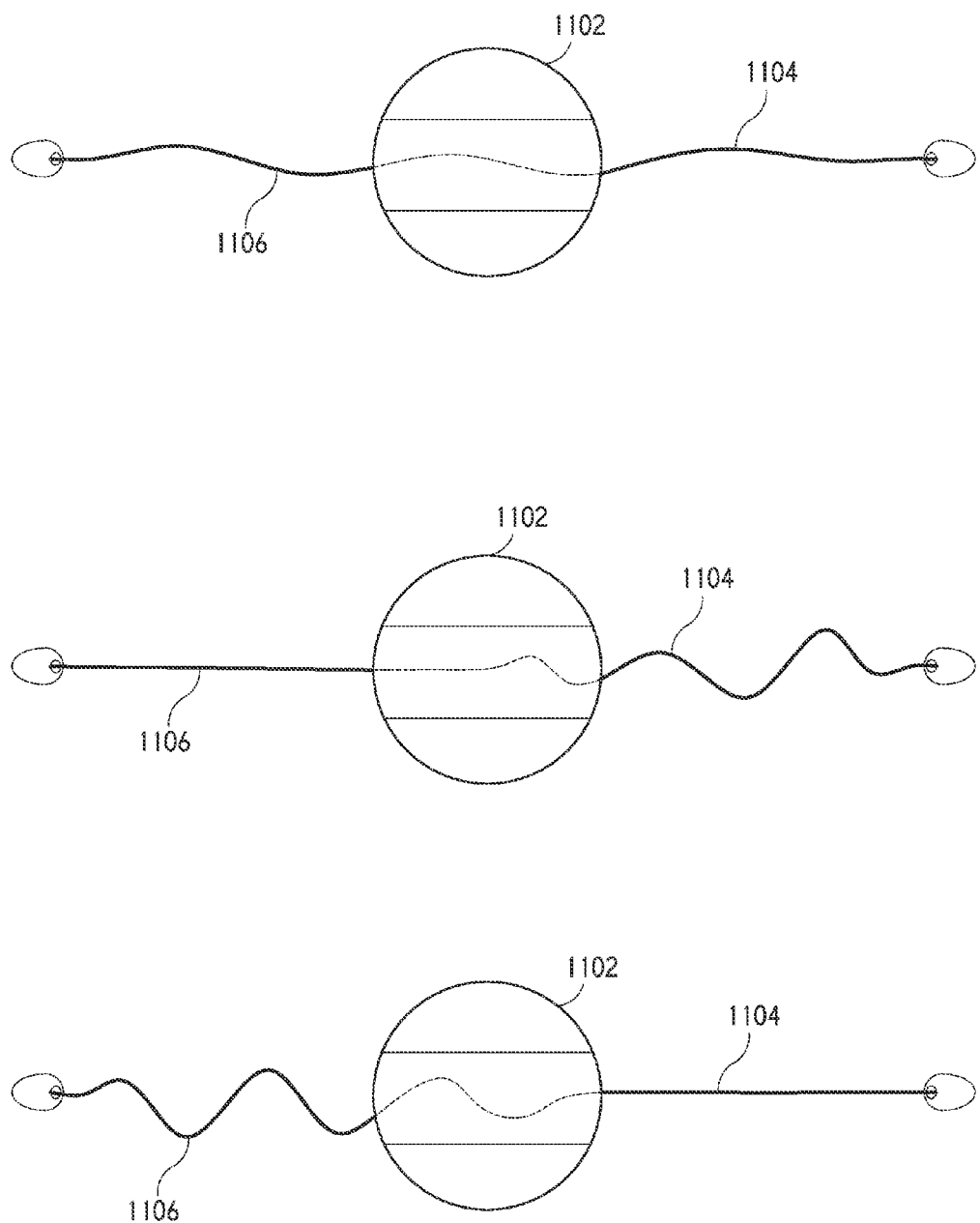

As shown in FIG. 11B, the first portion 1104 and second portion 1106 may have an relatively equal tension (upper image) so that operation of the reel assembly (e.g., teeter mechanism 1102) applies an approximately equal tension in both lace portions. Or, as shown in middle image, the first portion 1104 may be pulled through the teeter mechanism 1102 (e.g., through a channel) so that the lace is unbalanced on opposing sides with the first portion 1104 having a relatively greater lace length and less lace tension. Similarly, as shown in bottom image, the second portion 1106 may be pulled through the teeter mechanism 1102 so that the lace is unbalanced on opposing sides with the second portion 1106 having a relatively greater lace length and less lace tension. Subsequent operation of the reel assembly (e.g., teeter mechanism 1102) in the unbalanced state creates differential tension in the first and second lace portions, 1104 and 1106, and differential zonal pressure or tightness within the shoe. The first and second portions, 1104 and 1106, may be traversed across the shoe in any desired manner to provide a desired zonal pressure configuration and/or effect. In some embodiments, the lace may be pulled through the teeter mechanism 1102 by hand when the reel assembly is in an lace setting state, or other components (not shown) may be used to pull the lace through the teeter mechanism 1102.

Figure 11C:
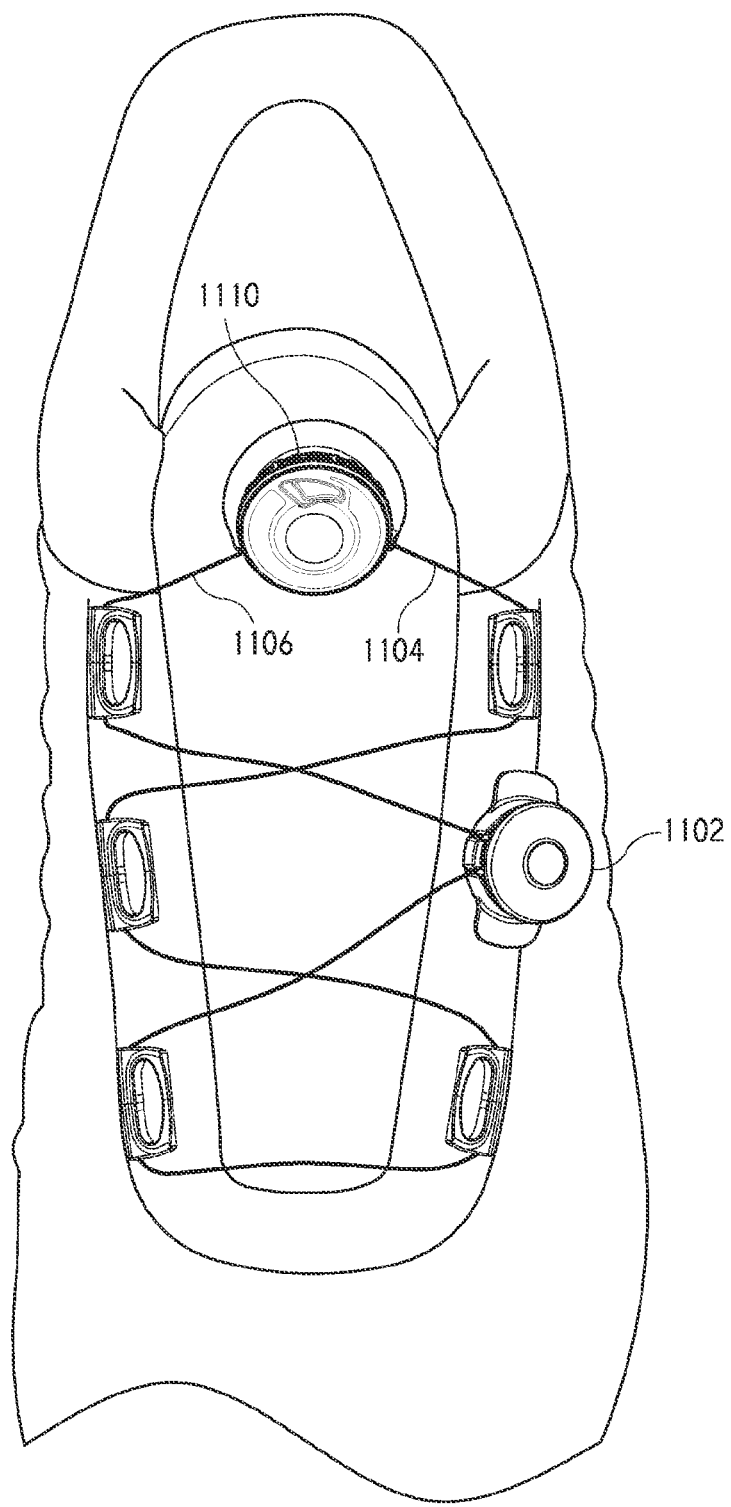

FIG. 11C illustrates a teeter system that uses a teeter mechanism or device 1102 that is separate from the reel assembly 1110. The lacing system may include a first lace or lace portion 1104 that is coupled with the reel assembly 1110 and that traverses along or about a first zone of the shoe. The first lace 1104 terminates at the teeter mechanism 1102. The lacing system also includes a second lace or lace portion 1106 that likewise is coupled with the reel assembly 1110 and that traverse along or about a second zone of the shoe. The second lace 1106 likewise terminates at the teeter mechanism 1102. Operation of the teeter mechanism 1102 lengthens either the first lace 1104 or second lace 1106 and shortens the other lace. In some embodiments, each end of the lace, 1104 and 1106, may be pre-wound onto or about teeter mechanism 1102 by at least one revolution.

Figure 11D:
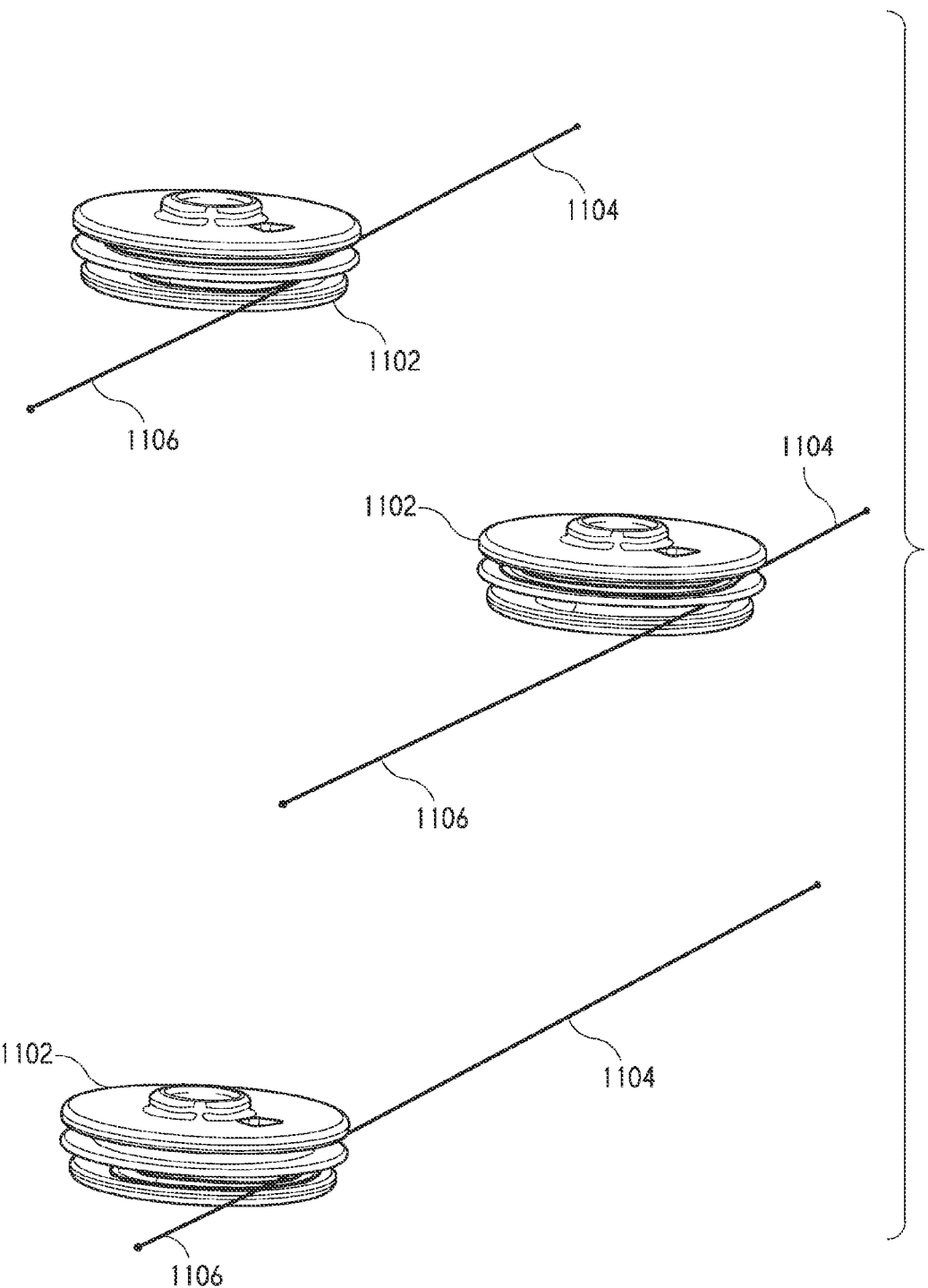

The laces, 1104 and 1106, may be would in opposite directions so that turning the knob of teeter mechanism 1102 winds one of the laces, 1104 and 1106, out of a first port while winding the opposite lace into a second port. Increased pre-winding of the lace, 1104 and 1106, about teeter mechanism 1102 may increase, or provide additional, stroke as desired. In this manner, the tension in each lace may be adjusted so that operation of the reel assembly 1110 differentially tensions the respective laces, 1104 and 1106, by a desired amount to apply a desired differential zonal pressure or tightness. Embodiments of winding the lace, 1104 and 1106, about the teeter mechanism 1102 are illustrated in FIG. 11D. In one embodiment, the teeter mechanism 1102 may include a two-tiered spool arrangement that is positioned within a housing. The two-tiered spool may or may not include different diameter spools as described previously. Rotation of the spool via teeter mechanism 1102 may vary the lengths of the first and second laces, 1104 and 1106. In other embodiments, the teeter mechanism 1102 may be a lever, a cam, a pull through spool device, and the like.

In some embodiments, teeter mechanism 1102 may be a second reel assembly that may have a configuration and/or function similar to reel assembly 1110. In such embodiments, a knob of the second reel assembly (i.e., teeter mechanism 1102) may be rotated to wind first lace portion 1104 or second lace portion 1106 about a spool of the reel assembly while unwinding the other lace portion from the spool. In this manner, the lace tension in one of the lace portions may be increased while the lace tension in the other lace portion is simultaneously decreased. As such, the second reel assembly may be used to influence the lace length and/or initial lace tension in the first and second zones and thereby zonally or differentially tension the lace.

In other embodiments, multiple tracks or panels, multiple guides, and/or one or more crossover points may be used to create differential tension with a single reel. Further, the shoe may be fitted with multiple areas where releasing guides may be attached so that the tension applied in one or more zones may be adjusted based on the specific user.

Lace Termination Adjustment

In some embodiments, the lace length may be adjusted at the lace ends or termination points to vary an initial tension in respective laces (i.e., prior to operation of a reel assembly). FIGS. 12A-12Q illustrate various embodiments in which the ends of a lace may be adjusted. These embodiments may be employed in the device illustrated in FIG. 7A wherein the lace ends are each adjustable to differentially tension the lace and/or differentially tighten various zones of a shoe or article.

Figure 12B:
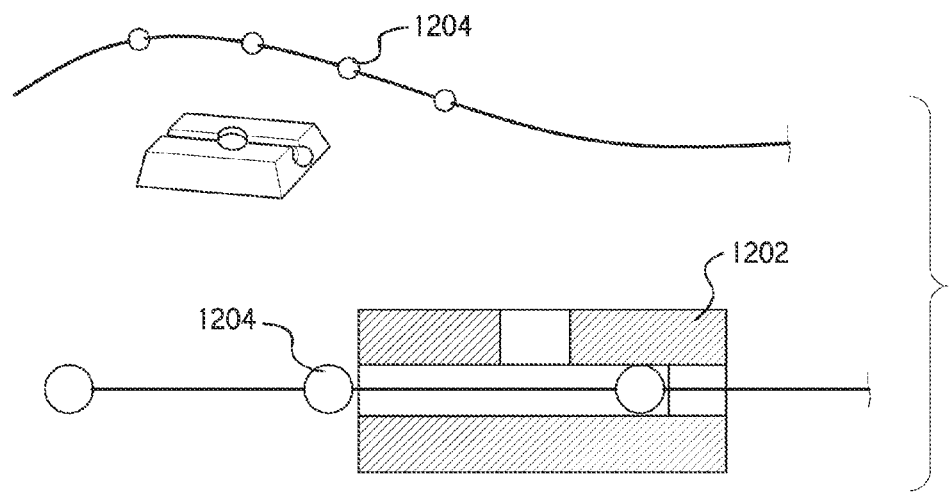

FIGS. 12A and 12B illustrate a ball and string, or cylinder and string, concept for adjusting lace length. Specifically, a distal portion of the lace may include "balls/cylinders" 1204 or enlarged portions, which fit and lock within grooves or recessed lace ends 1202. The lace may be pulled until a desired tension or lace length is achieved and a ball/cylinder or enlarged portion 1204 adjacent the recessed end 1202 may be inserted within the recessed end 1202 to lock the lace in place.

Figure 12C:
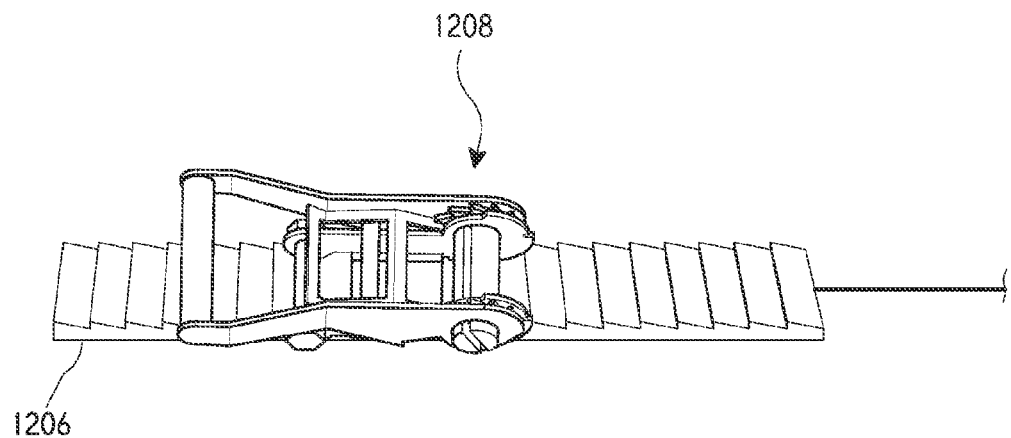
Figure 12D:
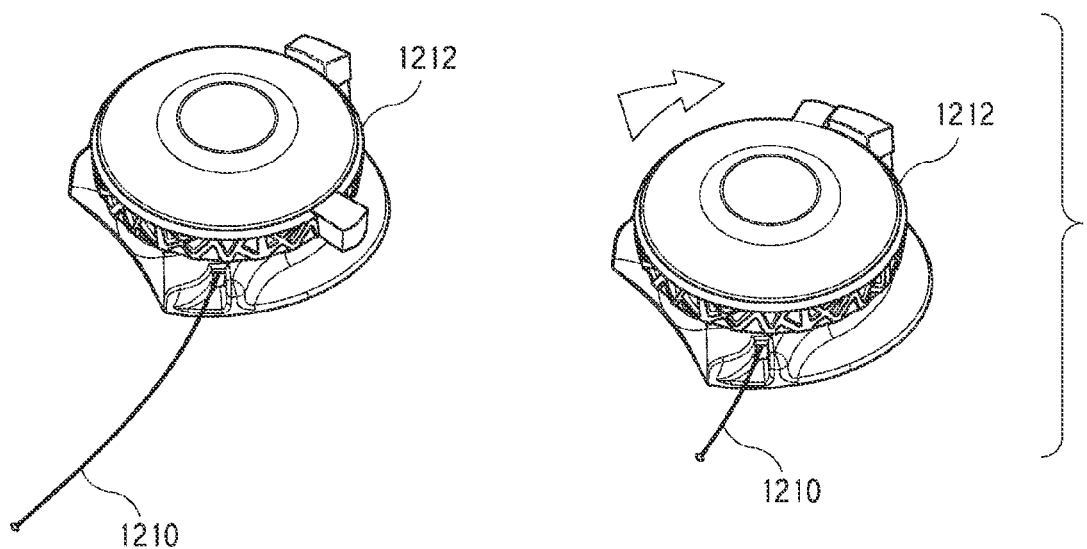
Figure 12E:
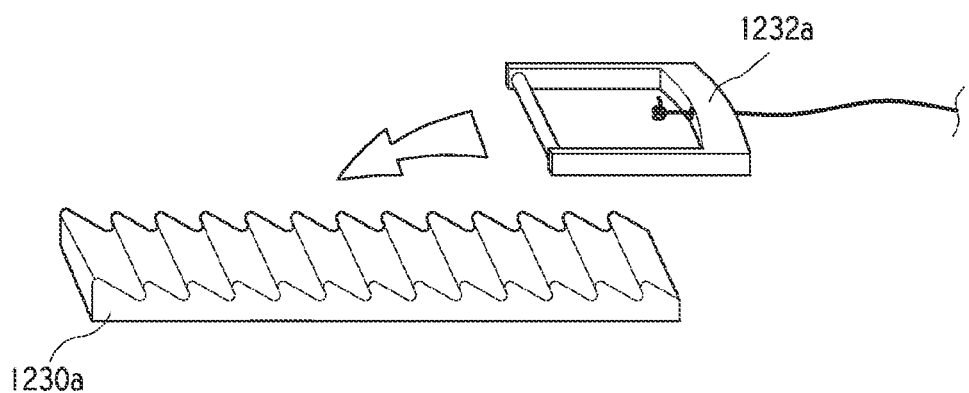

As shown in FIG. 12C, in another embodiment the lace may be coupled with a ratchet system, 1206 and 1208, that allows the lace length to be adjusted by operation of the ratchet device 1208. The lace may be coupled with a ratchet track 1206 that is moved proximally and distally via ratchet device 1208. Movement of the ratchet track 1206 cause the lace to length or shorten within a respective zone of the shoe or article. As shown in FIG. 12D, in another embodiment the lace 1210 may be coupled with a rotatable knob 1212 or cam that winds the lace around a spool to adjust the lace length. The knob 1212 or cam may have a limited range of motion, such as by using an internal mechanism/stop or external mechanism/stop, so that the lace length variation is limited to a defined amount. As illustrated in FIG. 12E, in another embodiment the lace 1214 may be coupled with a cable adjustment system, which may include a bolt or screw 1218 that is coupled with the lace 1214 and that is threaded through a nut 1216 that presses against a stop component 1220 that is anchored to the shoe or article. As the bolt 1218 is rotated relative to the nut 1216, the threads of bolt 1218 and nut 1216 cause the bolt 1218 to displace relative to the nut 1216 and thereby move relative to the shoe or article. Displacement of the bolt 1218 in this manner varies the length of the lace 1214 within a zone of the shoe or article and thereby varies the tension in the lace 1214.

Figure 12F:
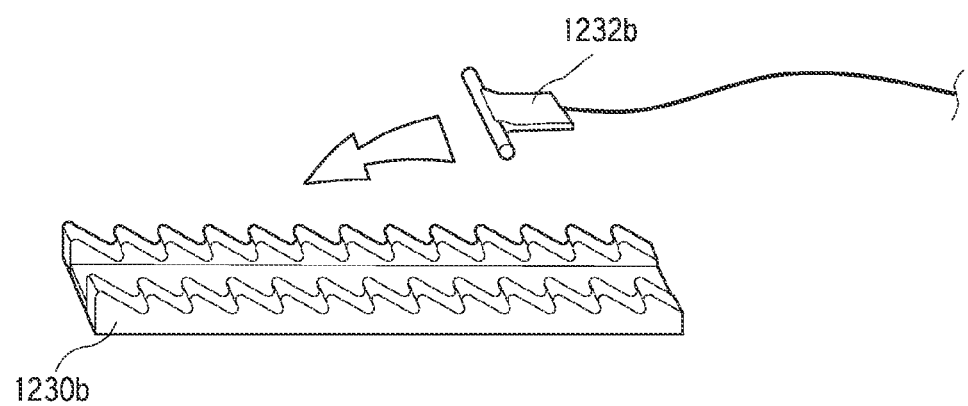
Figure 12G:
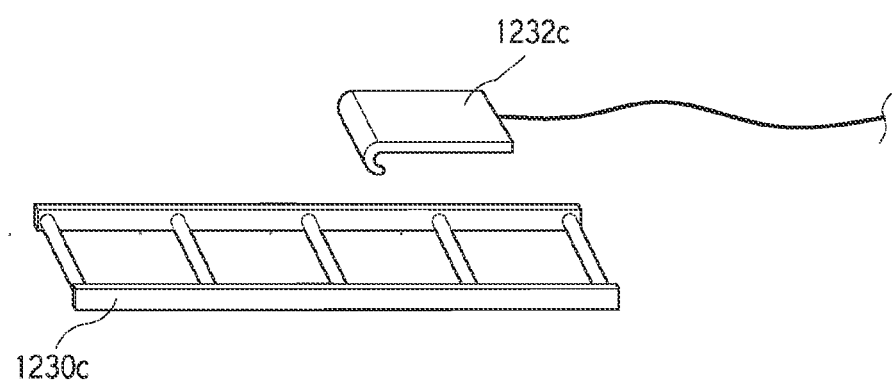
Figure 12H:
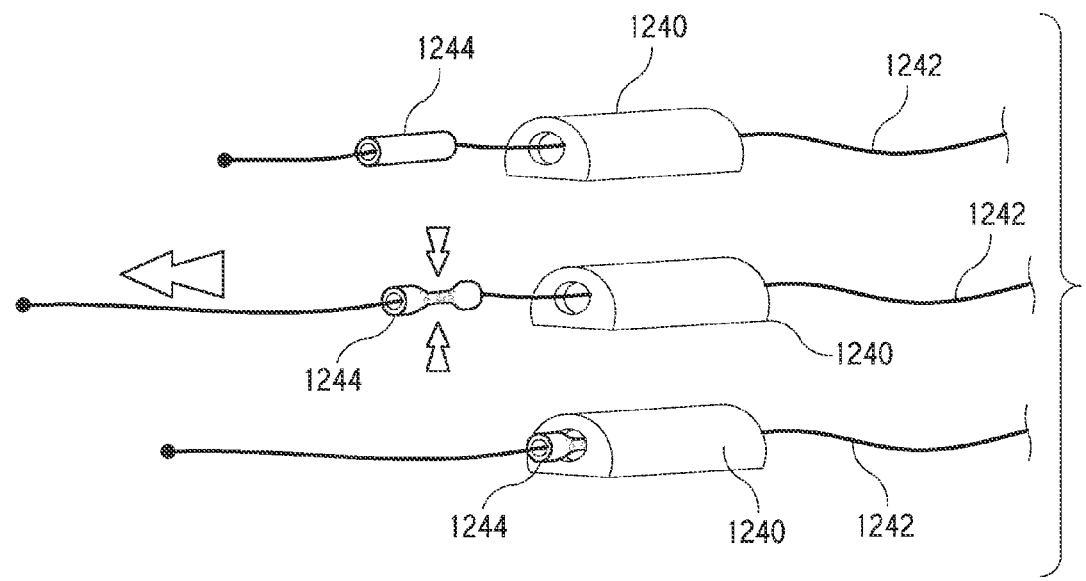
Figure 12I:
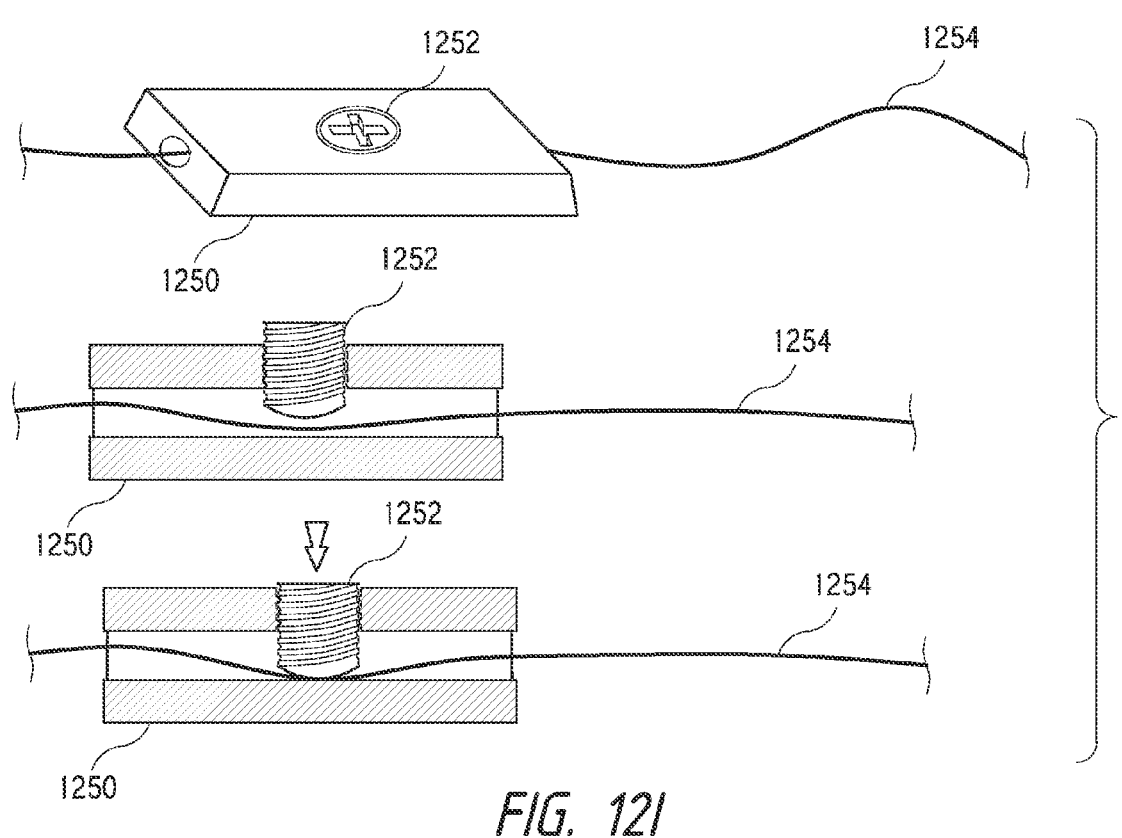

FIGS. 12E-G illustrate various ladder lock systems that may be used to vary the lace length. The ladder lock systems include a lock 1232a-c that may be moved proximally and distally along a ladder 1230a-c, respectively, and coupled therewith to increase or decrease the lace length within a zone of the shoe or article and thereby tension the lace by a desired amount. FIG. 12H illustrates another embodiment of a lace length varying system. In this embodiment, the lace 1242 may be pulled through a garage or stop component 1240 until the lace 1242 has a desired tension or lace length. A ferrule 1244 may then be crimped about the lace 1242 and the lace released. The ferrule 1244 prevents the lace 1242 from being pulled proximally through the garage 1240. As illustrated in FIG. 12I, in another embodiment the lace 1254 may be pulled through a collar or housing 1250 until the lace 1254 has a desired lace length or tension. A set screw 1252, detent, and the like, may then be screwed or positioned to pinch the lace 1254 within the collar 1250 and prevent proximal movement of the lace 1254 relative to the collar 1250. In both embodiments, an excess amount of the lace may be cut and discarded if desired.

Figure 12J:
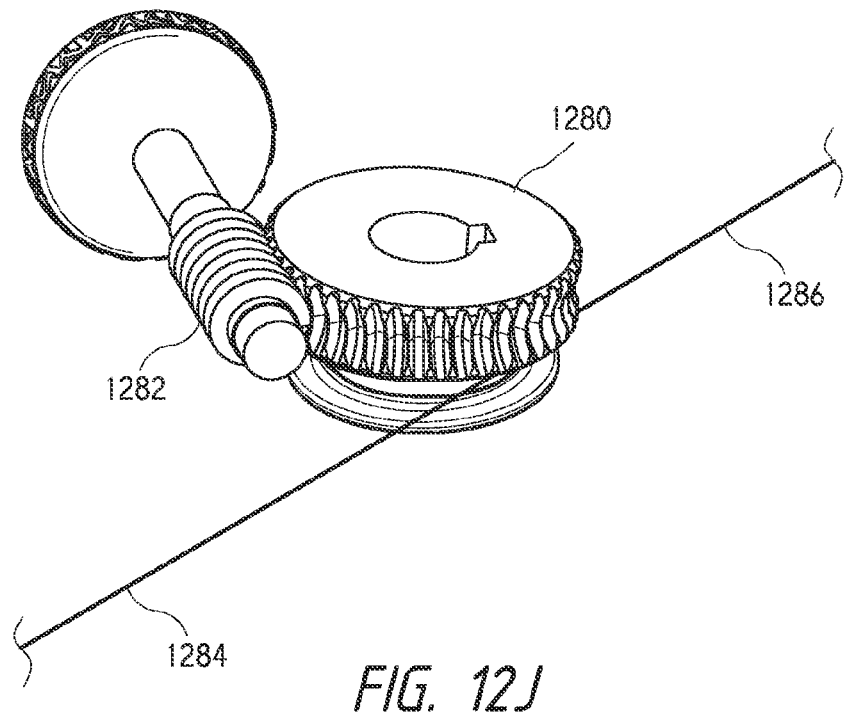
Figure 12K:
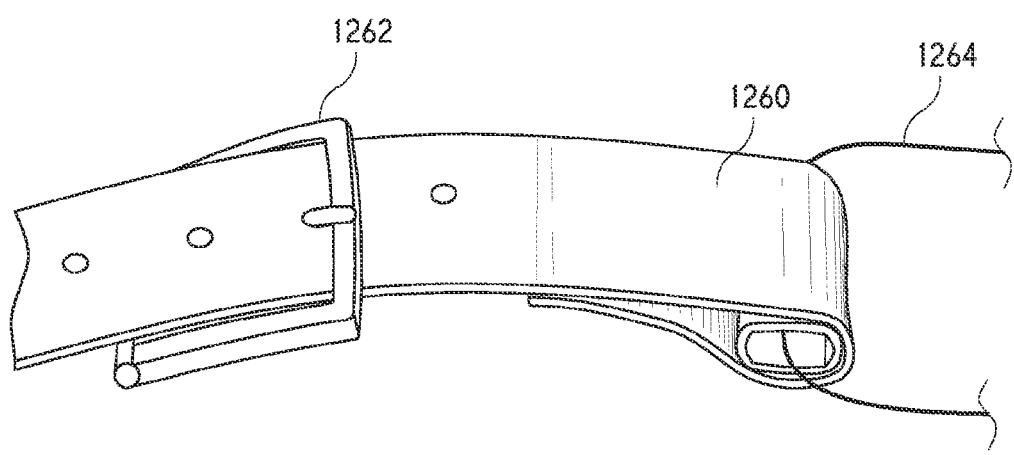
Figure 12L:
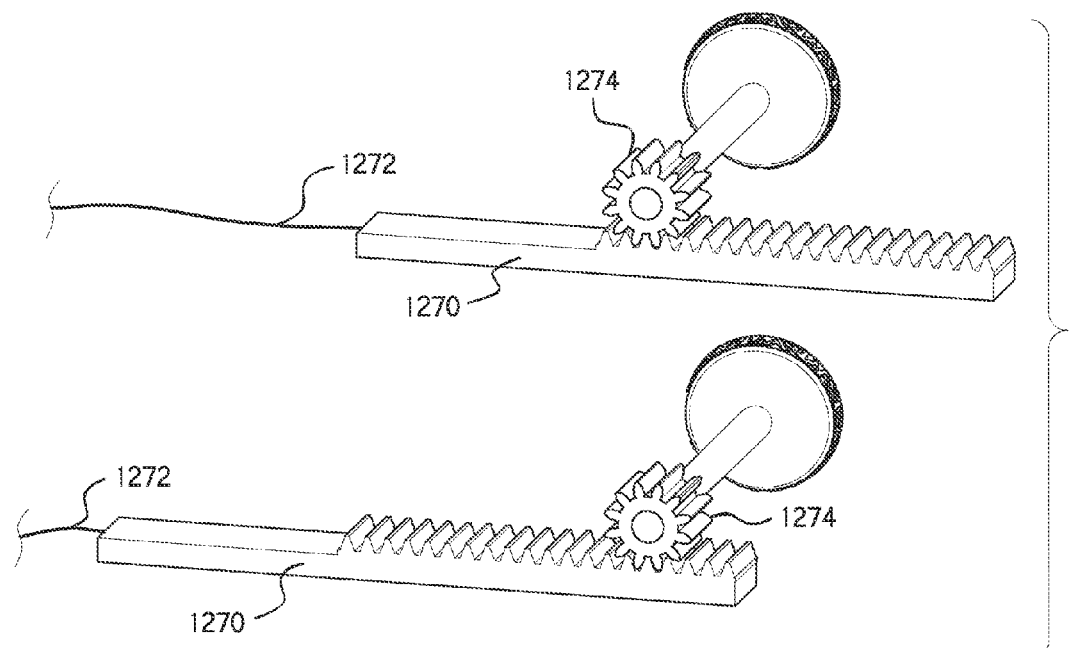
Figure 12M:
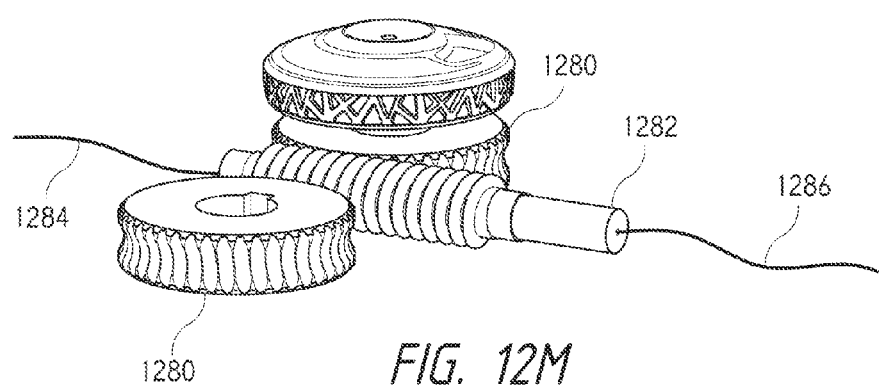
Figure 12N:
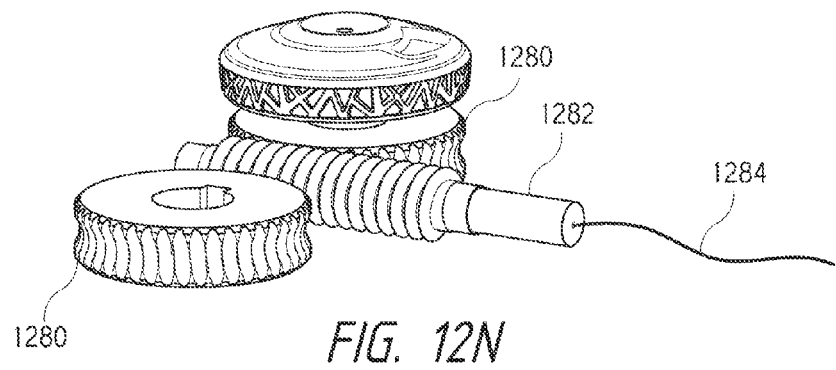
Figure 120:
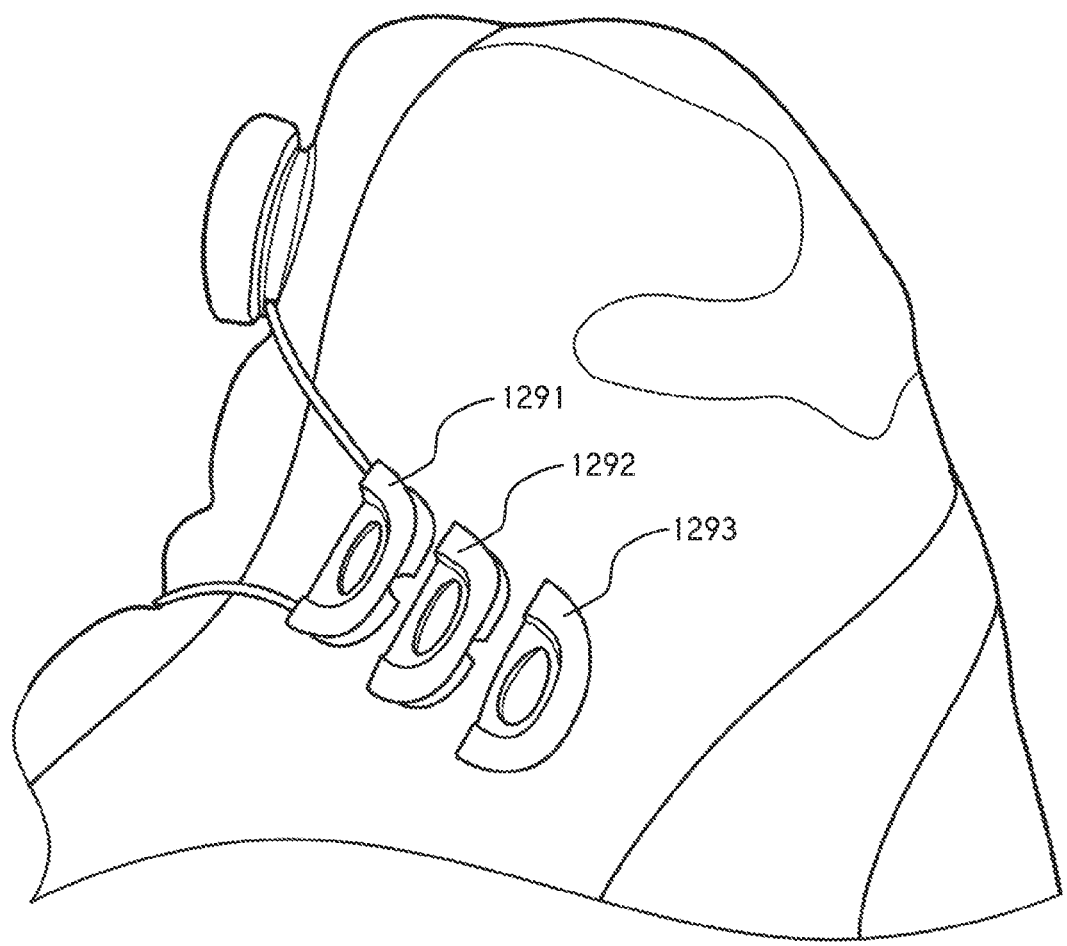
Figure 12P:
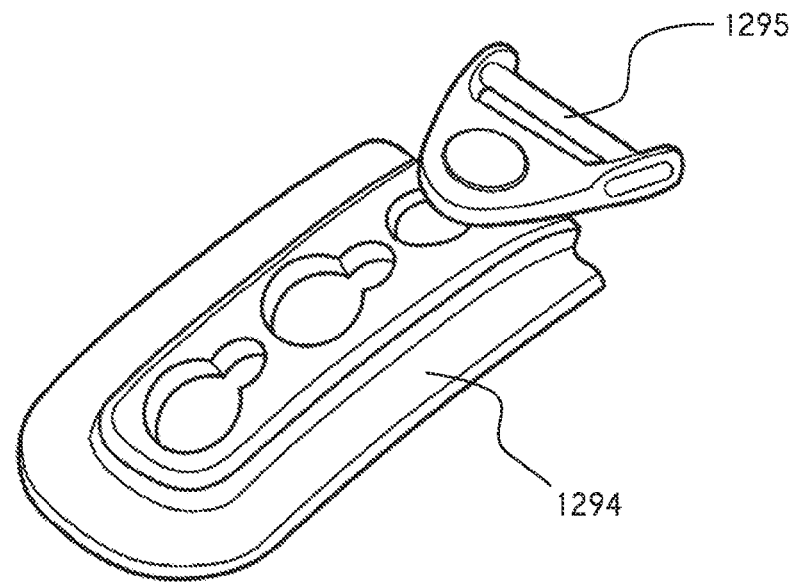
Figure 12Q:
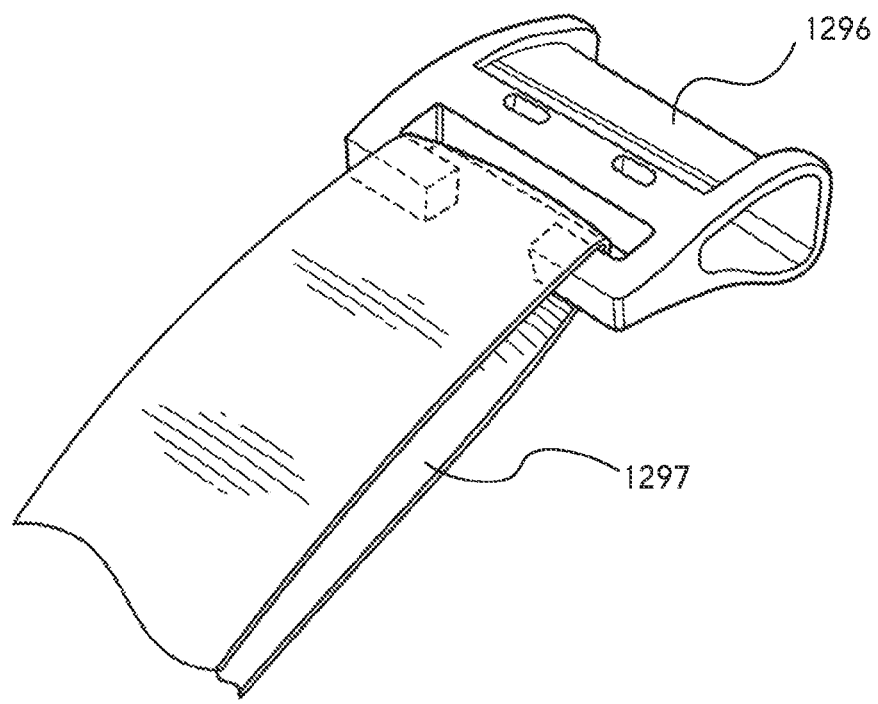
Figure 12R:
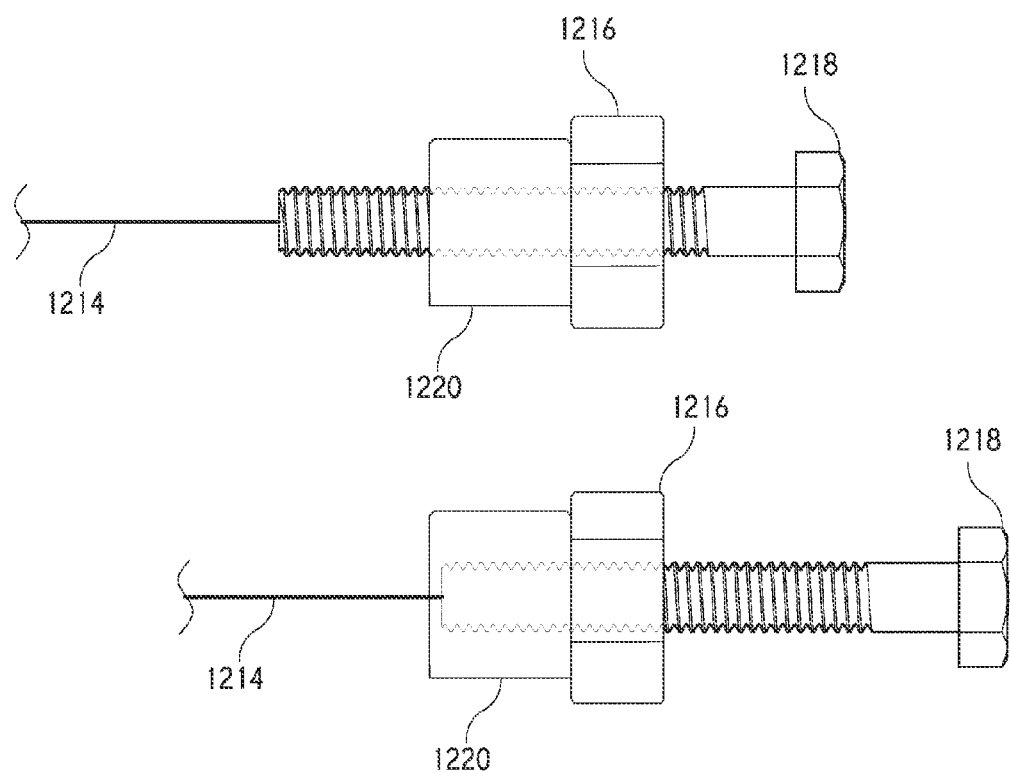

FIG. 12K illustrates yet another embodiment of a lace length adjustment system. In this embodiment, the lace 1264 may be coupled with webbing 1260 that is positioned through and coupled with a buckle component 1262. The webbing 1260 may include holes or other features that allow the webbing 1260 to be coupled at various positions about buckle 1262 to vary the lace 1264 length and/or tension. As shown in FIG. 12L, in another embodiment the lace 1272 may be coupled with a rack 1270 that is movable via a pinion 1274. Movement of the rack 1270 varies the lace length within a zone of the shoe or article and thereby tension the lace 1272 by a desired amount. In one embodiment, opposite ends of the rack 1270 may be coupled with a first lace 1272 and a second lace 1276 so that operation of the pinion 1274 and movement of the rack 1270 "teeter" and/or adjust the relative lengths of the first and second laces, 1272 and 1276, as described herein. As shown in FIGS. 12M and N, in another embodiment the lace 1284 may be coupled with a "worm" or "wormshaft" 1282 that may be moved proximally and distally via a worm gear 1280. Movement of the wormshaft 1282 may vary the lace length within a zone of the shoe or article and thereby tension the lace 1284 by a desired amount. In one embodiment, opposite ends of the wormshaft 1282 may be coupled with a first lace 1284 and a second lace 1286 so that operation of the worm gear 1280 and movement of the wormshaft 1282 "teeter" and/or adjust the relative lengths of the first and second laces, 1284 and 1286, as described herein. FIG. 12J illustrates another variation of the worm gear embodiment.

FIG. 12O illustrates an embodiment of a lace tension adjustment system. Specifically, the illustrated shoe includes a plurality of "open-back" guide members (i.e., 1291, 1292, and 1293) that are positioned adjacent one another about a side of the shoe. The open-back guide members include an open channel or back configuration that allows lace to be coupled or uncoupled from a respective guide member by placing the lace over the open channel, or removing the lace therefrom, in a hook like manner. Because the guide members (i.e., 1291, 1292, and 1293) are positioned adjacent one another about the side of the shoe, the lace may be removed from the open channel of one guide member and repositioned within an open channel of an adjacent guide member to increase or decrease the tension in the lace as desired.

FIG. 12P illustrates an embodiment of a lace tension adjustment system that includes a guide member 1295 that may be moved proximally and distally within a track 1294 to vary lace tension. The guide member 1295 is coupled with lace as described herein and includes a boss or projection that may be removably positioned within an aperture of the track 1294. The track 1294 includes multiple apertures that may be coupled with the boss or projection of the guide member 1295. In this manner, the guide member 1295 may be removed from one of the apertures of track 1294, moved proximally or distally with respect to track 1294, and repositioned within another aperture of track 1294 to tension the lace as desired. The track 1294 may be coupled with a side of a shoe similar to the arrangement of guides 1291-1293 to allow the guide member 1295 to be moved along or about the side of the shoe similar to the embodiment of FIG. 12O. FIG. 12Q is similar to FIG. 12P in that a guide member 1296 may be moved proximally and distally about a side of the shoe, but differs in that the guide member 1296 is configure to move along or about a strip of webbing or fabric 1297. The guide member 1296 includes a ring, hook, cam, or clamp component that allows the guide member 1296 to be coupled with fabric or webbing strip 1297. In this manner, the guide member 1296 may be moved about the shoe to tension lace that is coupled therewith by a desired amount. The embodiments of FIG. 12O-Q may be used to affect the differential tightening of one or more zones of a shoe by varying the tension in one or more laces positioned within the respective zone.

Gross Adjustment

Figure 13A:
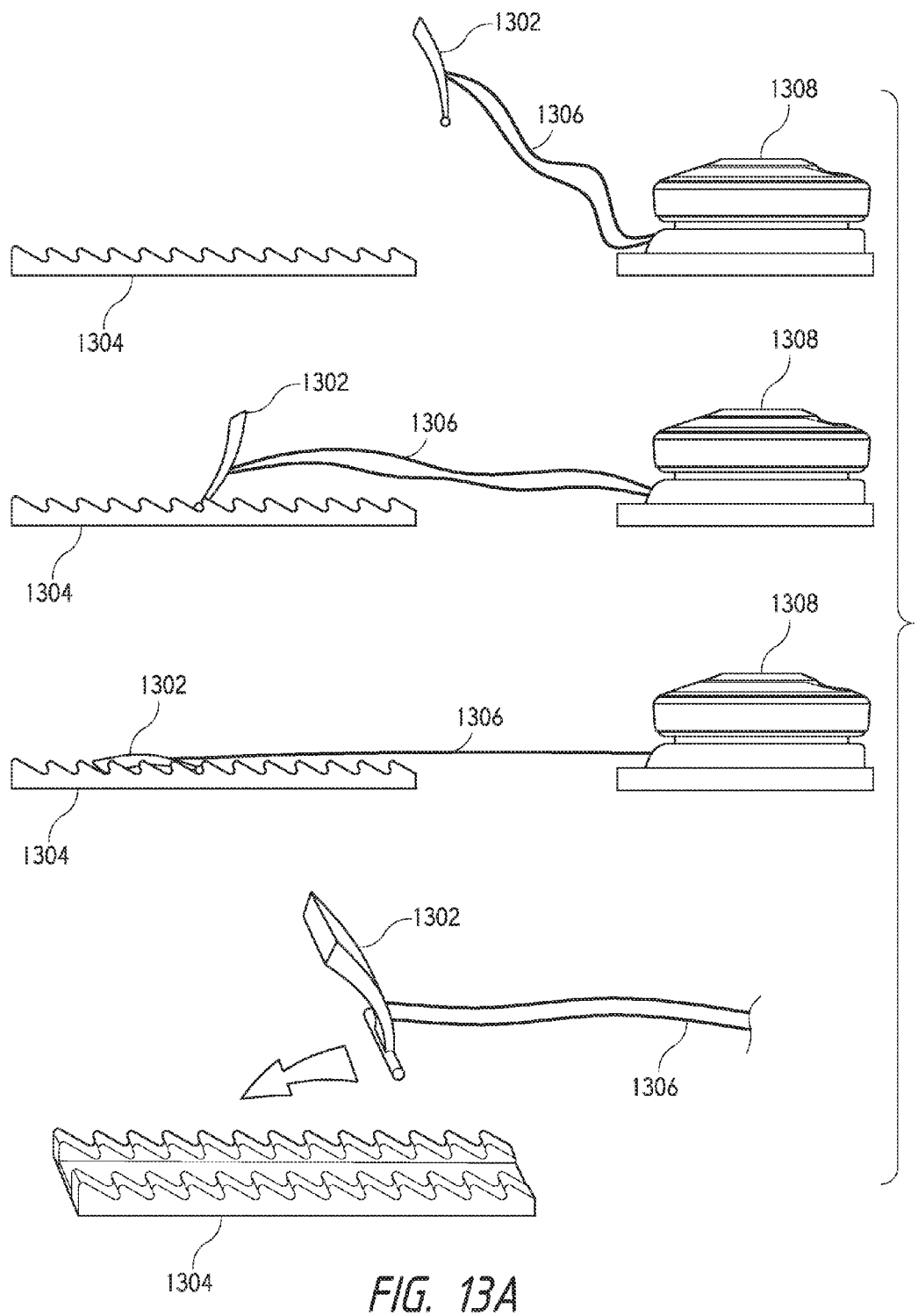
FIGS. 13A-E illustrate various embodiments of gross or macro adjustment mechanisms that may be used to provide gross or macro closure of a shoe or article.
Figure 13B:
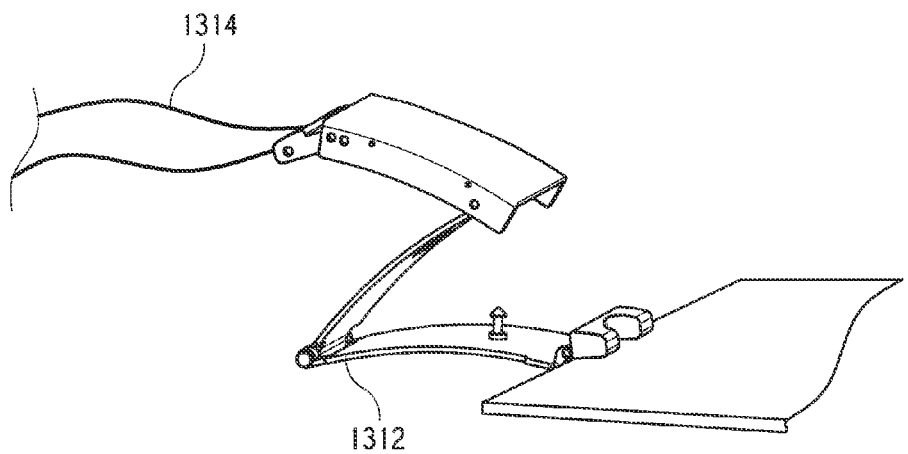
Figure 13C:
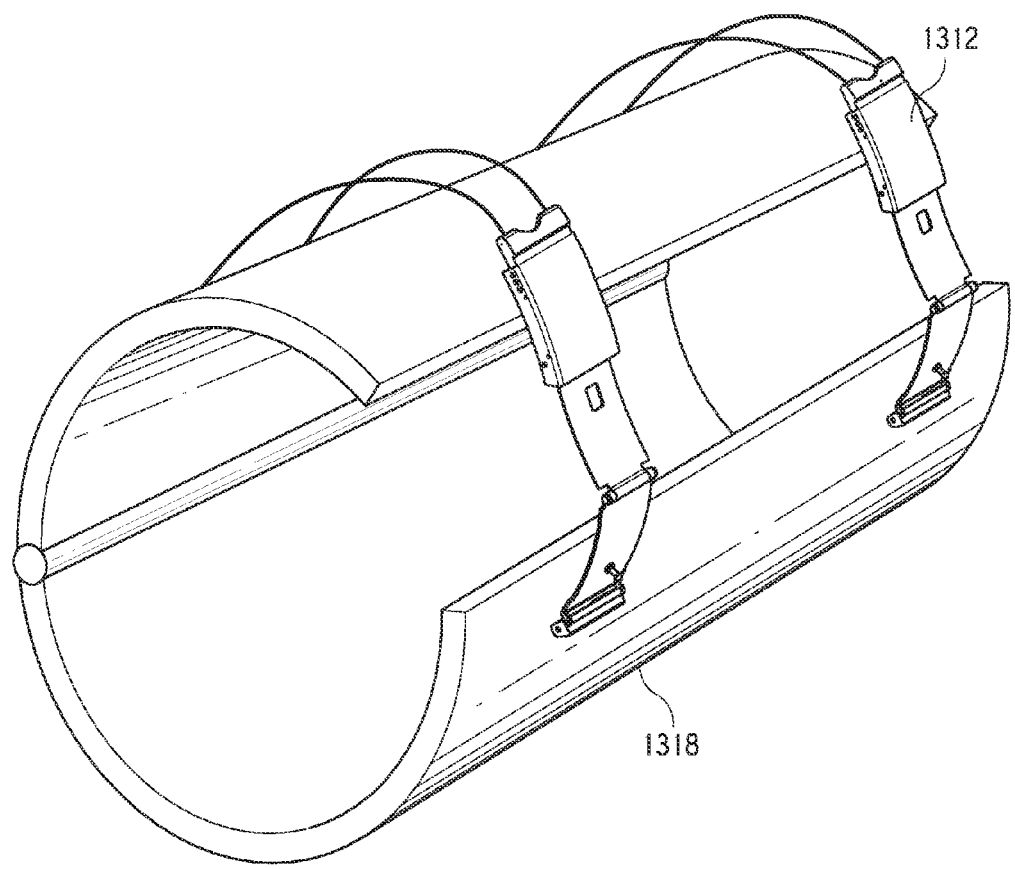

In one embodiment, the lace winding system may include gross or macro adjustment features. FIGS. 13A-E illustrate various embodiments of gross or macro adjustment. In FIGS. 13A-C the lace 1306 may be coupled with a lever 1302 that is positionable into one of a plurality of slots of a ladder system 1304 and folded over to tension the lace 1306 and provide gross or macro closure of an opening of the shoe or other device, such as a brace. The lace 1306 is subsequently wound via a reel assembly 1308 to provide fine or micro adjustment and/or tensioning of the lace 1306. In another embodiment, the lace 1314 may be coupled with multiple foldable panels 1312 that fold over one another to tension the lace 1314 and provide gross or macro closure of an opening of the shoe or other device, such as the illustrated brace 1318. A reel assembly (not illustrated) may be subsequently operated to provide fine or micro tensioning of the system.

Figure 13D:
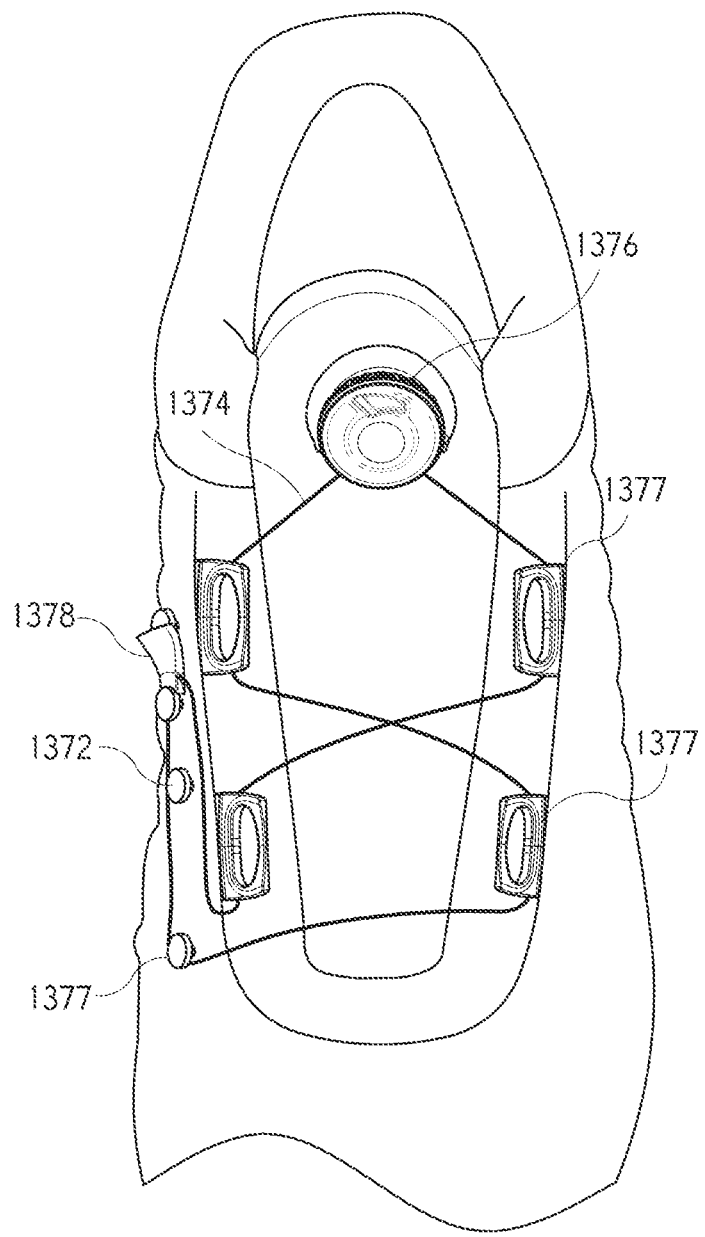
Figure 13E:
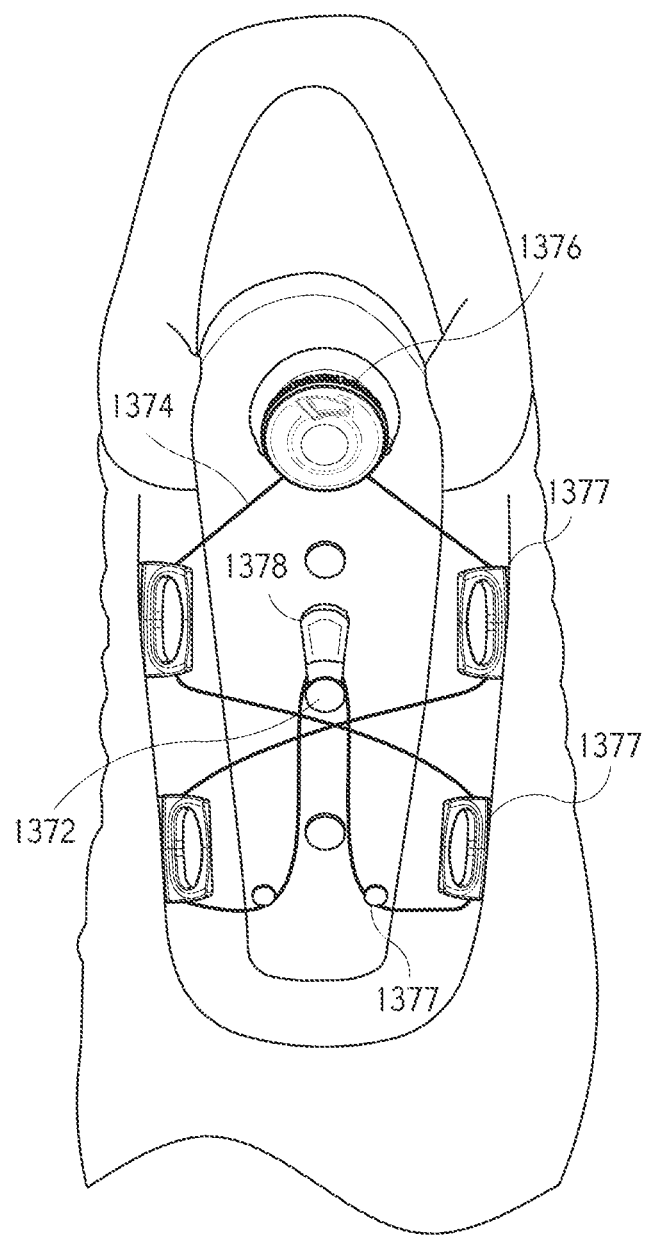

FIGS. 13D and 13E illustrate another embodiment of a gross or macro adjustment system. Specifically, a plurality of posts 1372 may be positioned along the shoe, such as centrally along the tongue or on one side of the shoe (or elsewhere). The lace 1374 may be pulled to close the shoe about the foot and a distal portion of the lace 1374 may be positioned around one of the posts 1372. The lace 1374 may be run through and/or around various guides 1377 as described herein. Proximally and distally moving the lace 1374 relative to the posts 1372 and positioning the lace 1374 around one of the posts 1372 provides gross adjustment of the fit of the shoe. Additional tensioning of the lace 1374 may then be achieved using reel assembly 1376 as described herein. In some embodiments, the distal portion of the lace 1374 that is positioned around the posts 1372 may include a pull tab 1378 to facilitate pulling and placement of the lace 1374 about the posts 1372.

Software Fitting System

In some embodiments, a system may use software in fitting a shoe to an individual user. For example, an image of the user's foot may be acquired (e.g., via picture, scan, sensed pressure, and the like) and a program may be run to determines or tailor a fit of the shoe to the user. For example, in one embodiment the user may stand on a sensory pad that measures pressure points from the user's foot. Based on the input received, the system may determine or calculate an optimal fit of the shoe for the user. The system may determine that additional heal compression is needed or that increased arch support is need for the user and provide this feedback to a service provider who would custom or tailor fit the shoe for the individual. The lace length, lace guide configuration, lace tension, and the like may be adjusted based on the feedback provided by the system. Likewise, the lace length, termination point of individual laces, reel selection, lace guide positioning, and the like may be adjusted based on the determined or calculated fit.

In another embodiment, the calculations may be provided to the user and the initial adjustments performed by the user. For example, a "fit number" may be displayed to the user as the user steps on a pressure scale or other device. The user may then adjust the configuration of the lace winding system based on the fit number. A small instructional manual may be provided to the user that instructs the user on adjusting the configuration based on the calculated fit number.

Since the shoe may be tailor fit to the individual user, gross adjustment of the shoe may not be needed. Rather, the gross adjustment of the shoe may be performed once and the user may only be required to perform subsequent micro-adjustments to the shoe. This may reduce the complexity of the overall closure system and provide the user with a more positive experience of the shoe closure system.

The above process may be particularly useful for closure systems having multiple lace termination points, multiple zones, or multiple laces because these configurations are typically less "self-adjusting" than single zone or lace systems. The individual zones, laces, and/or termination points may be tailor fit to the user, thereby reducing the complexity of properly fitting a shoe. Minor adjustments may then be compensated for by the user, which adjustments are typically less difficult or taxing. The above described system may also be used in fitting medical devices or braces with the lace winding system.

Torsion Bar or Flexible Tensioning Shaft

Figure 14A:
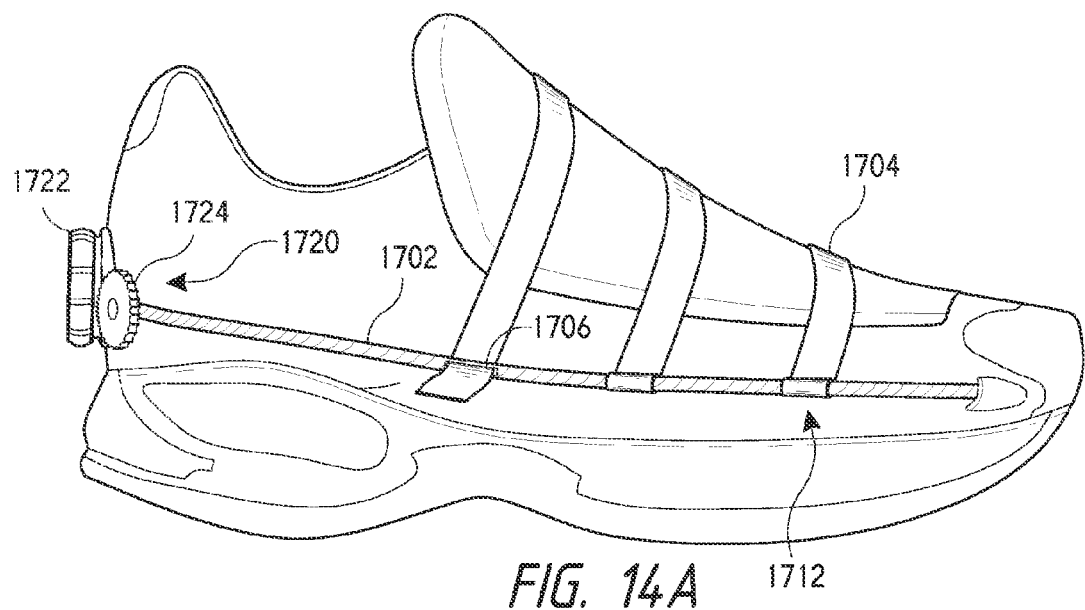
FIGS. 14A-E illustrate various embodiments of tensioning rods or shaft that may be used to tension one or more zones of the shoe or article.
Figure 14B:
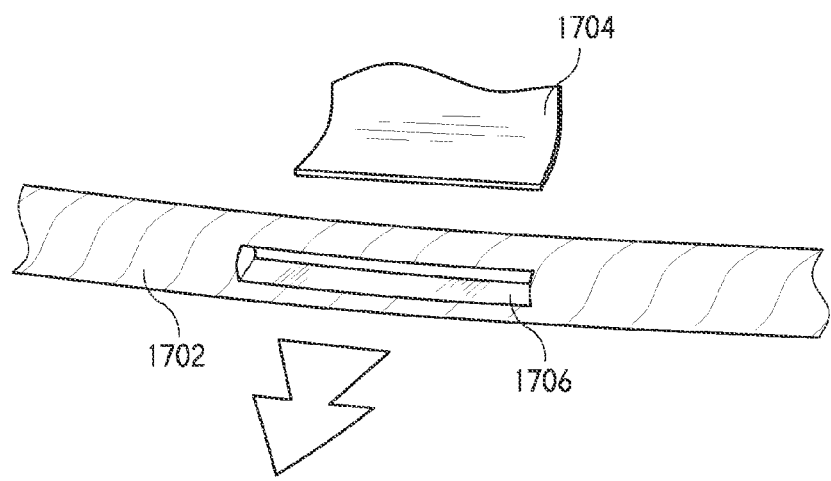
Figure 14C:
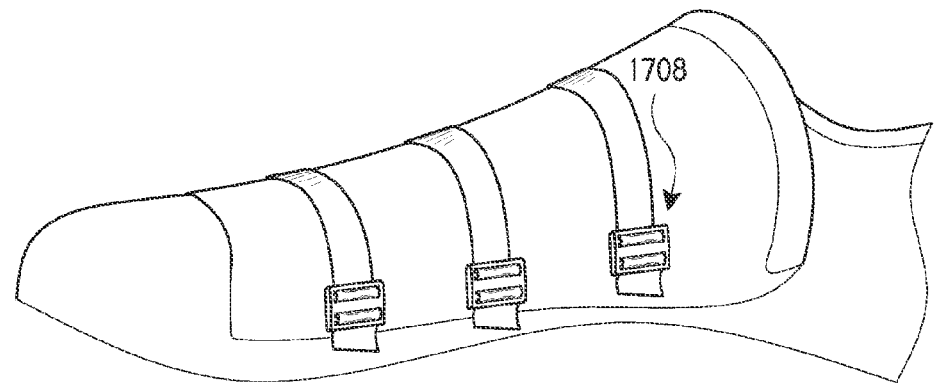

In another embodiment, the zonal fit of the shoe about the user's foot may be adjusted by using a flexible tensioning shaft or a torsion bar. As shown in FIGS. 14A-C, a rod or flexible tensioning shaft 1702 may extend along the medial or lateral side of the shoe and may be used to tension a plurality of zones of the shoe. A lace or strap 1704 length from the flexible tensioning shaft 1702 to each of the zones may be adjusted based on the shape of the user's foot, and/or for various other reasons, so that tensioning of the lace or strap 1704 via the flexible tensioning shaft 1702 provides a custom fit. The lace or strap 1704 lengths for one or each of the zones may be determined using the software and system described previously, or using any other manner. The lace or strap ends 1708 may be adjusted and terminated as described herein, such as by using a locking component (e.g., ladder lock, buckle, and the like) and adjusting a distal end of the lace or strap 1704 relative to the locking component.

In some embodiments, the lace or strap 1704 may be coupled with the flexible tensioning shaft 1702 by inserting an end of the lace or strap 1704 through a slot 1706 in the flexible tensioning shaft 1702. The lace of strap 1704 may then be wound on itself via the flexible tensioning shaft 1702 and a gear mechanism 1720, which may include a reel assembly 1722 and gear 1724. In some embodiments, the flexible tensioning shaft 1702 may be disposed or positioned within tubing (not shown) that is in turn disposed within on upper material of the shoe or positioned externally thereof. In other embodiments, the flexible tensioning shaft 1702 may extend along an outer surface of the shoe and be coupled therewith using one or more bearings or locks (not shown).

In one embodiment, the flexible tensioning shaft 1702 may have an adjustable slip clutch at one or more of the zones that allows the lace or strap 1704 within one or more zones to be tensioned to or by a defined amount. For example, the adjustable slip clutch may be set at a desired tension and the flexible tensioning shaft 1702 tensioned (e.g., via reel assembly 1722) until the zone or zones reaches the set tension. After reaching the set tension, the clutch may slip so that additional tension is not applied to the lace or strap 1704. When the slip clutch 1712 is adjusted to a desired tension, the slip clutch may be "locked out" so as to slip at the desired tension. In this manner, the tension in one or more zone, and in some embodiments each zone, may be controlled so that respective laces are tensioned by a desired amount. In some embodiments, the laces or straps 1704 may be coupled with additional straps that allow gross adjustment of the individual laces and/or fine tuning of the lace or strap 1704 tension via the flexible tensioning shaft 1702 and/or slip clutch system.

The slip clutch may also allow the overall design of the reel and lace winding system to be simplified. For example, the reel may be designed to withstand over tightening by relatively strong individuals to ensure that the reel and lace winding system does not break. These design constraints may be relaxed with the use of a slip clutch since the system may only allow a defined amount of tension to be placed on the lace before the reel and/or lace winding system slip.

In another embodiment, the lace may terminate in one or more ends that are configured to compensate for or adjust to different lace tensions. Using such ends, lace in individual zones of the shoe may be tensioned to a desired amount. For example, the lace may be coupled with webbing ends that begin to elastically deform or stretch when a defined tension is applied. The lace in each zone may be adjusted to deform at the same or differential tensions so that a desired tension in each zone is ultimately provided. The user may tension the system until a comfortable fit is achieved. If a different fit in one or more zones is subsequently desired, the lace ends (e.g., webbing ends) may be adjusted so as to deform at a different tension. The differential tension may also be achieved by adjusting the lace length at the termination points. The lace ends and/or lace length may then be "locked out" so that a desired tension is achieved in the one or more zones.

In yet another embodiment, the above described slip clutch may be used to determine an initial tension and then subsequently "locked out" so that the lace in individual zones is tensioned by approximately the same amount. For example, the lace may be wound and each lace may be tensioned to a defined amount. When the laces are tensioned to the defined amount, the slip clutch system may be locked so that additional tensioning of the system tensions the laces in each zone by roughly the same amount.

In some embodiments, the lace or straps 1704 in separate zones may be differentially tensioned to differentially tighten the separate zones. This may improve the fit and/or comfort of the shoe. Differential tension may be achieved by varying the lace or strap 1704 length within the various zones. Subsequent operation of the reel assembly 1722 may then differentially tension the lace or straps 1704. The lace or strap length may be varied on the side of the shoe adjacent the flexible tensioning shaft 1702 and/or on the opposite side adjacent end 1708. In some embodiments, rotation of the flexible tensioning shaft 1702 winds approximately an equal length of the lace or straps 1704 around the rod body of flexible tensioning shaft 1702, or unwinds approximately an equal length of the lace or straps 1704 therefrom.

Figure 14D:
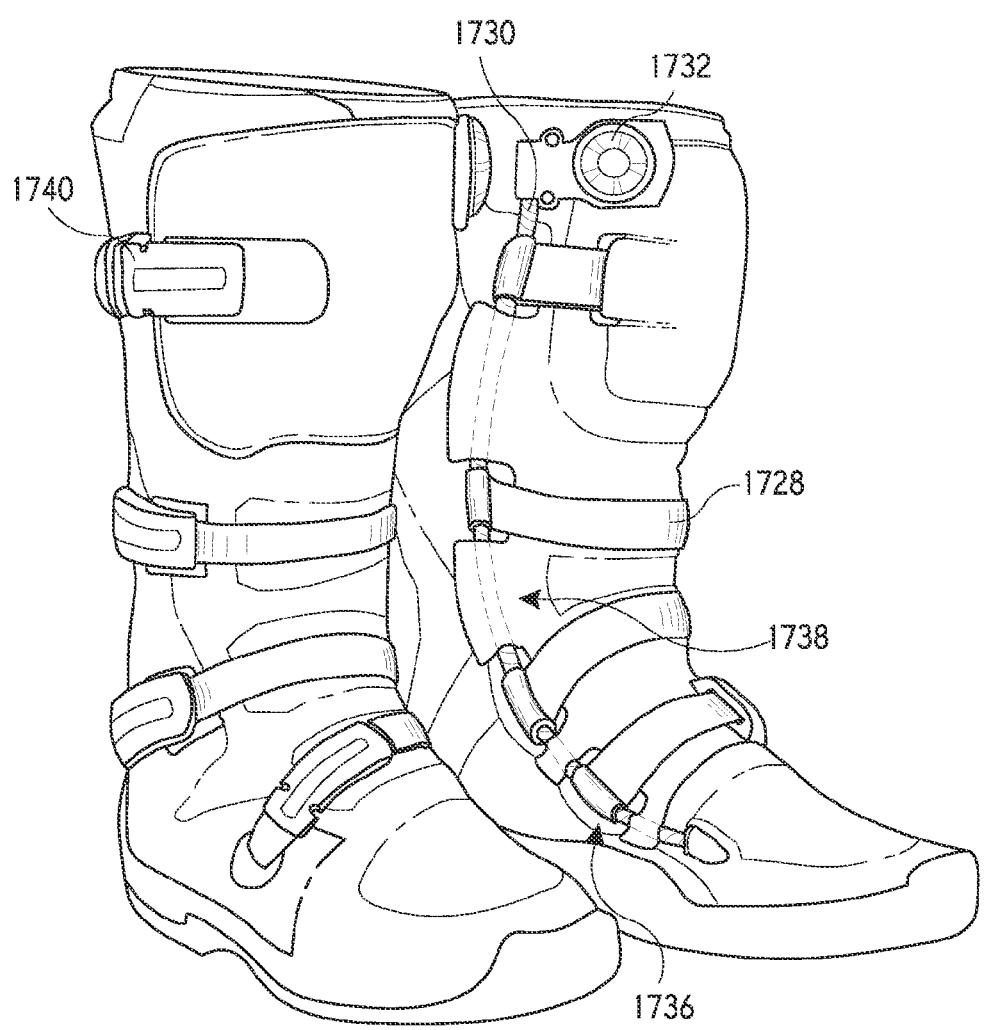
Figure 14E:
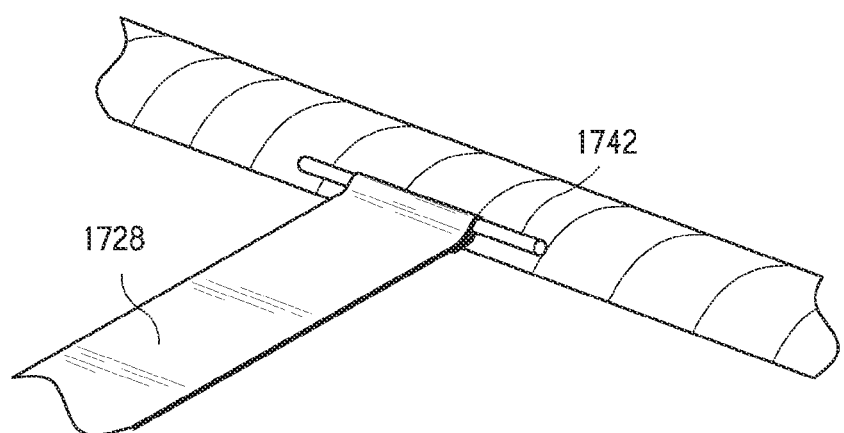

FIGS. 14D and 14E illustrate another embodiment of a flexible tensioning shaft 1730 being used to tension a boot. The flexible tensioning shaft system includes a reel assembly 1732 and one or more gears (not shown) that rotate or twist flexible tensioning shaft 1730. Positioned along the longitudinal length of flexible tensioning shaft 1730 are one or more laces or straps 1728 that extend across the forefront and/or tongue of the boot. The laces or straps 1728 are coupled with a gross adjustment mechanism, such as a camlock or lever buckle 1740 that may be pulled, inserted into a grooved slot, and rotated to initially tension the lace or straps 1728. Lever mechanism 1740 may be similar to that previously described embodiments. The straps 1728 may be coupled with flexible tensioning shaft 1730 via slots, weld bars 1742, pinch points, buckles, and the like. FIGS. 14D and 14E further illustrate flexible tensioning shaft 1730 traversing several slots or channels 1738 that hold the flexible tensioning shaft 1730 in place relative to the boot and that allow the flexible tensioning shaft 1730 to be rotated to tension the laces or straps 1728.

Other Embodiments

In another embodiment, the shoe may include a single strap, or a few straps, that are positioned around the shoe. The lace of the winding system may go around the shoe, or be coupled with the strap, so that as the lace is tensioned, a single "cinch" point is created where the shoe closes or comes together.

In another embodiment, the lace winding system may be designed to grab a portion or portions of the body, such as the heel and mid-foot. This embodiment may be particularly useful in ankle brace applications to stabilize that portion of the foot. The lace winding system may pull opposite sides of the shoe together to provide this support. For example, the lace winding system may be coupled with a "pita pocket" or opposite sides of the shoe near the midsole so that as the lace is tightened, the pocket or opposite sides of the show tighten, or puff up, around the user's foot in a supportive manner.

In another embodiment, a portion of the shoe may be adjusted to the user and then the lace winding system subsequently coupled with the shoe. For example, the shoe "upper" may be elastic and may be fit to the user's foot prior to the lace winding system being coupled with the shoe. The shoe's upper, or any other portion of the shoe, may be composed of an initial settable material, such as a thermally settable material, light settable, and the like, so that the shoe conforms to the shape of the user's foot upon the application of heat, UV light, and the like. For example, a thermally formable piece of plastic (e.g., Lycra) may be positioned within an interior portion of, or throughout, the shoe, such as within foam padding. The shoe may then be formed to the user's foot and thermally set in that position so that the shoe is essentially an approximately perfect fit. The lace winding system may then be coupled with the shoe and/or custom fit to the shoe to allow easy donning and doffing thereof. Custom fitting the shoe in this manner may provide a more desirable "shrink wrap" feel where the user's foot is in increased contact with and/or cushioned by the shoe material.

In one embodiment, a formable or elastic upper may be integrated with roughly rigid parts or pieces of the shoe so that a better fit of the shoe with the lace winding system is provided. The formable or elastic upper may be formed to the user's foot and "locked" in the formed shape so that the ultimate shoe system is static and not necessarily elastic.

In another embodiment, a deformable member may be coupled with the shoe to allow the shoe to be custom fit to the individual user. For example, a deformable rod, wire, plates, shaft, and the like, may be inserted within a portion of the shoe. The deformable member may then be bent or formed into a custom shape that allows a custom fit or closure for the specific user. The deformable member be hardened (e.g., work hardened, cured, and the like) so that it maintains the custom shape and the shoe is custom fit to the user. In some embodiments, the deformable member may be formed external to the shoe with a specific piece of equipment or prior to inserting within the shoe. In a specific embodiment, the deformable member may be used to shape the eyestay of the shoe.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A lacing system for tightening a shoe comprising:
   a plurality of first guide members coupled with the shoe and defining a first zone of the shoe;
   a plurality of second guide members coupled with the shoe and defining a second zone of the shoe, wherein at least a portion of the second zone is different than the first zone;
   a first tension member guided by the plurality of first guide members within the first zone, the first tension member being configured to tighten the first zone of the shoe upon tensioning of the first tension member;
   a second tension member guided by the plurality of second guide members within the second zone, the second tension member being configured to tighten the second zone of the shoe upon tensioning of the second tension member;
   a tensioning mechanism coupled with the shoe and with the first tension member and the second tension member, the tensioning mechanism being operable to tension the first and second tension members so as to tighten the first and second zones; and
   an adjustment mechanism that is coupled with the first and second tension members and that is operable independent of the tensioning mechanism, the adjustment mechanism being configured to vary a length of the first and second tension members within the respective zones by decreasing the length of one of the tension members within the respective zone and increasing the length of the other tension member within the respective zone by a corresponding amount;
   wherein varying the length of the first and second tension members within the respective zones varies the tension applied to the first tension member and the second tension member upon operation of the tensioning mechanism.

2. The lacing system of claim 1, wherein the adjustment mechanism includes a rotatable knob.

3. The lacing system of claim 2, wherein the knob is rotatable to decrease the length of the first tension member within the first zone and to increase the length of the second tension member within the second zone by a corresponding amount.

4. The lacing system of claim 1, wherein the tensioning mechanism is coupled with a side of the shoe.

5. The lacing system of claim 1, wherein the adjustment mechanism is configured to allow the first and second tension members to be moved relative to the adjustment mechanism in order to vary the length of the first and second tension members within the respective zones and wherein the adjustment mechanism is further configured to secure the first and second members in position relative to one another.

6. A lacing system for tightening a shoe comprising:
   a plurality of first guide members coupled with the shoe and positioned within a first zone of the shoe, the plurality of first guide members including at least two open back guides that are positioned and aligned on a side of the shoe so that a first open back guide is positioned closer to a tongue portion of the shoe than a second open back guide, wherein each open back guide includes an open channel or back that enables a tension member to be removably positioned within a respective open back guide of the at least two open back guides;
   a second guide member coupled with the shoe and positioned within a second zone of the shoe, wherein at least a portion of the second zone is different than the first zone;
   a first tension member guided by the plurality of first guide members within the first zone, wherein tensioning of the first tension member causes tightening of the first zone of the shoe;
   a second tension member guided by the second guide member within the second zone, wherein tensioning of the second tension member causes tightening of the second zone of the shoe; and
   a tensioning mechanism coupled with the shoe and with the first tension member and the second tension member, the tensioning mechanism being operable to tension the first and second tension members to tighten the first and second zones;
   wherein the first tension member is adjustable within the first zone independent of operation of the tensioning mechanism such that upon operation of the tensioning mechanism, a tension applied to the first tension member is different than a tension applied to the second tension member.

7. The lacing system of claim 6, wherein the tensioning mechanism causes a differential tension to be applied to the first tension member and the second tension member to differentially tighten the first and second zones.

8. The lacing system of claim 7, wherein the tensioning mechanism includes a spool having a first portion around which the first tension member is wound and a second portion around which the second tension member is wound, wherein a diameter of the first portion is different than a diameter of the second portion such that winding the first and second tension members around the spool causes the differential tension to be applied to the first and second tension members.

9. The lacing system of claim 7, wherein the tensioning mechanism includes a first spool around which the first tension member is wound and a second spool around which the second tension member is wound, and wherein a gear or clutch mechanism of the tensioning mechanism causes rotation of the first and second spools at different rates to cause the differential tension to be applied to the first and second tension members.

10. The lacing system of claim 7, further comprising an adjustment mechanism that is coupled with the first and second tension members, the adjustment mechanism being configured to vary a length of the first and second tension members within the respective zones so as to vary the differential tightness applied to the respective zones by the first and second tension members.

11. The lacing system of claim 10, wherein the tensioning mechanism includes the adjustment mechanism.

12. The lacing system of claim 10, wherein the adjustment mechanism is coupled with the shoe separate from the tensioning mechanism and adjacent the first or second zones.

13. The lacing system of claim 10, wherein the adjustment mechanism is configured to decrease the length of one of the tension members within the respective zone and to increase the length of the other tension member within the respective zone by a corresponding amount.

14. The lacing system of claim 6, wherein the tensioning mechanism includes a spool having a first portion around which the first tension member is wound and a second portion around which the second tension member is wound, wherein the first portion of the spool includes a first channel for the first tension member and the second portion of the spool includes a second channel for the second tension member, the first channel being separate from the second channel to prevent tangling of the first and second tension members.

15. The lacing system of claim 7, wherein a proximal end of the first tension member is coupled with the tensioning mechanism and a distal end of the first tension member is coupled with the shoe or with a second guide member positioned within the first zone.

16. The lacing system of claim 15, wherein a proximal end of the second tension member is coupled with the tensioning mechanism and a distal end of the second tension member is coupled with the shoe or with a second guide member positioned within the second zone.

17. The lacing system of claim 6, wherein a distal end of the first tension member includes a tab that is graspable by a user to enable the user to adjust the distal end of the first tension member relative to the shoe.

18. The lacing system of claim 6, wherein the first tension member is adjustable relative to the shoe by positioning the first tension member within the first open back guide or the second open back guide, wherein adjusting the first tension member relative to the shoe varies the tension applied to the first tension member and the second tension member via the tensioning mechanism.

19. A lacing system for tightening a shoe comprising:
a first guide member coupled with the shoe and positioned within a first zone of the shoe;
a second guide member coupled with the shoe and positioned within a second zone of the shoe, wherein at least a portion of the second zone is different than the first zone;
a first tension member guided by the first guide member within the first zone, the first tension member being configured to tighten the first zone of the shoe upon tensioning of the first tension member;
a second tension member guided by the second guide member within the second zone, the second tension member being configured to tighten the second zone of the shoe upon tensioning of the second tension member; and
a tensioning mechanism coupled with the shoe and with the first tension member and the second tension member, the tensioning mechanism being operable to tension the first and second tension members so as to tighten the first and second zones;
wherein the first tension member is adjustable relative to the shoe independent of operation of the tensioning mechanism such that upon operation of the tensioning mechanism, a tension applied to the first tension member is different than a tension applied to the second tension member;
wherein a distal end of the first tension member is coupled with the shoe or with a second guide member positioned within the first zone, the distal end of the first tension member being adjustable relative to the shoe to vary a tensionable length of the first tension member within the first zone; and
wherein the distal end of the first tension member includes a grippable tab for adjustment of the first tension member relative to the shoe.

20. The lacing system of claim 19, wherein a proximal end of the first tension member is coupled with a first portion of a spool, and wherein a proximal end of the second tension member is coupled with a second portion of the spool, wherein a diameter of the first portion of the spool is different than a diameter of the second portion of the spool such that winding the first and second tension members around the spool causes a differential tension to be applied to the first and second tension members.

21. The lacing system of claim 19, wherein a distal end of the second tension member is coupled with the shoe or with a second guide member positioned within the second zone.

22. The lacing system of claim 17, wherein the distal end of the second tension member is adjustable relative to the shoe to vary a tensionable length of the second tension member within the second zone of the shoe.

23. The lacing system of claim 22, wherein the distal end of the second tension member includes a grippable tab for adjustment of the second tension member relative to the shoe.

* * * * *